United States Patent
Waldstreicher et al.

(10) Patent No.: US 10,702,337 B2
(45) Date of Patent: Jul. 7, 2020

(54) METHODS, APPARATUSES, AND SYSTEMS FOR THE TREATMENT OF PULMONARY DISORDERS

(71) Applicant: Galary, Inc., Menlo Park, CA (US)

(72) Inventors: Jonathan Reuben Waldstreicher, West Orange, NJ (US); William Sanford Krimsky, Forest Hill, MD (US); Denise Marie Zarins, Saratoga, CA (US); Robert J. Beetel, III, Sunnyvale, CA (US); Paul Brian Friedrichs, Belmont, CA (US); Kevin James Taylor, San Mateo, CA (US); Roman Turovskiy, San Francisco, CA (US); Gary L. Long, Cincinnati, OH (US)

(73) Assignee: Galary, Inc., Menlo Park, CA (US)

( * ) Notice: Subject to any disclaimer, the term of this patent is extended or adjusted under 35 U.S.C. 154(b) by 0 days.

(21) Appl. No.: 16/381,745

(22) Filed: Apr. 11, 2019

(65) Prior Publication Data
US 2019/0231425 A1    Aug. 1, 2019

Related U.S. Application Data

(63) Continuation of application No. 16/227,796, filed on Dec. 20, 2018, which is a continuation of application No. PCT/US2017/039527, filed on Jun. 27, 2017.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61N 1/06* (2013.01);
(Continued)

(58) Field of Classification Search
CPC ............ A61B 18/1206; A61B 18/1492; A61B 2018/0022; A61B 2018/00267;
(Continued)

(56) References Cited

U.S. PATENT DOCUMENTS

| 5,304,120 A | 4/1994 | Crandell et al. |
| 5,507,724 A | 4/1996 | Hofmann et al. |

(Continued)

FOREIGN PATENT DOCUMENTS

| AT | 306859 B | 4/1973 |
| AU | 2000480070 A1 | 11/2000 |

(Continued)

OTHER PUBLICATIONS

International Search Report and Written Opinion dated Dec. 7, 2017 for International Application No. PCT/US2017/039527, 22 pages.
(Continued)

*Primary Examiner* — Michael F Peffley
*Assistant Examiner* — Amanda L Zink
(74) *Attorney, Agent, or Firm* — Wilson Sonsini Goodrich & Rosati

(57) ABSTRACT

Apparatuses, systems and methods are provided for treating pulmonary tissues via delivery of energy, generally characterized by high voltage pulses, to target tissue using a pulmonary tissue modification system (e.g., an energy delivery catheter system). Example pulmonary tissues include, without limitation, the epithelium (the goblet cells, ciliated pseudostratified columnar epithelial cells, and basal cells), lamina propria, submucosa, submucosal glands, basement membrane, smooth muscle, cartilage, nerves, pathogens resident near or within the tissue, or a combination of any of these. The system may be used to treat a variety of pulmonary diseases or disorders such as or associated with COPD (e.g., chronic bronchitis, emphysema), asthma, interstitial
(Continued)

pulmonary fibrosis, cystic fibrosis, bronchiectasis, primary ciliary dyskinesia (PCD), acute bronchitis and/or other pulmonary diseases or disorders.

30 Claims, 43 Drawing Sheets

Related U.S. Application Data

(60) Provisional application No. 62/489,753, filed on Apr. 25, 2017, provisional application No. 62/355,164, filed on Jun. 27, 2016.

(51) Int. Cl.
*A61N 1/06* (2006.01)
*A61N 1/32* (2006.01)
*A61B 18/00* (2006.01)

(52) U.S. Cl.
CPC ...... *A61N 1/327* (2013.01); *A61B 2018/0016* (2013.01); *A61B 2018/0022* (2013.01); *A61B 2018/00267* (2013.01); *A61B 2018/00541* (2013.01); *A61B 2018/00577* (2013.01); *A61B 2018/00642* (2013.01); *A61B 2018/00648* (2013.01); *A61B 2018/00678* (2013.01); *A61B 2018/00702* (2013.01); *A61B 2018/00791* (2013.01); *A61B 2018/00839* (2013.01); *A61B 2018/00875* (2013.01); *A61B 2018/1435* (2013.01); *A61B 2018/1467* (2013.01)

(58) Field of Classification Search
CPC ........... A61B 2018/00541; A61B 2018/00642; A61B 2018/00678; A61B 2018/00702; A61B 2018/00791; A61B 2018/00839; A61B 2018/1435
See application file for complete search history.

(56) References Cited

U.S. PATENT DOCUMENTS

| | | | |
|---|---|---|---|
| 5,704,908 | A | 1/1998 | Hofmann et al. |
| 5,972,026 | A | 10/1999 | Laufer et al. |
| 6,009,347 | A | 12/1999 | Hofmann |
| 6,083,255 | A | 7/2000 | Laufer et al. |
| 6,120,493 | A | 9/2000 | Hofmann |
| 6,200,333 | B1 | 3/2001 | Laufer |
| 6,219,577 | B1 | 4/2001 | Brown, III et al. |
| 6,261,831 | B1 | 7/2001 | Agee |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,299,633 | B1 | 10/2001 | Laufer |
| 6,326,177 | B1 | 12/2001 | Schoenbach et al. |
| 6,411,852 | B1 | 6/2002 | Danek et al. |
| 6,488,673 | B1 | 12/2002 | Laufer et al. |
| 6,520,950 | B1 | 2/2003 | Hofmann et al. |
| 6,634,363 | B1 | 10/2003 | Danek et al. |
| 6,678,558 | B1 | 1/2004 | Dimmer et al. |
| 6,697,670 | B2 | 2/2004 | Chomenky et al. |
| 6,770,070 | B1 | 8/2004 | Balbierz |
| 6,795,728 | B2 | 9/2004 | Chornenky et al. |
| 6,892,099 | B2 | 5/2005 | Jaafar et al. |
| 6,994,706 | B2 | 2/2006 | Chornenky et al. |
| 7,027,869 | B2 | 4/2006 | Danek et al. |
| 7,054,685 | B2 | 5/2006 | Dimmer et al. |
| 7,104,987 | B2 | 9/2006 | Biggs et al. |
| 7,130,697 | B2 | 10/2006 | Chornenky et al. |
| 7,198,635 | B2 | 4/2007 | Danek et al. |
| 7,200,445 | B1 | 4/2007 | Dalbec et al. |
| 7,211,083 | B2 | 5/2007 | Chornenky et al. |
| 7,255,693 | B1 | 8/2007 | Johnston et al. |
| 7,264,002 | B2 | 9/2007 | Danek et al. |
| 7,273,055 | B2 | 9/2007 | Danek et al. |
| 7,344,533 | B2 | 3/2008 | Pearson et al. |
| 7,412,284 | B2 | 8/2008 | Hofmann |
| 7,412,285 | B2 | 8/2008 | Schroeppel et al. |
| 7,425,212 | B1 | 9/2008 | Danek et al. |
| 7,542,802 | B2 | 6/2009 | Danek et al. |
| 7,556,624 | B2 | 7/2009 | Laufer et al. |
| 7,594,925 | B2 | 9/2009 | Danek et al. |
| 7,620,451 | B2 | 11/2009 | Demarais et al. |
| 7,655,004 | B2 | 2/2010 | Long |
| 7,680,543 | B2 | 3/2010 | Azure |
| 7,708,768 | B2 | 5/2010 | Danek et al. |
| 7,722,606 | B2 | 5/2010 | Azure |
| 7,740,017 | B2 | 6/2010 | Danek et al. |
| 7,756,583 | B2 | 7/2010 | Demarais et al. |
| 7,770,584 | B2 | 8/2010 | Danek et al. |
| 7,819,908 | B2 | 10/2010 | Ingenito |
| 7,824,870 | B2 | 11/2010 | Kovalcheck et al. |
| 7,837,679 | B2 | 11/2010 | Biggs et al. |
| RE42,016 | E | 12/2010 | Chornenky et al. |
| 7,853,331 | B2 | 12/2010 | Kaplan et al. |
| 7,853,333 | B2 | 12/2010 | Demarais |
| 7,854,734 | B2 | 12/2010 | Biggs et al. |
| 7,906,124 | B2 | 3/2011 | Laufer et al. |
| RE42,277 | E | 4/2011 | Jaafar et al. |
| 7,921,855 | B2 | 4/2011 | Danek et al. |
| 7,931,647 | B2 | 4/2011 | Wizeman et al. |
| 7,937,143 | B2 | 5/2011 | Demarais et al. |
| 7,938,123 | B2 | 5/2011 | Danek et al. |
| 7,938,824 | B2 | 5/2011 | Chornenky et al. |
| 7,949,407 | B2 | 5/2011 | Kaplan et al. |
| 7,992,572 | B2 | 8/2011 | Danek et al. |
| 8,007,496 | B2 | 8/2011 | Rioux et al. |
| RE42,835 | E | 10/2011 | Chornenky et al. |
| 8,048,067 | B2 | 11/2011 | Davalos et al. |
| RE43,009 | E | 12/2011 | Chornenky et al. |
| 8,109,926 | B2 | 2/2012 | Azure |
| 8,114,070 | B2 | 2/2012 | Rubinsky et al. |
| 8,120,207 | B2 | 2/2012 | Sanders et al. |
| 8,131,371 | B2 | 3/2012 | Demarais et al. |
| 8,145,316 | B2 | 3/2012 | Deem et al. |
| 8,145,317 | B2 | 3/2012 | Demarais et al. |
| 8,150,519 | B2 | 4/2012 | Demarais et al. |
| 8,150,520 | B2 | 4/2012 | Demarais et al. |
| 8,161,978 | B2 | 4/2012 | Danek et al. |
| 8,181,656 | B2 | 5/2012 | Danek et al. |
| 8,221,411 | B2 | 7/2012 | Francischelli et al. |
| 8,231,603 | B2 | 7/2012 | Hobbs et al. |
| 8,235,983 | B2 | 8/2012 | Webster et al. |
| 8,251,070 | B2 | 8/2012 | Danek et al. |
| 8,251,986 | B2 | 8/2012 | Chornenky et al. |
| 8,257,413 | B2 | 9/2012 | Danek et al. |
| 8,267,094 | B2 | 9/2012 | Danek et al. |
| 8,282,631 | B2 | 10/2012 | Davalos et al. |
| 8,292,882 | B2 | 10/2012 | Danek et al. |
| 8,298,222 | B2 | 10/2012 | Rubinsky et al. |
| 8,298,224 | B2 | 10/2012 | Danek et al. |
| 8,425,505 | B2 | 4/2013 | Long |
| 8,443,810 | B2 | 5/2013 | Danek et al. |
| 8,449,538 | B2 | 5/2013 | Long |
| 8,459,268 | B2 | 6/2013 | Danek et al. |
| 8,464,723 | B2 | 6/2013 | Danek et al. |
| 8,465,484 | B2 | 6/2013 | Davalos et al. |
| 8,465,486 | B2 | 6/2013 | Danek et al. |
| 8,480,667 | B2 | 7/2013 | Kaplan et al. |
| 8,504,147 | B2 | 8/2013 | Deem et al. |
| 8,512,334 | B2 | 8/2013 | Nuccitelli et al. |
| 8,521,274 | B2 | 8/2013 | Gutsol et al. |
| 8,534,291 | B2 | 9/2013 | Danek et al. |
| 8,540,710 | B2 | 9/2013 | Johnson et al. |
| 8,562,588 | B2 | 10/2013 | Hobbs et al. |
| 8,568,403 | B2 | 10/2013 | Soltesz et al. |
| 8,579,888 | B2 | 11/2013 | Hoey et al. |
| 8,584,681 | B2 | 11/2013 | Danek et al. |
| 8,603,087 | B2 | 12/2013 | Rubinsky et al. |
| 8,620,423 | B2 | 12/2013 | Demarais et al. |
| 8,632,534 | B2 | 1/2014 | Pearson et al. |
| 8,636,726 | B1 | 1/2014 | Wells et al. |
| 8,640,711 | B2 | 2/2014 | Danek et al. |

(56) References Cited

U.S. PATENT DOCUMENTS

| | | |
|---|---|---|
| 8,647,338 B2 | 2/2014 | Chornenky et al. |
| 8,652,130 B2 | 2/2014 | Kreindel |
| 8,676,309 B2 | 3/2014 | Deem et al. |
| 8,721,632 B2 | 5/2014 | Hoey et al. |
| 8,733,367 B2 | 5/2014 | Danek et al. |
| 8,740,895 B2 | 6/2014 | Mayse et al. |
| 8,753,335 B2 | 6/2014 | Moshe et al. |
| 8,774,922 B2 | 7/2014 | Zarins et al. |
| 8,777,943 B2 | 7/2014 | Mayse et al. |
| 8,828,945 B2 | 9/2014 | Laufer et al. |
| 8,888,769 B2 | 11/2014 | Biggs et al. |
| 8,903,488 B2 | 12/2014 | Callas et al. |
| 8,906,006 B2 | 12/2014 | Chornenky et al. |
| 8,911,430 B2 | 12/2014 | Hoey et al. |
| 8,911,439 B2 | 12/2014 | Mayse et al. |
| 8,920,413 B2 | 12/2014 | Danek et al. |
| 8,926,606 B2 | 1/2015 | Davalos et al. |
| 8,944,071 B2 | 2/2015 | Loomas et al. |
| 8,992,513 B2 | 3/2015 | Delaney |
| 8,992,517 B2 | 3/2015 | Davalos et al. |
| 9,005,189 B2 | 4/2015 | Davalos et al. |
| 9,017,324 B2 | 4/2015 | Mayse et al. |
| 9,027,564 B2 | 5/2015 | Danek et al. |
| 9,033,976 B2 | 5/2015 | Danek et al. |
| 9,078,665 B2 | 7/2015 | Moss et al. |
| 9,095,323 B2 | 8/2015 | Chu et al. |
| 9,101,764 B2 | 8/2015 | Nuccitelli et al. |
| 9,108,052 B2 | 8/2015 | Jarrard |
| 9,125,666 B2 | 9/2015 | Steinke et al. |
| 9,144,449 B2 | 9/2015 | Burr et al. |
| 9,173,704 B2 | 11/2015 | Hobbs et al. |
| 9,198,733 B2 | 12/2015 | Neal, II et al. |
| 9,199,091 B2 | 12/2015 | Danek et al. |
| 9,259,235 B2 | 2/2016 | Chierchia et al. |
| 9,265,563 B2 | 2/2016 | Racz et al. |
| 9,272,132 B2 | 3/2016 | Laufer et al. |
| 9,277,957 B2 | 3/2016 | Long et al. |
| 9,283,374 B2 | 3/2016 | Hollett et al. |
| 9,289,606 B2 | 3/2016 | Paul et al. |
| 9,295,516 B2 | 3/2016 | Pearson et al. |
| 9,301,796 B2 | 4/2016 | Burr et al. |
| 9,308,043 B2 | 4/2016 | Zarins et al. |
| 9,308,044 B2 | 4/2016 | Zarins et al. |
| 9,314,620 B2* | 4/2016 | Long ............. A61B 18/1206 |
| 9,327,122 B2 | 5/2016 | Zarins et al. |
| 9,339,328 B2 | 5/2016 | Ortiz et al. |
| 9,339,618 B2 | 5/2016 | Deem et al. |
| 9,358,024 B2 | 6/2016 | Danek et al. |
| 9,375,268 B2 | 6/2016 | Long |
| 9,414,881 B2 | 8/2016 | Callas et al. |
| 9,439,726 B2 | 9/2016 | Zarins et al. |
| 9,486,266 B2 | 11/2016 | Soltesz et al. |
| 9,510,888 B2 | 12/2016 | Lalonde |
| 9,526,568 B2 | 12/2016 | Ohri et al. |
| 9,572,619 B2 | 2/2017 | Laufer et al. |
| 9,598,691 B2 | 3/2017 | Davalos |
| 9,649,153 B2 | 5/2017 | Mayse et al. |
| 9,649,154 B2 | 5/2017 | Mayse et al. |
| 9,656,055 B2 | 5/2017 | Weissberg et al. |
| 9,668,809 B2 | 6/2017 | Mayse et al. |
| 9,675,406 B2 | 6/2017 | Moss et al. |
| 9,675,412 B2 | 6/2017 | Mayse et al. |
| 9,681,909 B2 | 6/2017 | Bhargav et al. |
| 9,700,368 B2 | 7/2017 | Callas et al. |
| 9,717,552 B2* | 8/2017 | Cosman ............. A61B 18/1482 |
| 9,789,331 B2 | 10/2017 | Danek et al. |
| 9,820,797 B2 | 11/2017 | Burr et al. |
| 9,867,648 B2 | 1/2018 | Mulcahey et al. |
| 9,867,652 B2 | 1/2018 | Sano et al. |
| 9,888,956 B2 | 2/2018 | Model et al. |
| 9,895,189 B2 | 2/2018 | Pearson |
| 9,931,161 B2 | 4/2018 | Willis |
| 9,931,163 B2 | 4/2018 | Danek et al. |
| 9,956,391 B2 | 5/2018 | Weissberg et al. |
| 9,974,609 B2 | 5/2018 | Hollett et al. |
| 9,987,081 B1 | 6/2018 | Bowers et al. |
| 9,993,296 B2 | 6/2018 | Ladtkow et al. |
| 9,999,465 B2 | 6/2018 | Long et al. |
| 10,010,666 B2 | 7/2018 | Rubinsky et al. |
| 10,016,232 B1 | 7/2018 | Bowers et al. |
| 10,130,423 B1 | 11/2018 | Viswanathan et al. |
| 10,149,714 B2 | 12/2018 | Mayse et al. |
| 10,172,673 B2 | 1/2019 | Viswanathan et al. |
| 10,238,447 B2 | 3/2019 | Neal, II et al. |
| 10,245,105 B2 | 4/2019 | Davalos et al. |
| 10,271,893 B2 | 4/2019 | Stewart et al. |
| 2002/0104318 A1 | 8/2002 | Jaafar et al. |
| 2004/0047855 A1 | 3/2004 | Ingenito |
| 2005/0010270 A1 | 1/2005 | Laufer |
| 2005/0049542 A1 | 3/2005 | Sigg et al. |
| 2005/0171523 A1 | 8/2005 | Rubinsky et al. |
| 2005/0171574 A1 | 8/2005 | Rubinsky et al. |
| 2005/0288730 A1 | 12/2005 | Deem et al. |
| 2006/0293725 A1 | 12/2006 | Rubinsky et al. |
| 2006/0293731 A1 | 12/2006 | Rubinsky et al. |
| 2007/0083239 A1 | 4/2007 | Demarais et al. |
| 2007/0093802 A1 | 4/2007 | Danek et al. |
| 2007/0106296 A1 | 5/2007 | Laufer et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0156135 A1 | 7/2007 | Rubinsky et al. |
| 2008/0015571 A1 | 1/2008 | Rubinsky et al. |
| 2008/0132884 A1 | 6/2008 | Rubinsky et al. |
| 2008/0132885 A1 | 6/2008 | Rubinsky et al. |
| 2008/0200912 A1 | 8/2008 | Long |
| 2008/0269586 A1 | 10/2008 | Rubinsky et al. |
| 2009/0043301 A1 | 2/2009 | Jarrard et al. |
| 2009/0069797 A1 | 3/2009 | Danek et al. |
| 2009/0157002 A1 | 6/2009 | Dumot et al. |
| 2009/0192504 A1 | 7/2009 | Askew |
| 2009/0192505 A1 | 7/2009 | Askew et al. |
| 2009/0192508 A1 | 7/2009 | Laufer et al. |
| 2009/0247933 A1 | 10/2009 | Maor et al. |
| 2009/0281477 A1 | 11/2009 | Mikus et al. |
| 2010/0004623 A1 | 1/2010 | Hamilton, Jr. et al. |
| 2010/0130975 A1 | 5/2010 | Long |
| 2010/0152725 A1 | 6/2010 | Pearson et al. |
| 2010/0160906 A1 | 6/2010 | Jarrard |
| 2010/0204688 A1 | 8/2010 | Hoey et al. |
| 2010/0240995 A1 | 9/2010 | Nuccitelli et al. |
| 2010/0256628 A1 | 10/2010 | Pearson et al. |
| 2010/0256630 A1 | 10/2010 | Hamilton, Jr. et al. |
| 2010/0274236 A1 | 10/2010 | Krimsky |
| 2011/0112527 A1 | 5/2011 | Hamilton, Jr. et al. |
| 2011/0166565 A1 | 7/2011 | Wizeman et al. |
| 2011/0196288 A1 | 8/2011 | Kaplan et al. |
| 2011/0208166 A1 | 8/2011 | Dumot et al. |
| 2012/0109122 A1 | 5/2012 | Arena et al. |
| 2012/0220998 A1* | 8/2012 | Long ............. A61B 18/1206 606/41 |
| 2012/0277741 A1 | 11/2012 | Davalos et al. |
| 2012/0330299 A1 | 12/2012 | Webster et al. |
| 2013/0023873 A1 | 1/2013 | Danek et al. |
| 2013/0030425 A1 | 1/2013 | Stewart et al. |
| 2013/0030430 A1 | 1/2013 | Stewart et al. |
| 2013/0035747 A1 | 2/2013 | Danek et al. |
| 2013/0184702 A1 | 7/2013 | Neal, II et al. |
| 2013/0196441 A1 | 8/2013 | Rubinsky et al. |
| 2013/0211402 A1 | 8/2013 | Danek et al. |
| 2013/0218158 A1 | 8/2013 | Danek et al. |
| 2013/0226167 A1 | 8/2013 | Kaplan et al. |
| 2013/0253415 A1 | 9/2013 | Sano et al. |
| 2013/0261389 A1 | 10/2013 | Long |
| 2013/0261683 A1 | 10/2013 | Soikum et al. |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |
| 2014/0039489 A1 | 2/2014 | Davalos et al. |
| 2014/0039491 A1 | 2/2014 | Bakos et al. |
| 2014/0046322 A1 | 2/2014 | Callas et al. |
| 2014/0052126 A1 | 2/2014 | Long et al. |

(56) References Cited

U.S. PATENT DOCUMENTS

| | | |
|---|---|---|
| 2014/0074078 A1 | 3/2014 | Kumar et al. |
| 2014/0114378 A1 | 4/2014 | Danek et al. |
| 2014/0121663 A1 | 5/2014 | Pearson et al. |
| 2014/0128949 A1 | 5/2014 | Hollett et al. |
| 2014/0148635 A1 | 5/2014 | Danek et al. |
| 2014/0296844 A1 | 10/2014 | Kevin et al. |
| 2014/0324037 A1 | 10/2014 | Hoey et al. |
| 2014/0330332 A1 | 11/2014 | Danek et al. |
| 2014/0341801 A1 | 11/2014 | Laufer et al. |
| 2014/0378964 A1 | 12/2014 | Pearson |
| 2015/0025605 A1 | 1/2015 | Kaplan et al. |
| 2015/0038959 A1 | 2/2015 | Biggs et al. |
| 2015/0045788 A1* | 2/2015 | Litscher ............ A61B 18/1492 606/41 |
| 2015/0066005 A1 | 3/2015 | Fan et al. |
| 2015/0080884 A1 | 3/2015 | Zarins et al. |
| 2015/0088120 A1 | 3/2015 | Garcia et al. |
| 2015/0105775 A1 | 4/2015 | Wizeman et al. |
| 2015/0119879 A1 | 4/2015 | Jameson et al. |
| 2015/0141984 A1 | 5/2015 | Loomas et al. |
| 2015/0164584 A1 | 6/2015 | Davalos et al. |
| 2015/0173943 A1 | 6/2015 | Loomas et al. |
| 2015/0182560 A1 | 7/2015 | Calle et al. |
| 2015/0201996 A1 | 7/2015 | Rubinsky et al. |
| 2015/0223879 A1 | 8/2015 | Danek et al. |
| 2015/0230855 A1 | 8/2015 | Chornenky et al. |
| 2015/0305794 A1 | 10/2015 | Danek et al. |
| 2015/0313664 A1 | 11/2015 | Jarrard |
| 2015/0320479 A1* | 11/2015 | Cosman, Jr. ........... A61B 90/37 606/35 |
| 2015/0320999 A1 | 11/2015 | Nuccitelli et al. |
| 2015/0327944 A1 | 11/2015 | Neal, II et al. |
| 2015/0342669 A1 | 12/2015 | Flanagan et al. |
| 2016/0008066 A1 | 1/2016 | Kaplan et al. |
| 2016/0038230 A1 | 2/2016 | Danek et al. |
| 2016/0058493 A1 | 3/2016 | Neal, II et al. |
| 2016/0066977 A1 | 3/2016 | Neal, II et al. |
| 2016/0066990 A1 | 3/2016 | Kaplan et al. |
| 2016/0081745 A1 | 3/2016 | Rajagopalan et al. |
| 2016/0113703 A1 | 4/2016 | Danek et al. |
| 2016/0235974 A1 | 8/2016 | Holochwost et al. |
| 2016/0287314 A1 | 10/2016 | Arena et al. |
| 2016/0310211 A1 | 10/2016 | Long |
| 2016/0324573 A1 | 11/2016 | Mickelson et al. |
| 2016/0331441 A1 | 11/2016 | Konings |
| 2016/0354142 A1 | 12/2016 | Pearson et al. |
| 2016/0361109 A1 | 12/2016 | Weaver et al. |
| 2017/0000584 A1 | 1/2017 | Blanco et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0117603 A1 | 4/2017 | Kreis et al. |
| 2017/0156783 A1 | 6/2017 | McKernon et al. |
| 2017/0189097 A1 | 7/2017 | Viswanathan et al. |
| 2017/0189579 A1 | 7/2017 | Davalos et al. |
| 2017/0215953 A1 | 8/2017 | Long et al. |
| 2017/0216353 A1 | 8/2017 | Nuccitelli et al. |
| 2017/0239480 A1 | 8/2017 | Zarins et al. |
| 2017/0246455 A1 | 8/2017 | Athos et al. |
| 2017/0266438 A1 | 9/2017 | Sano et al. |
| 2017/0311789 A1 | 11/2017 | Mulcahey et al. |
| 2017/0319851 A1 | 11/2017 | Athos et al. |
| 2017/0325894 A1 | 11/2017 | Krimsky |
| 2017/0326361 A1 | 11/2017 | Kreis et al. |
| 2017/0333104 A1 | 11/2017 | Forde et al. |
| 2017/0333109 A1 | 11/2017 | Gilbert |
| 2017/0333112 A1 | 11/2017 | Nuccitelli et al. |
| 2018/0001056 A1 | 1/2018 | Leeflang et al. |
| 2018/0014868 A1 | 1/2018 | O'Connor et al. |
| 2018/0028250 A1 | 2/2018 | O'Connor |
| 2018/0036058 A1 | 2/2018 | Fan et al. |
| 2018/0042655 A1 | 2/2018 | Burr et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0071014 A1 | 3/2018 | Neal et al. |
| 2018/0078755 A1 | 3/2018 | Kreis et al. |
| 2018/0085160 A1 | 3/2018 | Viswanathan et al. |
| 2018/0132922 A1 | 3/2018 | Neal, II |
| 2018/0125565 A1 | 5/2018 | Sano et al. |
| 2018/0311497 A1 | 11/2018 | Viswanathan et al. |
| 2019/0069950 A1 | 3/2019 | Viswanathan et al. |
| 2019/0083169 A1 | 3/2019 | Single et al. |
| 2019/0151015 A1 | 5/2019 | Viswanathan et al. |
| 2019/0201089 A1 | 7/2019 | Waldstreicher et al. |

FOREIGN PATENT DOCUMENTS

| | | |
|---|---|---|
| AU | 2004235684 A1 | 1/2005 |
| AU | 2015355241 A1 | 6/2017 |
| AU | 2016246145 A1 | 10/2017 |
| CA | 2 370 223 A1 | 10/2000 |
| CA | 2 981 867 A1 | 10/2016 |
| CN | 102421386 A | 4/2012 |
| CN | 105939686 A | 9/2016 |
| CN | 108024803 A | 5/2018 |
| CN | 108778172 A | 11/2018 |
| CN | 108778173 A | 11/2018 |
| CO | 2017010662 A2 | 3/2018 |
| DE | 60023283 T2 | 7/2006 |
| DK | 0987989 T3 | 10/2006 |
| EP | 1 173 103 B1 | 1/2002 |
| EP | 1 804 905 B1 | 7/2007 |
| EP | 2 170 198 B1 | 4/2010 |
| EP | 2 317 951 A1 | 5/2011 |
| EP | 2 413 833 A1 | 2/2012 |
| EP | 2 488 251 A2 | 8/2012 |
| EP | 2 642 937 A2 | 10/2013 |
| EP | 2 762 195 A2 | 8/2014 |
| EP | 2 736 432 B1 | 3/2016 |
| EP | 3 003 461 B1 | 4/2016 |
| EP | 2 661 236 B1 | 8/2016 |
| EP | 3091925 A1 | 11/2016 |
| EP | 3 113 605 A2 | 1/2017 |
| EP | 3142584 A1 | 3/2017 |
| EP | 3143124 A1 | 3/2017 |
| EP | 3154464 A1 | 4/2017 |
| EP | 3 226 794 A1 | 10/2017 |
| EP | 3 282 953 A1 | 2/2018 |
| EP | 3139997 B1 | 9/2018 |
| EP | 3399931 A1 | 11/2018 |
| EP | 3399933 A1 | 11/2018 |
| EP | 3154463 B1 | 3/2019 |
| EP | 3471631 A1 | 4/2019 |
| EP | 3091921 B1 | 6/2019 |
| EP | 3456278 A3 | 6/2019 |
| EP | 3495018 A1 | 6/2019 |
| EP | 3206613 B1 | 7/2019 |
| ES | 2 246 853 T3 | 3/2006 |
| ES | 2 361 460 T3 | 6/2011 |
| IN | 201747039456 | 1/2001 |
| IN | 2006/01622 P2 | 5/2007 |
| JP | 2002-541905 A | 12/2002 |
| JP | 4242436 B2 | 3/2009 |
| JP | 2011-519699 A | 7/2011 |
| JP | 2015-128596 A | 7/2015 |
| JP | 2016-195826 A | 11/2016 |
| PT | 987989 E | 11/2006 |
| WO | WO 00/62699 A2 | 10/2000 |
| WO | WO-2005065284 A2 | 7/2005 |
| WO | WO-2006052940 A2 | 5/2006 |
| WO | WO-2006116198 A2 | 11/2006 |
| WO | WO 2008/063195 A1 | 5/2008 |
| WO | WO 2009/009398 A1 | 1/2009 |
| WO | WO 2009/137819 A1 | 11/2009 |
| WO | WO 2010/014480 A1 | 2/2010 |
| WO | WO 2010/117806 A1 | 10/2010 |
| WO | WO 2011/047387 A2 | 4/2011 |
| WO | WO 2012/071526 A2 | 5/2012 |
| WO | WO 2014/197632 A2 | 12/2014 |
| WO | WO-2015103530 A1 | 7/2015 |
| WO | WO-2015103574 A1 | 7/2015 |

(56) References Cited

FOREIGN PATENT DOCUMENTS

| | | |
|---|---|---|
| WO | WO-2015192018 A1 | 12/2015 |
| WO | WO-2015192027 A1 | 12/2015 |
| WO | WO-2016060983 A1 | 4/2016 |
| WO | WO 2016/089781 A1 | 6/2016 |
| WO | WO 2016/164930 A1 | 10/2016 |
| WO | WO-2016180934 A1 | 11/2016 |
| WO | WO 2017/109261 A1 | 6/2017 |
| WO | WO-2017119934 A1 | 7/2017 |
| WO | WO-2017120169 A1 | 7/2017 |
| WO | WO 2017/151260 A1 | 9/2017 |
| WO | WO 2017/200954 A1 | 11/2017 |
| WO | WO 2017/201394 A1 | 11/2017 |
| WO | WO-2017218734 A1 | 12/2017 |
| WO | WO 2018/005511 A1 | 1/2018 |
| WO | WO-2018026985 A1 | 2/2018 |
| WO | WO 2018/187244 A2 | 10/2018 |
| WO | WO-2018200800 A1 | 11/2018 |
| WO | WO-2018201037 A1 | 11/2018 |
| WO | WO-2019055512 A1 | 3/2019 |

OTHER PUBLICATIONS

International Search Report and Written Opinion dated Mar. 13, 2019 for International Application No. PCT/US2018/067501, 14 pages.

International Search Report and Written Opinion dated Mar. 13, 2019 for International Application No. PCT/US2018/067504, 13 pages.

Arena, C. B. et al., *Comprehenisve Biomedical Physics*, A. Brahme, Ed., (2014), Ch. 10.13 Electroporation Therapy, pp. 269-287, http://dx.doi.org/10.1016/8978-0-444-53632-7.01016-9.

Bhonsle, S. et al., "Characterization of Irreversible Electroporation Ablation with a Validated Perfused Organ Model," J Vasc Intery Radiol, 27:1913-1922 (2016), and Appendix A—Supplemental Materials and Methods, 2 pages.

Campelo, S. et al., "An evaluation of irreversible electroporation thresholds in human prostate cancer and potential correlations to physiological measurements," APL Bioengineering, 1:016101 (2017), 10 pages, https://doi.org/10.1063/1.5005828.

Davalos, R. V. et al., "Implications and Considerations of Thermal Effects When Applying Irreversible Electroporation Tissue Ablation Therapy," The Prostate, Wiley Periodicals, Inc. (2015), 5 pages.

Garcia, P. A. et al., "An Experimental Investigation of Temperature Changes During Electroporation," Abstract, URSI General Assembly and Scientific Symposium, Istanbul, Turkey, Aug. 13-20, 2011, 4 pages.

Garcia, P. A. et al., "A Parametric Study Delineating Irreversible Electroporation from Thermal Damage Based on a Minimally Invasive Intracranial Procedure," BioMedical Engineering OnLine, 10:34 (2011), 22 pages, http://www.biomedical-engineering-online.com/content/10/1/34.

Garcia, P. A. et al., "Intracranial Nonthermal Irreversible Electroporation: In Vivo Analysis," J Membrane Biol, 236:127-136 (2010).

Garcia, P. A. et al., *Electroporation in Laboratory and Clinical Investigations*, Chapter 3, "Non-Thermal Irreversible Electroporation for Tissue Ablation," E. P. Spugnini and al Baldi (Eds.), 2010, 22 pages, ISBN 978-1-61668-327-6.

Neal, R. E. et al., *Bioelectrics*, Chapter 5.4: Clinical Implications of Irreversible Electroporation: Clinical and Preclinical Findings, H Akiyama and R Heller, Springer. (In Press), 10 pages.

Neal II, R. E. et al., "Treatment of breast cancer through the application of irreversible electroporation using a novel minimally invasive single needle electrode," Breast Cancer Res Treat., 123(1):295-301 (2010).

Neal II, R. E. et al., "Hepatic Epithelioid Hemangioendothelioma Treated With Irreversible Electroporation and Antibiotics," Journal of Clinical Oncology, 31 (2013), 5 pages, 10.1200/JCO.2012.44. 9736.

Neal II, R. E. et al., "Spectrum of imaging and characteristics for liver tumors treated with irreversible electroporation," J. Biomedical Science and Engineering, 5:813-818 (2012).

Neal II, R. E. et al., "Improved Local and Systemic Anti-Tumor Efficacy for Irreversible Electroporation in Immunocompetent versus Immunodeficient Mice," PLoS One 8(5): e64559 (2013), 10 pages, doi:10.1371/journal.pone.0064559.

Neal II, R. E. et al., "The Feasibility of Irreversible Electroporation for the Treatment of Breast Cancer and Other Heterogeneous Systems," Annals of Biomedical Engineering, 37(12):2615-2625 (2009).

Neal II, R. E. et al., "Experimental Characterization and Numerical Modeling of Tissue Electrical Conductivity during Pulsed Electric Fields for Irreversible Electroporation Treatment Planning," IEEE Transactions on Biomedical Engineering, 59(4):1076-1085 (2012).

Neal II, R. E. et al., "In Vitro and Numerical Support for Combinatorial Irreversible Electroporation and Electrochemotherapy Glioma Treatment," Annals of Biomedical Engineering, 42 (2013), 13 pages, doi:10.1007/s10439-013-0923-2.

Neal II, R. E. et al., "In Vivo Irreversible Electroporation Kidney Ablation: experimentally Correlated Numerical Models," IEEE Transactions on Biomedical Engineering (2013), 10 pages, doi:10.1109/TBME.2014.2360374.

Neal II, R. E. et al., "Successful Treatment of a Large Soft Tissue Sarcoma With Irreversible Electroporation," Journal of Clinical Oncology, 29(13):e372-e377 (2011), doi:10.1200/JCO.2010.33. 0902.

Neal II, R. E. et al., "An "Off-the-Shelf" System for Intraprocedural Electrical Current Evaluation and Monitoring of Irreversible Electroporation Therapy," Cardiovasc Intervent Radiol, 38(3):736-741 (2014).

Neal II, R. E. et al., "The Effects of Metallic Implants on Electroporation Therapies: Feasibility of Irreversible Electroporation for Brachytherapy Salvage," Cardiovasc Intervent Radiol, 36(6):1638-1645 (2013).

Neal II, R. E. et al., "In vivo Characterization and Numerical Simulation of Prostate Properties for Non-Thermal Irreversible Electroporation Ablation," The Prostate, 17(10):22760 (2014), 11 pages.

O'Brien, T. J. et al., "Effects of internal electrode cooling on irreversible electroporation using a perfused organ model," International Journal of Hyperthermia, 35(1):44-55 (2019).

Rossmeisl, J. H. et al., "Safety and feasibility of the NanoKnife system for irreversible electroporation ablative treatment of canine spontaneous intracranial gliomas," J Neurosurg, 123(4):1008-1025 (2015).

Sano, M. B. et al., "Towards the creation of decellularized organ constructs using irreversible electroporation and active mechanical perfusion," BioMedical Engineering OnLine, 9:83 (2010), 16 pages, http://www.biomedical-engineering-online.com/content/9/1/83.

Scheffer, H. J. et al., "The Influence of a Metal Stent on the Distribution of Thermal Energy during Irreversible Electroporation," PLoS One, 11(2): e0148457 (2016), 13 pages, doi:10.1371/journal.pone.0148457.

Schoenbach, K. H. et al., *Bioelectrics*, H. Akiyama, R. Heller, Eds., Springer (2017), ISBN 978-4-431-56093-7, ISBN 978-4-431-56095-1 (eBook), doi:10.1007/978-4-431-56095-1, 491 pages.

Thomson, K. R. et al., "Introduction to Irreversible Electroporation—Principles and Techniques," Techniques in Vascular and Interventional Radiology, 18(3):128-134 (2015).

Wandel, A. et al., "Optimizing Irreversible Electroporation Ablation with a Bipolar Electrode," J Vasc Radiol, 27:1441-1450 (2016).

Arena et al. High-frequency Irreversible Electroporation (H-FIRE) for Non-Thermal Ablation Without Muscle Contraction, Biomedical Engineering OnLine 2011, 10:102.

Cerveri, et al, Variations in the prevalence across countries of chronic bronchitis and smoking habits in young adults; Eur Respir J 2001; 18: 85-92.

Criner, G. Chronic Bronchitis: The Case for an Unmet Medical Need. ERS 2017, Milan, Italy.

Damian E. Dupuy, et al.; Irreversible Electroporation in a Swine Lung Model; Cardiovasc Intervent Radiol (2011) 34:391-395.

David A. Dean; Gene Electrotransfer to Lung; Springer Science+Business Media, LLC; 2011; Chapter 15; pp. 165-175.

FastStats—Chronic Lower Respiratory Disease. Centers for Disease Control (CDC) / National Center for Health Statistics (NCHS) 2017; https://www.cdc.gov/nchs/fastats/copd.htm.

(56) References Cited

OTHER PUBLICATIONS

Fernandez-Bussy et al. Histopathologic Results Post Bronchial Rheoplasty. ATS 2019, Dallas, TX.

Global Strategy for the Diagnosis, Management and Prevention of COPD, Global Initiative for Chronic Obstructive Lung Disease (GOLD) 2017. Available from: https://goldcopd.org.

Health at a Glance: Europe (2012 and 2014 reports) http://www.oecd-ilibrary.org/social-issues-migration-health/health-at-a-glance-europe-2012_9789264183896-en.

Hong Bae Kim, et al.; Physicochemical Factors That Affect Eelctroporation of Lung Cancer and Normal Cell Lines; Biochemical and Biophysical Research Communications; 2019; pp. 1-6.

Jason A. Tri, et al.; Electroporation Ablation of Bronchial Smooth Muscle Cells; A Novel Non-Thermal Asthma Therapy; Open Access Text; 2016; ISSN: 2398-3108; pp. 1-4.

Jens Ricke, et al.; Irreversible Electroporation (IRE) Fails to Demonstrate< span style="font-size: 12px;">Efficiencyin a Prospective Multicenter Phase II Trial on Lung Malignancies; The ALICE Trial; Cardiovasc Intervent Radiol; 2015; pp. 1-8.

Kim et al. The Chronic Bronchitic Phenotype of COPD: An analysis of the COPD Gene Study CHEST 2011; 140(3):626-633.

Michael B. Sano, et al.; Burst and Continuous High Frequency Irreversible Electroporation Protocols Evaluated in a 3D Tumor Model; Physics in Medicine & Biology; 2018; 63; pp. 1-18.

Peter S. Tang, et al.; Acute Lung Injury and Cell Death; How Many Ways Can Cells Die?; Am J. Physiol Lung Cell Mol Physiol; 294; 2008; pp. 1-10.

Tyler Miklovic, et al.; A Comprehensive Characterization of Parameters Affecting High- Frequency Irreversible Electroporation Lesions; Annals of Biomedical Engineering; 2017; pp. 1-11.

Valipour, A. et al. First-in-Human Results of Bronchial Rheoplasty: An endobronchial Treatment for Chronic Bronchitis. ATS 2019, Dallas, TX.

Vitalij Novickij, et al.; High Frequency Electroporation Efficiency is Under Control of Membrane Capacitive Charging and Voltage Potential Relaxation; Bioelectrochecmistry 2018; 119; pp. 92-97.

* cited by examiner

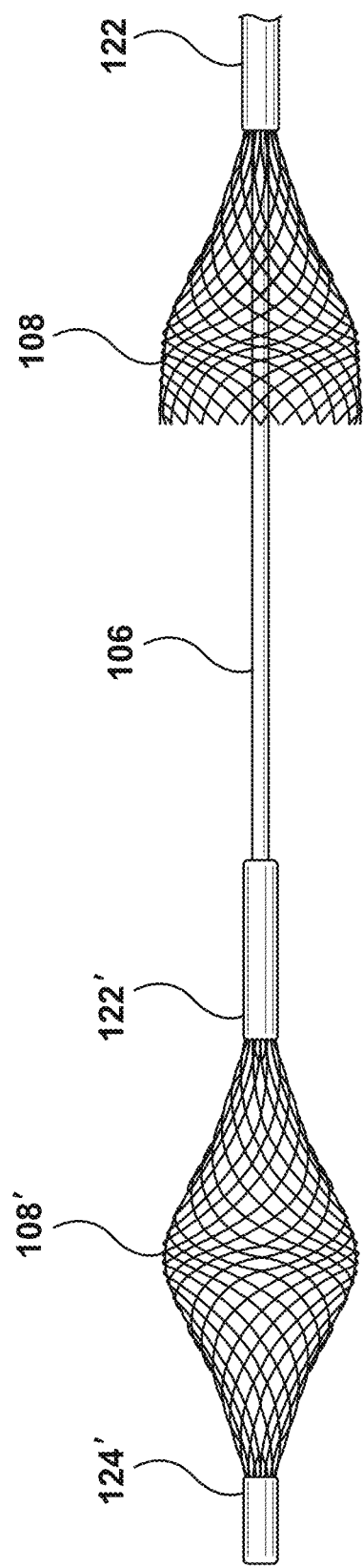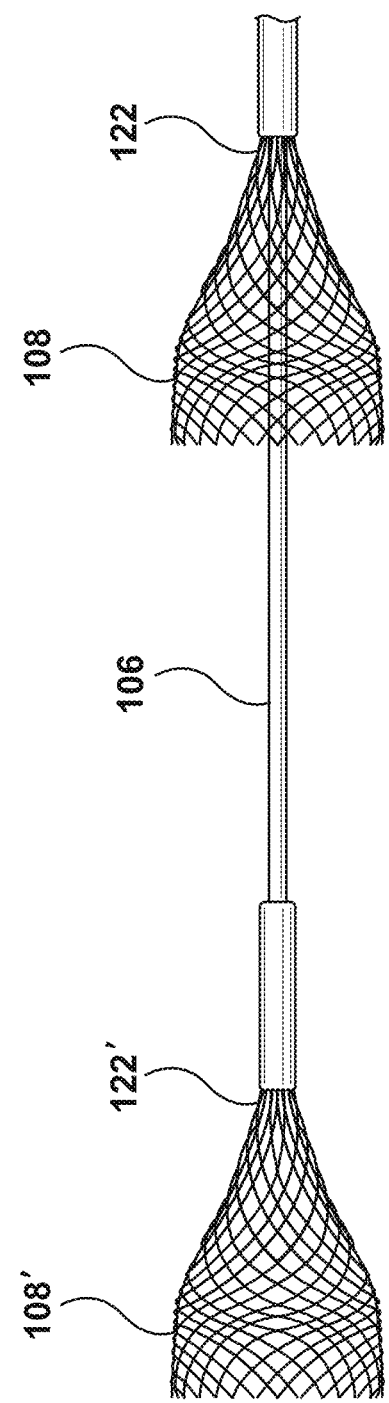
FIG. 28A
FIG. 28B

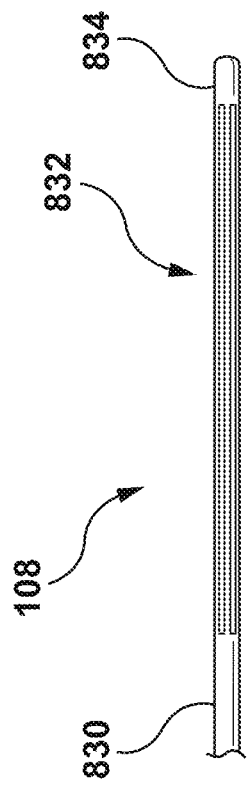
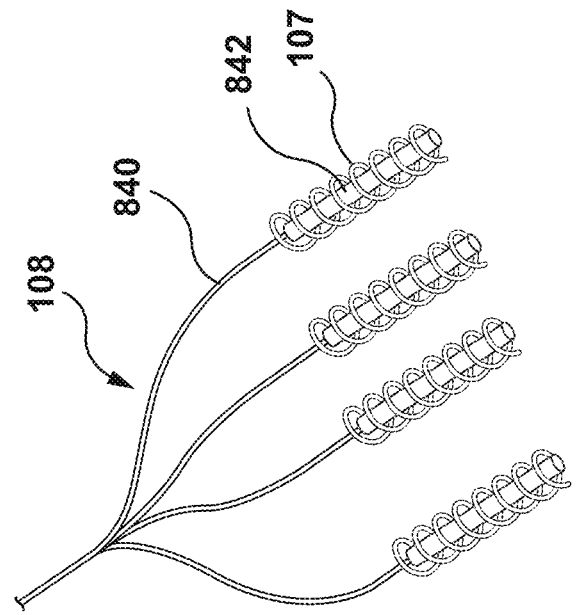
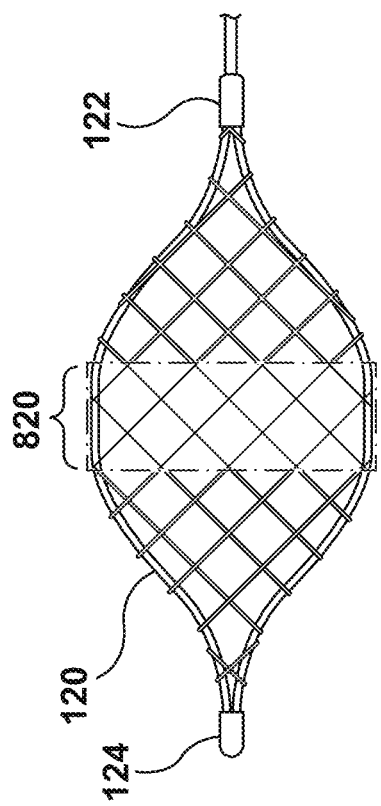
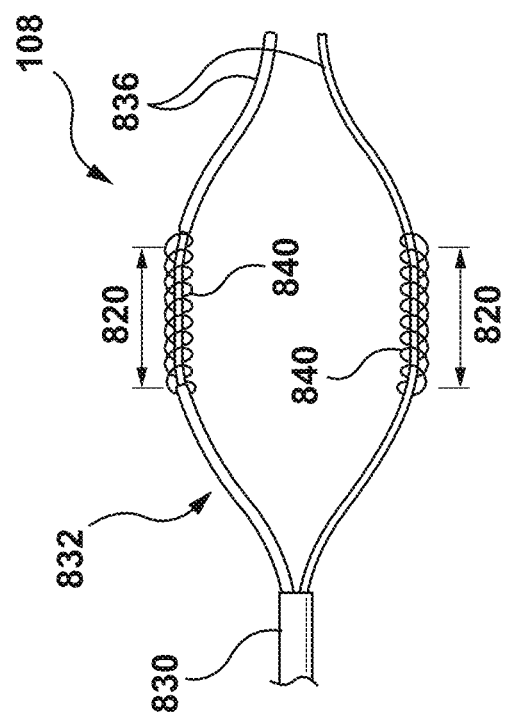

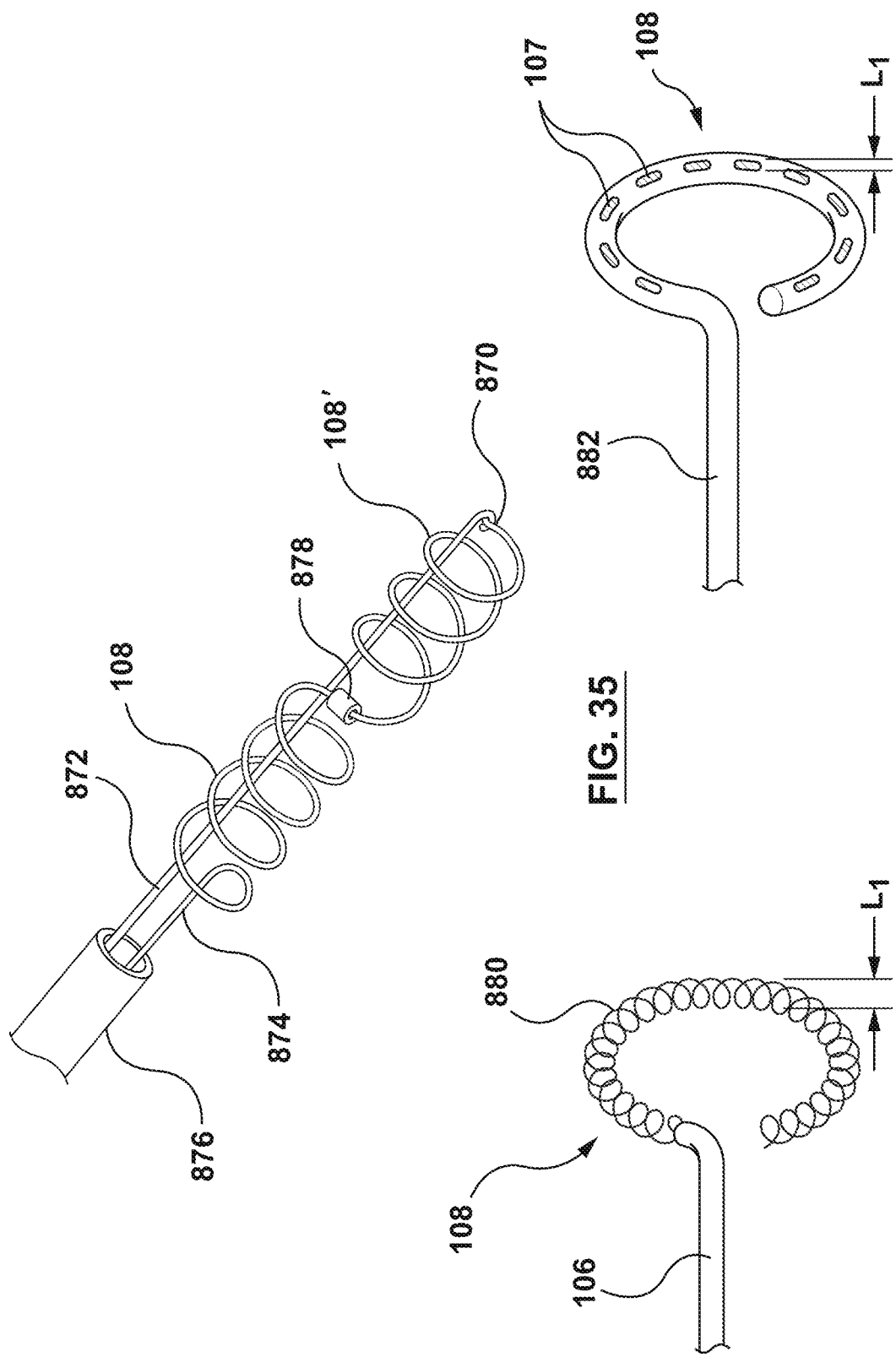

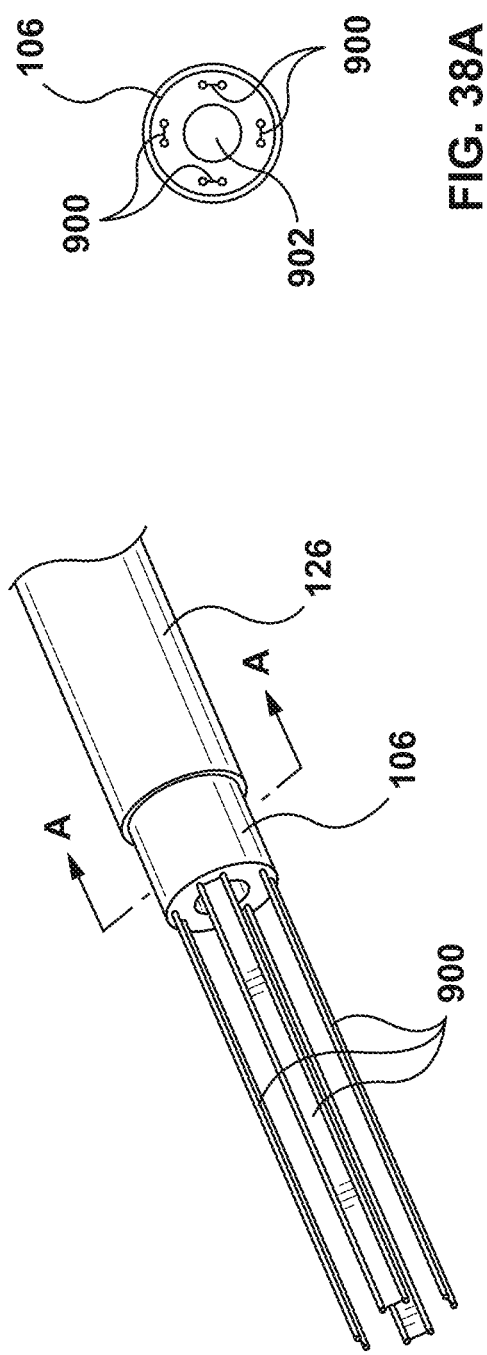
FIG. 38
FIG. 38A
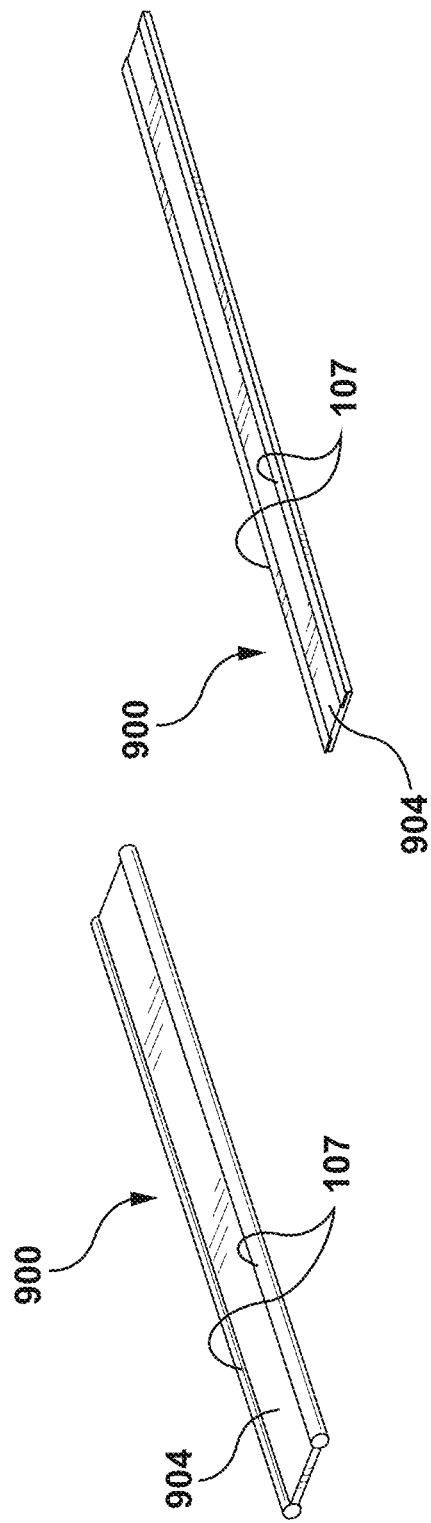
FIG. 39
FIG. 40

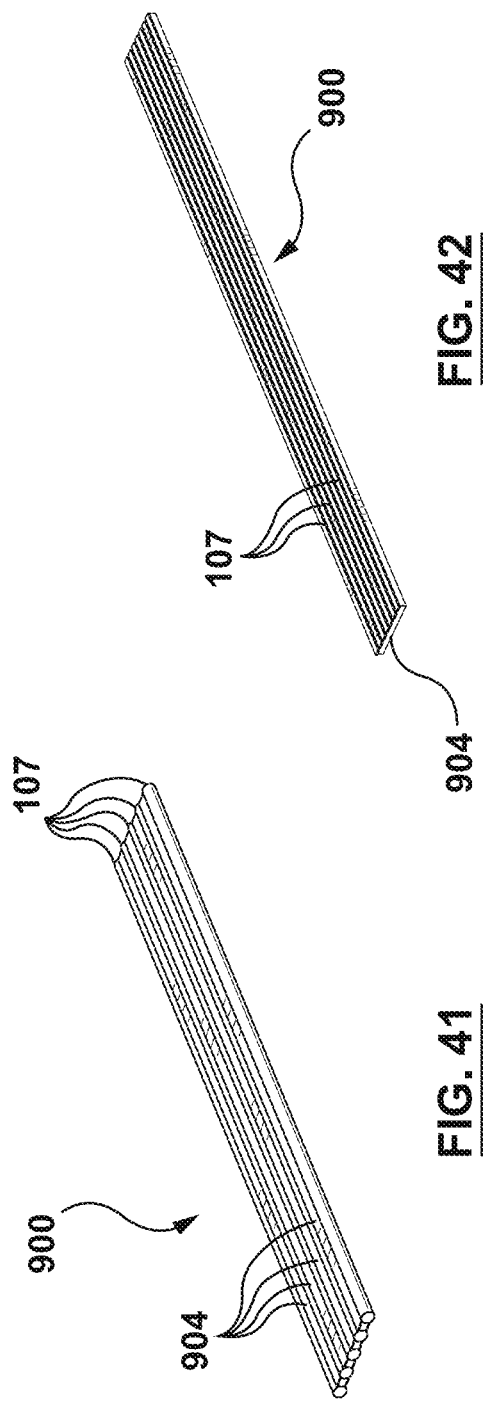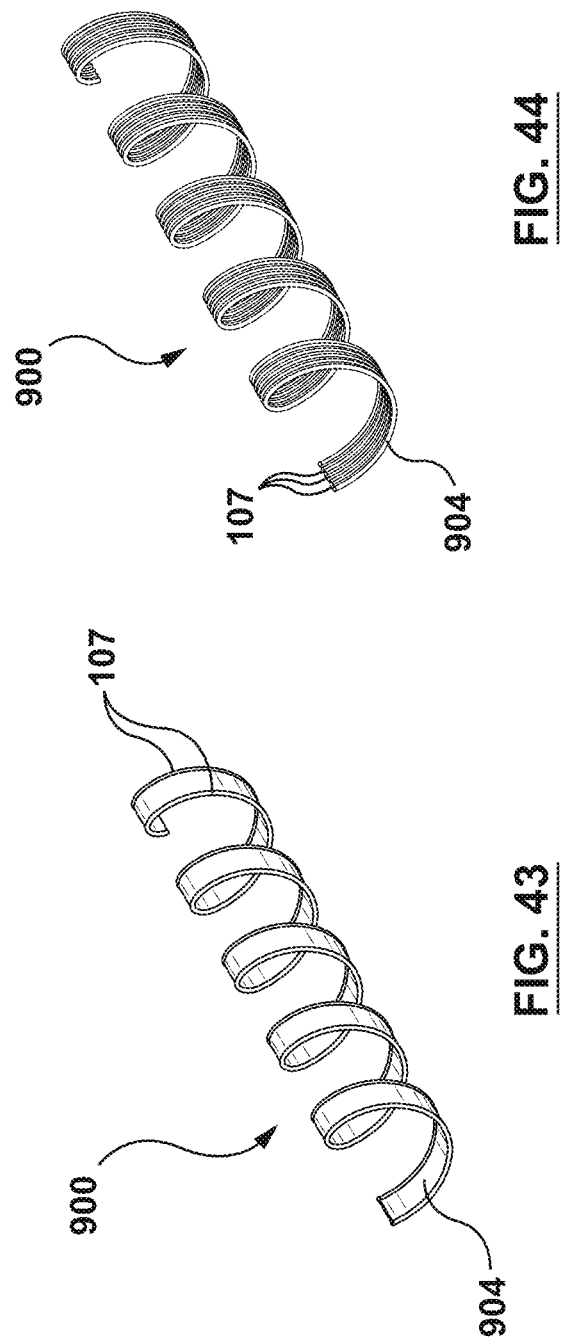

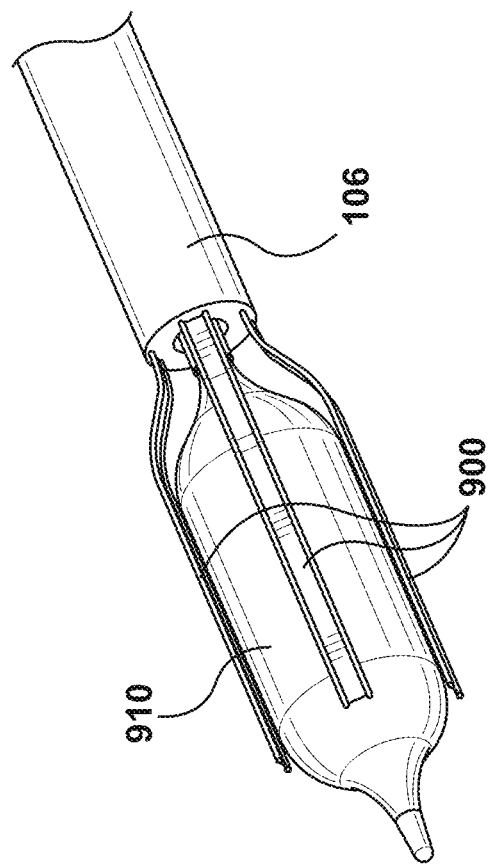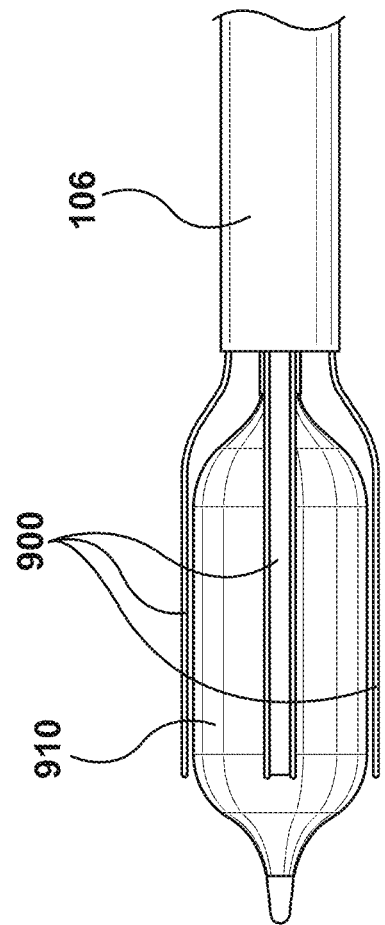

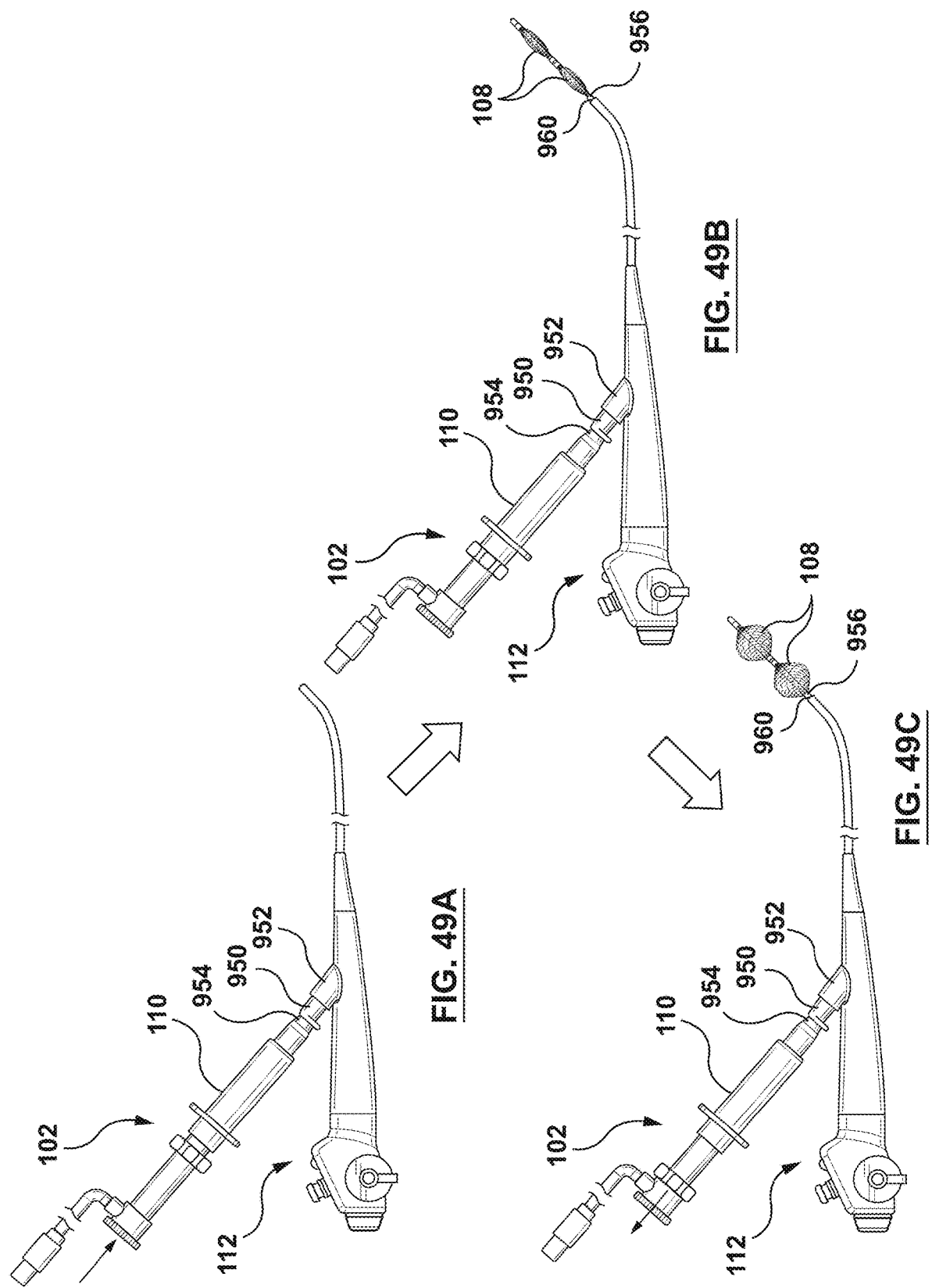

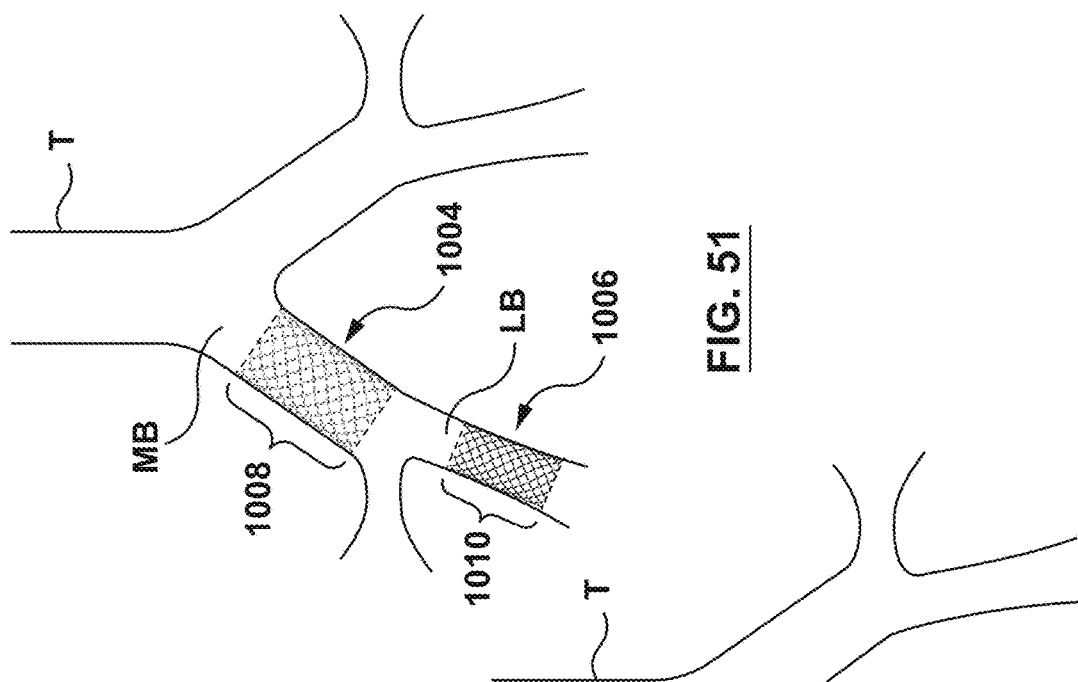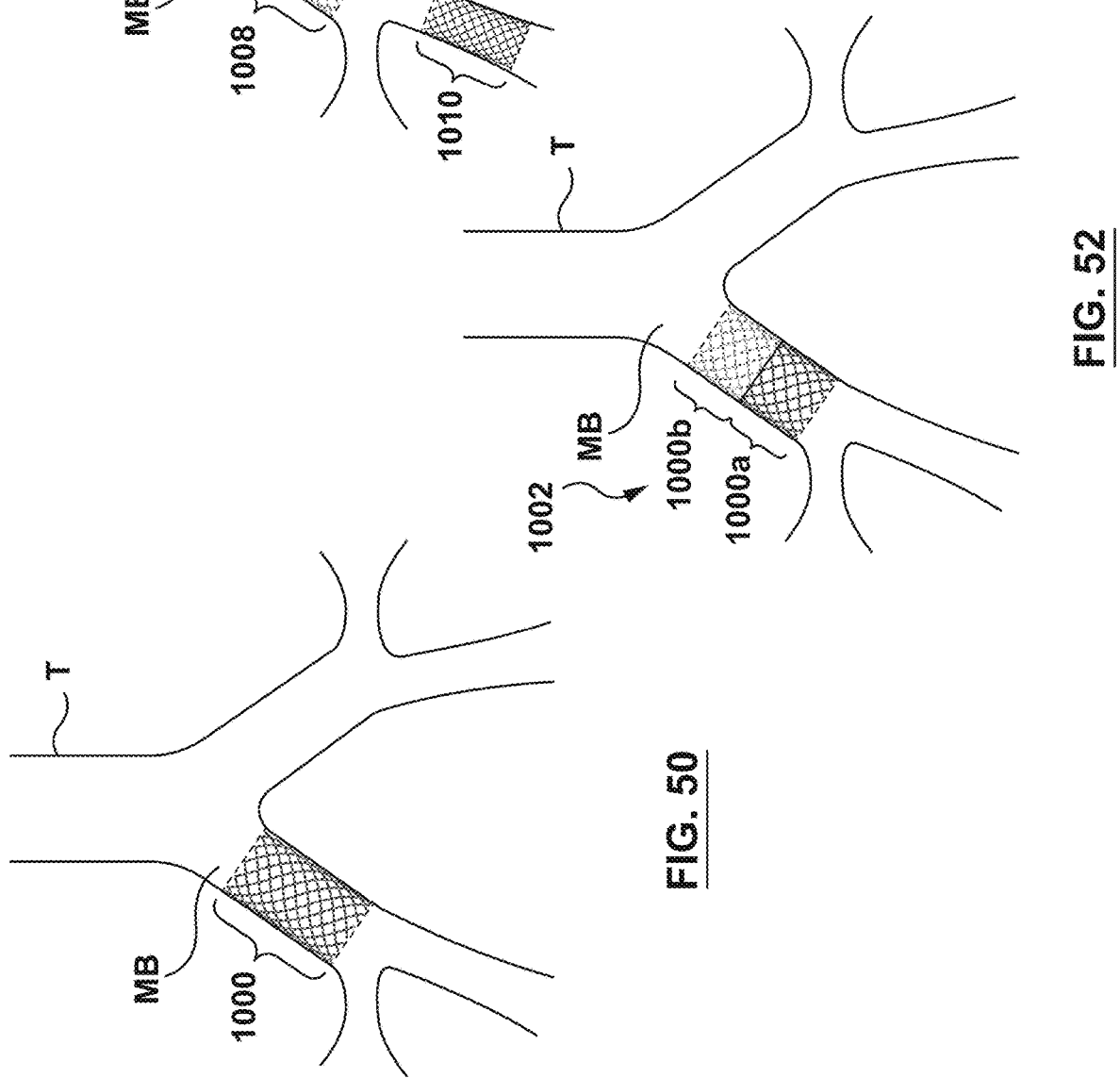

METHODS, APPARATUSES, AND SYSTEMS FOR THE TREATMENT OF PULMONARY DISORDERS

CROSS-REFERENCE TO RELATED APPLICATIONS

This application is a continuation of U.S. patent application Ser. No. 16/227,796, filed Dec. 20, 2018, entitled "Methods, Apparatuses, and Systems for the Treatment of Pulmonary Disorders," which is a continuation of International Patent Application No. PCT/US2017/039527, filed Jun. 27, 2017, entitled "Methods, Apparatuses, and Systems for the Treatment of Pulmonary Disorders," which claims priority to and the benefit of U.S. Patent Application No. 62/355,164, filed Jun. 27, 2016, entitled "Methods, Apparatuses, and Systems for the Treatment of Pulmonary Disorders" and U.S. Patent Application No. 62/489,753, filed Apr. 25, 2017, entitled "Methods, Apparatuses, and Systems for the Treatment of Pulmonary Disorders." The disclosures of the foregoing applications are incorporated herein by reference in their entireties.

BACKGROUND OF THE INVENTION

I. Anatomy

FIG. 1 provides an illustration of the pulmonary anatomy. Air travels down the trachea T and into the lungs L where the trachea T branches into a plurality of airways that extend throughout the lungs L. The trachea T first bifurcates into the right and left mainstem bronchi MB at the carina CA. These main bronchi MB further divide into the lobar bronchi LB, segmental bronchi SB, sub-segmental bronchi SSB, and terminate with the alveoli A. The diameters of the airways decrease as they bifurcate. The trachea T can have a luminal diameter ranging from about 15 mm to 22 mm, the mainstem bronchi MB can have a luminal diameter ranging from about 12 mm to 16 mm, the lobar bronchi LB can have a luminal diameter ranging from about 9 mm to 12 mm, and the diameter of subsequent bronchi continue to become smaller. The length of the airway also varies with each segment. In some patients, the trachea T has a length of about 12 cm, the mainstem bronchi MB has a length of about 4.8 cm, the lobar bronchi LB has a length of about 1.9 cm, and the length of subsequent bronchi continue to become shorter. In addition, the airway walls become thinner and have less supporting structure as they move more distally into the lung tissue.

The airways of the lung L are comprised of various layers, each with one or several types of cells. FIG. 2 illustrates a cross-sectional view representative of an airway wall W having a variety of layers and structures. The inner-most cellular layer of the airway wall W is the epithelium or epithelial layer E which includes pseudostratified columnar epithelial cells PCEC, goblet cells GC and basal cells BC. Goblet cells GC are responsible for the secretion of mucus M, which lines the inner wall of the airways forming a mucus blanket. The pseudostratified columnar epithelial cells PCEC include cilia C which extend into the mucus blanket. Cilia C that are attached to the epithelium E beat towards the nose and mouth, propelling mucus M up the airway in order for it to be expelled.

The basal cells BC attach to the basement membrane BM, and beneath the basement membrane BM resides the submucosal layer or lamina propria LP. The lamina propria LP includes a variety of different types of cells and tissue, such as smooth muscle SM. Smooth muscle is responsible for bronchoconstriction and bronchodilation. The lamina propria LP also include submucosal glands SG. Submucosal glands SG are responsible for much of the inflammatory response to pathogens and foreign material. Likewise, nerves N are present. Nerve branches of the vagus nerve are found on the outside of the airway walls or travel within the airway walls and innervate the mucus glands and airway smooth muscle, connective tissue, and various cell types including fibroblasts, lymphocytes, mast cells, in addition to many others. And finally, beneath the lamina propria LP resides the cartilaginous layer CL.

FIG. 3 provides a cross-sectional illustration of the epithelium E of an airway wall W showing types of cellular connections within the airway. Pseudostratified columnar epithelial cells PCEC and goblet cells GC are connected to each other by tight junctions TJ and adherens junctions AJ. The pseudostratified columnar epithelial cells PCEC and goblet cells GC are connected to the basal cells BC by desmosomes D. And, the basal cells BC are connected to the basement membrane BM by hemidesmosomes H.

II. Pulmonary Disorders

FIGS. 4A-4B depict bronchial airways B in healthy and diseased states, respectively. FIG. 4A illustrates a bronchial airway B in a healthy state wherein there is a normal amount of mucus M and no inflammation. FIG. 4B illustrates a bronchial airway B in a diseased state, such as chronic obstructive pulmonary disease, particularly chronic bronchitis. Chronic bronchitis is characterized by a persistent airflow obstruction, chronic cough, and sputum production for at least three months per year for two consecutive years. FIG. 4B illustrates both excess mucus M and inflammation I which leads to airway obstruction. The airway inflammation I is consistent with a thickened epithelial layer E.

A variety of pulmonary disorders and diseases lead to airway obstruction. A few of these disorders and diseases will be described briefly herein.

A. Chronic Obstructive Pulmonary Disease (COPD)

Chronic Obstructive Pulmonary Disease (COPD) is a common disease characterized by chronic irreversible airflow obstruction and persistent inflammation as a result of noxious environmental stimuli, such as cigarette smoke or other pollutants. COPD includes a range of diseases with chronic bronchitis primarily affecting the airways; whereas, emphysema affects the alveoli, the air sacs responsible for gas exchange. Some individuals have characteristics of both.

In chronic bronchitis, the airway structure and function is altered. In chronic bronchitis, noxious stimuli such as cigarette smoke or pollutants are inhaled and recognized as foreign by the airways, initiating an inflammatory cascade. Neutrophils, lymphocytes, macrophages, cytokines and other markers of inflammation are found in the airways of people with prolonged exposure, causing chronic inflammation and airway remodeling. Goblet cells can undergo hyperplasia, in which the cells increase in number, or hypertrophy, in which the goblet cells increase in size. Overall, the goblet cells produce more mucus as a response to the inflammatory stimulus and to remove the inhaled toxins. The excess mucus causes further airway luminal narrowing, leading to more obstruction. Cilia are damaged by the noxious stimuli, and therefore the excess mucus remains in the airway lumen, obstructing airflow from proximal to distal during inspiration, and from distal to proximal during the expiratory phase. Smooth muscle can become hypertrophic and thicker, causing bronchoconstriction. Submucosal glands can also become hyperplastic and hypertrophic, increasing the overall thickness of the airway wall and, which further constricting the diameter of the lumen.

In addition to a reduction in the luminal diameter of the airway, mucus hypersecretion can also lead to an exacerbation, or general worsening of health. As a consequence of the excess mucus and damaged cilia, pathogens such as bacteria (e.g., *Haemophilus influenzae, Streptococcus pneumoniae, Moraxella catarrhalis, Staphylococcus aureus, Pseudomonas aeruginosa, Burkholderia cepacia*, opportunistic gram-negatives, *Mycoplasma pneumoniae*, and *Chlamydia pneumoniae*), viruses (rhinoviruses, influenze/parainfluenza viruses, respiratory syncytial virus, coronaviruses, herpes simplex virus, adenoviruses), and other organisms (e.g., fungi) can flourish, causing an exacerbation, resulting in a set of symptoms. These include worsening cough, congestion, an increase in sputum quantity, a change in sputum quality, and/or shortness of breath. Treatment for an acute exacerbation can include oral or intravenous steroids, antibiotics, oxygen, endotracheal intubation and the need for mechanical ventilation via a ventilator.

B. Asthma

Asthma is a disease of the airways characterized by airway hyper-responsiveness. In asthma, the epithelium can be thickened, mucus hypersecretion can be present as a result of excess production from goblet cells and submucosal glands, and smooth muscle can be thickened. As discussed herein, mucus hypersecretion or excess mucus can allow pathogens to flourish, leading to an infection.

C. Interstitial Pulmonary Fibrosis

Interstitial pulmonary fibrosis is thought to be initiated with acute injury to the lung tissue that leads to chronic and aberrant inflammation. Fibroblasts are activated in response to the inflammation, which causes pulmonary fibrosis, scarring, and worsening lung function. Only 20 to 30% of patients are alive at five years after the diagnosis.

D. Cystic Fibrosis (CF)

Cystic Fibrosis (CF) is a systemic disease with pulmonary manifestations defined by a genetic defect, wherein the Cystic Fibrosis Transmembrane Conductance Regulator (CFTR) gene is mutated, leading to thickened secretions that cannot be expelled. Chronic inflammation leads to airway remodeling and hypersecretion via the goblet cells and submucosal glands, which lead to airway constriction and infections that are difficult to fully resolve.

D. Bronchiectasis

Bronchiectasis is a condition that leads to the airways to dilate, become thickened and scarred. It usually occurs due to an infection or other condition that injures the airway walls, prevents the airway from clearing mucus, or both. With this condition, the airways lose their ability to clear mucus, which can lead to repeated infections. Each infection causes additional damage, eventually leading to moderate airflow obstruction. Bronchiectasis can be caused by genetic disorders such as primary ciliary dyskinesia or can be of idiopathic origin.

III. Pulmonary Treatments

In some instances, the most effective treatment for a pulmonary disorder is a lifestyle change, particularly smoking cessation. This is particularly the case in COPD. However, many patients are unable or unwilling to cease smoking. A variety of treatments are currently available to reduce symptoms of pulmonary disorders.

A. Medication

COPD can be managed with one or several medications, such as Short Acting Beta Agonists (SABAs), Long Acting Beta Agonists (LABAs), Long Acting Muscarinic Antagonists (LAMAs), steroids, chronic antibiotic therapy, or PDE4 inhibitors such as Roflumilast. SABAs and LABAs act on the beta receptor of smooth muscle in the airway to cause bronchodilation. LAMAs act via anticholinergic pathways, inhibiting the release of acetylcholine causing bronchodilation. LABAs and LAMAs have been demonstrated to decrease breathlessness, reduce frequency of exacerbations and improve quality of life but have not been shown to decrease mortality. Tiotropium, a LAMA, can slow the rate of decline of lung function and increase the time until an exacerbation Inhaled corticosteroids directly target inflammation. Inhaled corticosteroids have been demonstrated to decrease exacerbations but have little effect on lung function and mortality. Combinations of LABAs, LAMAs and inhaled corticosteroid drugs have been formulated Inhaled oxygen is known to decrease breathlessness and improve mortality but these results are only associated with advanced disease represented by strict criteria and require chronic administration via nasal cannula or alternative apparatuses.

COPD can also be managed with one or several oral medications, such as PDE4 inhibitors, steroids, and antibiotics. Roflumilast is an oral medication that is a selective long acting inhibitor of the enzyme PDE4. It has very strong anti-inflammatory effects but is not well tolerated, with adverse effects including diarrhea, weight loss, nausea, decreased appetite and abdominal pain among others. Oral steroids such as prednisone can be prescribed to a patient in order to treat acute inflammation during an exacerbation. Patients have been known to continue on oral steroids for long periods of time if withdrawal leads to another exacerbation. Oral steroids have many side effects such as weight gain, insomnia, thyroid dysfunction, and osteoporosis, among others. Azithromycin or long term administration of antibiotics has been shown to reduce the frequency of COPD exacerbations. Antibiotics can achieve this via an antimicrobial effect by killing the pathogens responsible for the exacerbation or by other mechanisms such as a reduction in mucus secretion as has been shown with macrolide antibiotics. Side effects of long-term administration of antibiotics include hearing loss and antibiotic resistance.

Oftentimes patients are non-compliant with prescribed respiratory medications Inhaled therapies require deep inspiration as well as synchronization with inspiration, which many patients, especially the elderly, cannot perform. Patients can skip doses secondary to cost, experience side effects, or both. Together, all of these factors contribute to inadequate and inconsistent dosing.

Asthma can range in severity in adults, from mild disease to persistent. Milder disease can be adequately managed with trigger avoidance and Short Acting Beta Agonists (SABAs) whereas the mainstay of therapy for persistent asthma is inhaled glucocorticoids. Regular use of inhaled glucocorticoids has been shown in clinical trials to reduce the need for rescue inhalers, improve lung function, decrease symptoms, and prevent exacerbations. Some patients benefit from the addition of a leukotriene modifying agent or LABA. Tiotropium can be another option to improve lung function, more so than inhaled glucocorticoids alone. Very severe cases can require temporary or long term treatment with oral corticosteroids.

There is no known cure for interstitial pulmonary fibrosis (IPF). The mainstay of treatment is supplemental oxygen when required and preventive measures, such as vaccination. Pirfenidone is an anti-fibrotic agent that is approved for IPF, attempting to slow the fibroblast foci, collagen deposition and inflammatory cell infiltration of the disease. In clinical trials, Pirfenidone has been shown to reduce the decline in vital capacity (a measure of pulmonary function) and demonstrated a reduction in all-cause mortality. Nintedanib is another agent approved for IPF and acts via a receptor blocker for multiple tyrosine kinases that mediate elaboration of fibrogenic growth factors (e.g., platelet-derived growth factor, vascular endothelial growth factor, fibroblast growth factor). It appears to slow the rate of disease progression in IPF. No device therapy is approved for IPF.

Treatment for cystic fibrosis has rapidly evolved from chest physiotherapy and supplemental oxygen to therapies that target the underlying defect in the CFTR gene. Ivacaftor is a CFTR potentiator, improving the transport of chloride through the ion channel, which is FDA approved for several CFTR gene mutations. In clinical trials it has been shown to improve FEV1 and reduce the frequency of exacerbations. It also improves mucociliary and cough clearance. It does not, however, improve outcomes when used alone in patients with the most common delta F508 deletion. Other targeted therapies are in clinical trials. Chronic antibiotics are commonly prescribed for CF, including azithromycin, which likely has anti-inflammatory benefits, and inhaled tobramycin to treat Pseudomonas aeruginosa. As with other obstructive diseases, CF patients benefit from bronchodilators including LABAs and LAMAs. Agents to promote airway secretion clearance include inhaled DNase to decrease the viscosity of mucus, inhaled hypertonic saline to draw water from the airway in the mucus, and inhaled N-acetylcysteine that cleaves disulfide bonds within mucus glycoproteins. Guidelines recommend against chronic use of inhaled corticosteroids although oral steroids can be used in cases of exacerbations.

Bronchiectasis is the anatomic manifestation of a host injury response resulting in the excess dilatation of airway luminal caliber and thus therapy is often directed at the cause of the primary disease. These can be non-tuberculous mycobacteria infection, primary immunodeficiencies, allergic bronchopulmonary and aspergillosis among others. Treatment of acute exacerbation is focused on treating the offending bacterial pathogens with antibiotics. Macrolide and non-macrolide antibiotics have been shown to reduce the frequency of exacerbations. The use of inhaled antibiotics in the absence of CF is unclear as are the use of mucolytic agents. Bronchodilators can be used in patients with signs of airway obstruction on spirometry.

Primary Ciliary Dyskinesia (PCD) interventions aim to improve secretion clearance and reduce respiratory infections with daily chest physiotherapy and prompt treatment of respiratory infections. The role of nebulized DNase and other mucolytic drugs is less clear.

Respiratory tract infections caused by pathogens in the airway can occur with any of these maladies, and are typically treated with antibiotics. Unfortunately, drug development in this area is in decline and current therapies have significant limitations. One issue is that there is no one agent capable of treating the spectrum of pathogens found in these patients. While sputum testing can be performed to determine the resident pathogen or pathogens, this sometimes requires that specimens be obtained by bronchoscopy with special techniques to avoid sample contamination that typically effect other methods and modalities of collection. Another issue is that currently-available medicines are not always effective, due to pathogens developing a resistance to these therapies.

B. Interventional Procedures

More recently, several groups have developed interventional procedures for COPD. Surgical Lung Volume Reduction (LVR) has been proven to be an effective therapy, although the morbidity and mortality rates are high in this frail population. Bronchoscopic Lung Volume Reduction (BLVR) can be achieved by the placement of one-way valves, coils, vapor steam ablation, or by delivering biologic or polymer based tissue glues into target lobes. The physiologic target for LVR/BLVR is emphysema, which specifically addresses the hyperinflation that these patients experience. In several studies, BLVR has been demonstrated to improve pulmonary function and quality of life. Volume reducing therapies are not effective in patients with chronic bronchitis, which is a disease of the airways, not the alveoli.

Another emerging therapy is lung denervation in which the parasympathetic nerves that innervate the airways are ablated, theoretically leading to chronic bronchodilation by disabling the reactive airway smooth muscle. The effect can be similar to the bronchodilator drugs like LABAs and LAMAs, but provide for long-term effect without the typical peaks and troughs seen with medication dosing. Due to only proximal treatment with this modality, it can be limited in effect to the upper airways whereas the higher resistance airways are lower in the respiratory tract.

A variety of thermal ablation approaches have also been described as therapies to treat diseased airways, but all have limitations and challenges associated with controlling the ablation and/or targeting specific cell types. Spray cryotherapy is applied by spraying liquid nitrogen directly onto the bronchial wall with the intent of ablating superficial airway cells and initiating a regenerative effect on the bronchial wall. Since the operator (e.g. physician) is essentially 'spray painting' the wall, coverage, dose and/or depth of treatment can be highly operator dependent without appropriate controllers. This can lead to incomplete treatment with skip areas that were not directly sprayed with nitrogen. Lack of exact depth control can also lead to unintended injury to tissues beyond the therapeutic target such as lamina propria and cartilage, especially since airway wall thickness can vary. Radiofrequency and microwave ablation techniques have also been described wherein energy is delivered to the airway wall in a variety of locations to ablate diseased tissue. Due to uncontrolled thermal conduction, an inability to measure actual tissue temperature to control energy delivery, risk of overlapping treatments, and variable wall thickness of the bronchi, these therapies can cause unintended injury to tissues beyond the therapeutic target, as well. In addition, since they all require repositioning of the catheter for multiple energy applications, incomplete treatment can also occur. All of these thermal ablative technologies non-selectively ablate various layers of the airway wall, often undesirably ablating non-target tissues beyond the epithelium. As a consequence of damage to tissues beyond the therapeutic targets of the epithelium, an inflammatory cascade can be triggered, resulting in inflammation, which can lead to an exacerbation, and remodeling. As a result, the airway lumen can be further reduced. Thus, continued improvements in interventional procedures are needed which are more controlled, targeted to specific depths and structures that match the physiologic malady, while limiting the amount of inflammatory response and remodeling.

Asthmatx has previously developed a radiofrequency ablation system to conduct Bronchial Thermoplasty. The operator deploys a catheter in the airways and activates the electrode, generating heat in the airway tissue in order to thermally ablate smooth muscle. Because of the acute inflammation associated with the heat generated in the procedure, many patients experience acute exacerbations. In the AIR2 clinical study, patients did not experience a clinically significant improvement in the Asthma Quality of Life Questionnaire at 12 months as compared to a sham group.

However, the treatment group had fewer exacerbations and a decrease in emergency room visits. The FDA approved the procedure, but it is not commonly used due to the side effects and the designation by insurers as an investigational procedure.

There is hence an unmet need for interventional procedures which are more controlled, targeted to specific structures and/or pathogens that match the pathophysiologic aberrancy or aberrancies, able to treat relatively large surface areas at the appropriate depth, and limit the amount of inflammatory response and remodeling. The present invention meets at least some of these objectives.

SUMMARY OF THE INVENTION

Described herein are embodiments of apparatuses, systems and methods for treating or manipulating pulmonary tissues and/or treating pulmonary diseases or disorders such as or associated with COPD (e.g., chronic bronchitis, emphysema), asthma, interstitial pulmonary fibrosis, cystic fibrosis, bronchiectasis, primary ciliary dyskinesia (PCD), acute bronchitis and/or other pulmonary diseases or disorders, wherein one or more features from any of these embodiments can be combined with one or more features from one or more other embodiments to form a new embodiment within the scope of this disclosure. Example pulmonary tissues include, without limitation, the epithelium (the goblet cells, ciliated pseudostratified columnar epithelial cells, and basal cells), lamina propria, submucosa, submucosal glands, basement membrane, smooth muscle, cartilage, nerves, pathogens resident near or within the tissue, or a combination of any or all of the foregoing.

The methods, apparatuses, and systems disclosed herein can treat pulmonary tissues via delivery of energy, generally characterized by high voltage pulses, to target tissue using a pulmonary tissue modification system (e.g., an energy delivery catheter system). In some embodiments, the nature of the energy delivery allows for removal of target tissue without a clinically significant inflammatory healing response, while in other embodiments, some inflammatory healing response is considered acceptable. This further allows for regeneration of healthy new target tissue within days of the procedure. In other embodiments, the nature of the energy delivery allows for removal of pathogens resident in the airway, such as by destruction, without substantially impacting or injuring any other airway structures.

In a first aspect, a system is provided for reducing hypersecretion of mucus in a lung passageway of a patient, the system comprising, a) a catheter comprising at least one electrode disposed near its distal end, wherein the distal end of the catheter is configured to be positioned within a lung passageway so that the at least one electrode is able to transmit non-thermal energy to an airway wall of the lung passageway, and b) and a generator in electrical communication with the at least one electrode, wherein the generator includes at least one energy delivery algorithm configured to provide an electric signal of the non-thermal energy transmittable to the airway wall which selectively treats particular cells associated with hypersecretion of mucus within the airway wall causing reduced hypersecretion of mucus by the airway wall.

In some embodiments, selectively treats comprises selectively removes the particular cells from the airway wall. In some embodiments, removes comprises cell detachment. For example, cell detachment may be achieved by dielectrophoresis. In some embodiments, removes comprises cell death. For example, cell death may be achieved by electroporation. Or, cell death may occur by other mechanisms. Likewise, removes may comprise a combination of dielectrophoresis and electroporation or other mechanisms.

In some embodiments, the particular cells comprise epithelial cells and not basal cells. For example, the epithelial cells may comprise abnormal or hyperplastic goblet cells. Or, the epithelial cells may comprise abnormal ciliated pseudostratified columnar epithelial cells.

In some embodiments, the particular cells comprise cells of a basement membrane, and wherein selectively treats comprises modifying the cells of the basement membrane so as to modify the permeability of the basement membrane. In some embodiments, the particular cells comprise submucosal glands, and wherein selectively treats comprises causing cell death of the submucosal glands. In some embodiments, the particular cells comprise pathogens, and wherein selectively treats comprises causing cell death of the pathogens. In some embodiments, selectively treats comprises selectively modifies the particular cells to alter mucus production.

In some embodiments, the electric signal has a waveform comprising at least one energy packet, wherein each energy packet comprises a series of pulses. In some instances, each pulse is between approximately 500 V to 10 kV. In other instances, each pulse is between approximately 500-4000 V.

In some embodiments, the at least one energy packet has a frequency in the range of approximately 500-800 kHz. It may be appreciated that in some embodiments, each pulse is biphasic.

In some embodiments, the system further comprises a temperature sensor disposed along the catheter so as to contact the airway wall and monitor temperature at or in the airway wall. In some embodiments, the generator includes a processor in communication with the temperature sensor, wherein the processor modifies the at least one energy delivery algorithm if the temperature increases to or above a temperature threshold for thermal tissue effects.

In some embodiments, the system further comprises an impedance sensor disposed along the catheter so as to contact the airway wall and monitor impedance within the airway wall, wherein the impedance sensor communicates with an indicator that indicates a condition of the airway wall based on the impedance. In some instances, the condition of the airway wall comprises completeness of treatment of the particular cells.

In some instances, the condition of the airway wall comprises lack of effect of the treatment of the particular cells.

In some embodiments, the generator further comprises a mechanism for acquiring a cardiac signal of the patient and a processor configured to identify a safe time period for transmitting the non-thermal energy to the airway wall of the lung passageway based on the cardiac signal. In some embodiments, the safe time period occurs during an ST segment of the cardiac signal. In other embodiments, the safe time period occurs during a QT interval of the cardiac signal.

In some embodiments, the system further comprises at least one sensor configured to sense a parameter of the airway wall, wherein the generator further comprises a processor configured to modify the at least one energy delivery algorithm based on data from the at least one sensor so as to create a feedback loop.

In some embodiments, the catheter comprises at least two protrusions expandable to contact the airway wall of the lung passageway. In some embodiments, the at least two protrusions comprises a plurality of wires forming an expandable basket, wherein at least one of wires acts as the at least one electrode. In some embodiments, the catheter includes a shaft and wherein the shaft does not pass through the expandable basket. In some embodiments, at least a portion of one of the plurality of wires is insulated from a nearby wire of the plurality of wires. In some embodiments, the at least a portion of one of the plurality of wires is insulated leaving an exposed portion of wire so as to create an active area which concentrates the energy at a particular location along the airway wall of the lung passageway. In some embodiments, the plurality of wires is simultaneously energizable. In other embodiments, at least some of the plurality of wires are individually energizable.

In some embodiments, the at least one electrode comprises a separate electrode mounted on at least one of the at least two protrusions. In such embodiments, the separate electrode may have a coil shape.

In some embodiments, the catheter includes a shaft and wherein the at least two protrusions comprises a plurality of wires having one end attached to the shaft and one free end so as to form a half expandable basket.

In some embodiments, the system further comprises a sheath advanceable over the catheter so as the collapse the at least two protrusions.

In a second aspect of the present invention, a system is provided for regenerating normative healthy tissue in an abnormally functioning lung passageway of a patient, the system comprising, a) a catheter comprising at least one electrode disposed near its distal end, wherein the distal end of the catheter is configured to be positioned within a lung passageway so that the at least one electrode is able to transmit non-thermal energy to an airway wall of the lung passageway, and b) a generator in electrical communication with the at least one electrode, wherein the generator includes at least one energy delivery algorithm configured to provide an electric signal of the non-thermal energy transmittable to the airway wall which removes abnormally functioning cells from the airway wall while maintaining a collagen matrix structure within the airway wall so as to allow regeneration of the airway wall with normative healthy tissue.

In some embodiments, removes comprises cell detachment. For example, cell detachment may be achieved by dielectrophoresis. In some embodiments, removes comprises cell death. For example, cell death may be achieved by electroporation. Or, cell death may occur by other mechanisms. Likewise, removes may comprise a combination of dielectrophoresis and electroporation or other mechanisms.

In some embodiments, the abnormally functioning cells comprise epithelial cells and not basal cells. In some instances, the epithelial cells comprise abnormal or hyperplastic goblet cells. In some instances, the epithelial cells comprise abnormal ciliated pseudostratified columnar epithelial cells. In some embodiments, the abnormally functioning cells comprise submucosal glands, and wherein removes comprises causing cell death of the submucosal glands.

In some embodiments, the electric signal has a waveform comprising at least one energy packet, wherein each energy packet comprises a series of pulses. In some instances, each pulse is between approximately 500 V to 10 kV. In other instances, each pulse is between approximately 500-4000 V. In some embodiments, the at least one energy packet has a frequency in the range of approximately 500-800 kHz. In some embodiments, each pulse is biphasic.

In some embodiments, the system further comprises a temperature sensor disposed along the catheter so as to contact the airway wall and monitor temperature at or in the airway wall. In some embodiments, the generator includes a processor in communication with the temperature sensor, wherein the processor modifies the at least one energy delivery algorithm if the temperature increases to or above a temperature threshold for thermal tissue effects.

In some embodiments, the system further comprises an impedance sensor disposed along the energy catheter so as to contact the airway wall and monitor impedance within the airway wall, wherein the impedance sensor communicates with an indicator that indicates a condition of the airway wall based on the impedance.

In some embodiments, the condition of the airway wall comprises lack of effect of removal of abnormally functioning cells.

In some embodiments, the generator further comprises a mechanism for acquiring a cardiac signal of the patient and a processor configured to identify a safe time period for transmitting the non-thermal energy to the airway wall of the lung passageway based on the cardiac signal. In some embodiments, the safe time period occurs during an ST segment of the cardiac signal. In other embodiments, the safe time period occurs during a QT interval of the cardiac signal.

In some embodiments, the system further comprises at least one sensor configured to sense a parameter of the airway wall, wherein the generator further comprises a processor configured to modify the at least one energy delivery algorithm based on data from the at least one sensor so as to create a feedback loop.

In some embodiments, the catheter comprises at least two protrusions expandable to contact the airway wall of the lung passageway. In some instances, the at least two protrusions comprises a plurality of wires forming an expandable basket, wherein at least one of wires acts as the at least one electrode.

In some embodiments, the catheter includes a shaft and wherein the shaft does not pass through the expandable basket.

In some embodiments, at least a portion of one of the plurality of wires is insulated from a nearby wire of the plurality of wires. In some embodiments, the at least a portion of one of the plurality of wires is insulated leaving an exposed portion of wire so as to create an active area which concentrates the energy at a particular location along the airway wall of the lung passageway. In some embodiments, the plurality of wires is simultaneously energizable. In other embodiments, at least some of the plurality of wires are individually energizable.

In some embodiments, the at least one electrode comprises a separate electrode mounted on at least one of the at least two protrusions. In such instances, the separate electrode may have a coil shape.

In some embodiments, the catheter includes a shaft and wherein the at least two protrusions comprises a plurality of wires having one end attached to the shaft and one free end so as to form a half expandable basket.

In some embodiments, the system further comprises a sheath advanceable over the catheter so as the collapse the at least two protrusions.

In a third aspect of the present invention, a system is provided for regenerating normative healthy tissue in an abnormally functioning lung passageway of a patient, the system comprising, a) a catheter comprising at least one electrode disposed near its distal end, wherein the distal end of the catheter is configured to be positioned within a lung passageway so that the energy delivery body is able to transmit non-thermal energy to an airway wall of the lung passageway, and b) a generator in electrical communication with the at least one electrode, wherein the generator includes at least one energy delivery algorithm configured to provide an electric signal of the non-thermal energy transmittable to the airway wall which removes cells from the airway wall that are contributing to abnormal function of the lung passageway while maintaining a collagen matrix structure within the airway wall so as to allow regeneration of the airway wall with normative healthy tissue.

In some embodiments, removes comprises cell detachment. For example, the electric signal may cause cell detachment by dielectrophoresis. In some embodiments, removes comprises cell death.

In some embodiments, the cells comprise epithelial cells and not basal cells. For instance, the epithelial cells may comprise abnormal or hyperplastic goblet cells. Or, the epithelial cells may comprise abnormal ciliated pseudostratified columnar epithelial cells.

In some embodiments, the cells comprise lymphocytes, macrophages, eosinophils, fibroblasts, plasma cells, mast cells, leukocytes or a combination of these. In some embodiments, the cells comprise submucosal glands, and wherein removes comprises causing cell death of the submucosal glands. In other embodiments, the cells comprise pathogens.

In some embodiments, the electric signal has a waveform comprising at least one energy packet, wherein each energy packet comprises a series of pulses. For example, each pulse may be between approximately 500 V to 10 kV. Or, each pulse may be between approximately 500-4000 V. In some embodiments, the at least one energy packet has a frequency in the range of approximately 500-800 kHz. In some embodiments, each pulse is biphasic.

In some embodiments, the system further comprises a temperature sensor disposed along the catheter so as to contact the airway wall and monitor temperature at or in the airway wall.

In some embodiments, the generator includes a processor in communication with the temperature sensor, wherein the processor modifies the at least one energy delivery algorithm if the temperature increases to or above a temperature threshold for thermal tissue effects.

In some embodiments, the system further comprises an impedance sensor disposed along the catheter so as to contact the airway wall and monitor impedance within the airway wall, wherein the impedance sensor communicates with an indicator that indicates a condition of the airway wall based on the impedance.

In some embodiments, the condition of the airway wall comprises lack of effect of removal of cells.

In some embodiments, the generator further comprises a mechanism for acquiring a cardiac signal of the patient and a processor configured to identify a safe time period for transmitting the non-thermal energy to the airway wall of the lung passageway based on the cardiac signal. In some embodiments, the safe time period occurs during an ST segment of the cardiac signal. In some embodiments, the safe time period occurs during a QT interval of the cardiac signal.

In some embodiments, the system further comprising at least one sensor configured to sense a parameter of the airway wall, wherein the generator further comprises a processor configured to modify the at least one energy delivery algorithm based on data from the at least one sensor so as to create a feedback loop.

In some embodiments, the catheter comprises at least two protrusions expandable to contact the airway wall of the lung passageway. In some embodiments, the at least two protrusions comprises a plurality of wires forming an expandable basket, wherein at least one of wires acts as the at least one electrode.

In some embodiments, the catheter includes a shaft and wherein the shaft does not pass through the expandable basket.

In some embodiments, at least a portion of one of the plurality of wires is insulated from a nearby wire of the plurality of wires. In some embodiments, the at least a portion of one of the plurality of wires is insulated leaving an exposed portion of wire so as to create an active area which concentrates the energy at a particular location along the airway wall of the lung passageway.

In some embodiments, the plurality of wires is simultaneously energizable. In other embodiments, at least some of the plurality of wires are individually energizable.

In some embodiments, the at least one electrode comprises a separate electrode mounted on at least one of the at least two protrusions. In such embodiments, the separate electrode may have a coil shape.

In some embodiments, the catheter includes a shaft and wherein the at least two protrusions comprises a plurality of wires having one end attached to the shaft and one free end so as to form a half expandable basket.

In some embodiments, the system further comprises a sheath advanceable over the catheter so as the collapse the at least two protrusions.

In a fourth aspect of the present invention, a system is provided for removing epithelial cells from a body passageway, the system comprising, a) a catheter comprising at least one electrode disposed near its distal end, wherein the distal end of the catheter is configured to be positioned within the body passageway so that the at least one electrode is able to transmit non-thermal energy to a wall of the body passageway, and b) a generator in electrical communication with the at least one electrrode, wherein the generator includes at least one energy delivery algorithm configured to provide an electric signal of the non-thermal energy transmittable to the airway wall which detaches epithelial cells from the wall by dielectrophoresis so as to allow regeneration of the wall with normative healthy tissue.

In some embodiments, the epithelial cells comprise goblet cells. In other embodiments, the epithelial cells comprise ciliated pseudostratified columnar epithelial cells. In yet other embodiments, the epithelial cells comprise goblet cells and ciliated pseudostratified columnar epithelial cells but not basal cells.

In some embodiments, the body passageway comprises a lung passageway. For example, the body passageway may comprises a blood vessel, a lymphatic vessel, a kidney tubule, an esophagus, a stomach, a small intestine, a large intestine, a large intestine, an appendix, a rectum, a bladder, a ureter, a pharynx, a mouth, a vagina, a urethra, or a duct of a gland.

In some embodiments, the electric signal has a waveform comprising at least one energy packet, wherein each energy packet comprises a series of pulses. In some embodiments, each pulse is between approximately 500 V to 10 kV. In other embodiments, each pulse is between approximately 500-4000 V. In some embodiments, the at least one energy packet has a frequency in the range of approximately 500-800 kHz. In some embodiments, each pulse is biphasic.

In some embodiments, the system further comprises a temperature sensor disposed along the catheter so as to contact the airway wall and monitor temperature at or in the airway wall. In some embodiments, the generator includes a processor in communication with the temperature sensor, wherein the processor modifies the at least one energy delivery algorithm if the temperature increases to or above a temperature threshold for thermal tissue effects.

In some embodiments, the system further comprises an impedance sensor disposed along the catheter so as to contact the airway wall and monitor impedance within the airway wall, wherein the impedance sensor communicates with an indicator that indicates a condition of the airway wall based on the impedance. In some embodiments, the condition of the airway wall comprises lack of effect of detachment of cells.

In some embodiments, the generator further comprises a mechanism for acquiring a cardiac signal of the patient and a processor configured to identify a safe time period for transmitting the non-thermal energy to the airway wall of the lung passageway based on the cardiac signal. In some embodiments, the safe time period occurs during an ST segment of the cardiac signal. In some embodiments, the safe time period occurs during a QT interval of the cardiac signal.

In some embodiments, the system further comprises at least one sensor configured to sense a parameter of the airway wall, wherein the generator further comprises a processor configured to modify the at least one energy delivery algorithm based on data from the at least one sensor so as to create a feedback loop.

In some embodiments, the catheter comprises at least two protrusions expandable to contact the airway wall of the lung passageway. In some embodiments, the at least two protrusions comprises a plurality of wires forming an expandable basket, wherein at least one of wires acts as the at least one electrode. In some embodiments, the catheter includes a shaft and wherein the shaft does not pass through the expandable basket. In some embodiments, the at least a portion of one of the plurality of wires is insulated from a nearby wire of the plurality of wires. In some embodiments, the at least a portion of one of the plurality of wires is insulated leaving an exposed portion of wire so as to create an active area which concentrates the energy at a particular location along the airway wall of the lung passageway.

In some embodiments, the plurality of wires is simultaneously energizable. In some embodiments, at least some of the plurality of wires are individually energizable.

In some embodiments, the at least one electrode comprises a separate electrode mounted on at least one of the at least two protrusions. In such instances, the separate electrode may have a coil shape.

In some embodiments, the catheter includes a shaft and wherein the at least two protrusions comprises a plurality of wires having one end attached to the shaft and one free end so as to form a half expandable basket.

In some embodiments, they system further comprises a sheath advanceable over the catheter so as the collapse the at least two protrusions.

In a fifth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least one energy delivery algorithm and a processor, wherein the processor which provides an electrical signal of the energy according to the at least one energy delivery algorithm, each electrical signal having a waveform comprising at least one energy packet, wherein each energy packet comprises a series of pulses, and wherein the energy selectively treats particular cells associated with hypersecretion of mucus within the lung passageway causing reduced hypersecretion of mucus.

In some embodiments, each pulse is between approximately 500-4000 volts.

In some embodiments, the energy is delivered in a monopolar fashion and each pulse is between approximately 2000-3500 volts. In other embodiments, the energy is delivered in a bipolar fashion and each pulse is between approximately 500-1900 volts.

In some embodiments, the particular cells comprise epithelial cells and not basal cells.

In some embodiments, an increase in voltage of the pulses causes the energy to selectively treat particular cells located more deeply within a wall of the lung passageway.

In some embodiments, the at least one energy packet has a frequency is in the range of approximately 500-800 kHz.

In some embodiments, the energy is below a threshold for treating a cartilage layer within the lung passageway. In some embodiments, the energy is below a threshold for causing thermal ablation.

In some embodiments, the system further comprises a temperature sensor configured to contact a wall of the lung passageway and monitor temperature at or in the wall.

In some embodiments, the processor is in communication with the temperature sensor, and wherein the processor modifies the at least one energy delivery algorithm if the temperature increases to or above a temperature threshold for thermal tissue effects. In some embodiments, each pulse is biphasic.

In some embodiments, treats comprises removes the particular cells.

In some embodiments, the particular cells comprise cells of a basement membrane, and wherein selectively treats comprises modifying the cells of the basement membrane so as to modify the permeability of the basement membrane.

In some embodiments, the particular cells comprise submucosal glands, and wherein selectively treats comprises causing cell death of the submucosal glands. In some embodiments, the particular cells comprise pathogens, and wherein selectively treats comprises causing cell death of the pathogens.

In some embodiments, the system further comprises a cardiac monitor configured to acquire a cardiac signal of the patient, and wherein the processor provides the electrical signal of the energy in synchronization with the cardiac signal.

In some embodiments, the processor provides the electrical signal of energy during an ST segment of the cardiac signal. In other embodiments, the processor provides the electrical signal of energy during a QT interval of the cardiac signal.

In some embodiments, the system further comprises an impedance sensor configured to contact a wall of the lung passageway and monitor impedance within the wall, wherein the impedance sensor communicates with an indicator that indicates a condition of the wall based on the impedance. In some embodiments, the condition of the airway wall comprises completeness of treatment of the particular cells. In some embodiments, the condition of the airway wall comprises lack of effect of the treatment of the particular cells.

In some embodiments, the system further comprises at least one sensor configured to sense a parameter of a wall of the lung passageway, wherein the processor modifies the at least one energy delivery algorithm based on data from the at least one sensor so as to create a feedback loop.

In a sixth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least one energy delivery algorithm and a processor, wherein the processor provides an electrical signal of the energy according to the at least one energy delivery algorithm and wherein the energy selectively treats particular cells associated with hypersecretion of mucus within the lung passageway causing reduced hypersecretion of mucus, and b) at least one sensor in communication with the processor, wherein the sensor senses a condition of the lung passageway and the processor modifies at least one parameter of the at least one energy delivery algorithm based on the condition.

In some embodiments, the at least one parameter includes a voltage, frequency, packet duration, cycle count, number of energy packets, rest period or dead time.

In some embodiments, the at least one sensor comprises a temperature sensor and the condition comprises a temperature of a portion of a wall of the lung passageway.

In some embodiments, the at least one parameter includes a voltage, and wherein the processor reduces the voltage if the temperature reaches a temperature threshold.

In some embodiments, the processor ceases providing the electrical signal of energy if the temperature reaches a temperature threshold.

In some embodiments, the system further comprises the catheter, wherein the catheter includes at least one electrode positionable near or against a wall of the lung passageway so as to transmit the energy to the lung passageway, wherein the at least one sensor comprises a temperature sensor and the condition comprises a temperature of the at least one electrode.

In some embodiments, the at least one sensor comprises an impedance sensor and the condition comprises an impedance of a portion of a wall of the lung passageway. In some embodiments, the processor compares the impedance to an impedance threshold and causes the generator to provide an alert if the impedance is above the impedance threshold.

In some embodiments, the system further comprises the catheter, wherein the catheter includes at least one electrode positionable near or against a wall of the lung passageway so as to transmit the energy to the lung passageway, and wherein the alert comprises an indication that at least one of the at least one electrodes is not properly positioned.

In some embodiments, the at least one parameter includes a voltage, and wherein the processor reduces the voltage if the impedance reaches an impedance threshold.

In some embodiments, the processor ceases providing the electrical signal of energy if the impedance reaches an impedance threshold. In some embodiments, the at least one sensor comprises a temperature sensor, and impedance sensor, a surface conductance sensor, a membrane potential sensor, a capacitance sensor, a force sensor, or a pressure sensor.

In some embodiments, the system further comprises a cardiac monitor configured to acquire a cardiac signal of the patient, and wherein the processor provides the electrical signal of the energy in synchronization with the cardiac signal. In some embodiments, the condition of the lung passageway comprises completeness of treatment of the particular cells. In some embodiments, the condition of the lung passageway comprises lack of effect of the treatment of the particular cells.

In a seventh aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least two energy delivery algorithms and a processor, wherein the processor selects one of the at least two energy delivery algorithms and provides an electrical signal of the energy according to the one of the at least two energy delivery algorithms and wherein the energy selectively treats particular cells associated with hypersecretion of mucus within the lung passageway causing reduced hypersecretion of mucus, and b) at least one sensor in communication with the processor, wherein the sensor senses a condition of the lung passageway and the processor selects a different one of the at least two energy delivery algorithms and provides an electrical signal of the energy according to the different one of the at least two energy delivery algorithms.

In some embodiments, the at least one sensor comprises a temperature sensor and the condition comprises a temperature of a portion of a wall of the lung passageway.

In some embodiments, the system further comprises the catheter, wherein the catheter includes at least one electrode positionable near or against a wall of the lung passageway so as to transmit the energy to the lung passageway, wherein the at least one sensor comprises a temperature sensor and the condition comprises a temperature of the at least one electrode.

In some embodiments, the at least one sensor comprises an impedance sensor and the condition comprises an impedance of a portion of a wall of the lung passageway. In some embodiments, the processor compares the impedance to an impedance threshold and causes the generator to provide an alert if the impedance is above the impedance threshold. In some embodiments, the at least one parameter includes a voltage, and wherein the processor reduces the voltage if the impedance reaches an impedance threshold.

In some embodiments, the at least one sensor comprises a temperature sensor, and impedance sensor, a surface conductance sensor, a membrane potential sensor, a capacitance sensor, a force sensor, or a pressure sensor.

In some embodiments, the system further comprises a cardiac monitor configured to acquire a cardiac signal of the patient, and wherein the processor provides the electrical signal of the energy in synchronization with the cardiac signal. In some embodiments, the condition of the lung passageway comprises completeness of treatment of the particular cells. In some embodiments, the condition of the lung passageway comprises lack of effect of the treatment of the particular cells.

In an eighth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least one energy delivery algorithm and a processor, wherein the processor provides an electrical signal of the energy according to the at least one energy delivery algorithm and wherein the energy removes abnormally functioning cells from the airway wall, and b) at least one sensor in communication with the processor, wherein the sensor senses a condition of the lung passageway and the processor modifies at least one parameter of the at least one energy delivery algorithm based on the condition.

In ninth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least one energy delivery algorithm and a processor, wherein the processor provides an electrical signal of the energy according to the at least one energy delivery algorithm and wherein the energy removes cells from the airway wall that are contributing to abnormal function of the lung passageway while maintaining a collagen matrix structure within the airway wall so as to allow regeneration of the airway wall with normative healthy tissue, and b) at least one sensor in communication with the processor, wherein the sensor senses a condition of the lung passageway and the processor modifies at least one parameter of the at least one energy delivery algorithm based on the condition.

In a tenth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least one energy delivery algorithm and a processor, wherein the processor provides an electrical signal of the energy according to the at least one energy delivery algorithm and wherein the energy detaches epithelial cells from the wall by dielectrophoresis so as to allow regeneration of the wall with normative healthy tissue, and b) at least one sensor in communication with the processor, wherein the sensor senses a condition of the lung passageway and the processor modifies at least one parameter of the at least one energy delivery algorithm based on the condition.

In an eleventh aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least two energy delivery algorithms and a processor, wherein the processor selects one of the at least two energy delivery algorithms and provides an electrical signal of the energy according to the one of the at least two energy delivery algorithms and wherein the energy removes abnormally functioning cells from the airway wall, and b) at least one sensor in communication with the processor, wherein the sensor senses a condition of the lung passageway and the processor selects a different one of the at least two energy delivery algorithms and provides an electrical signal of the energy according to the different one of the at least two energy delivery algorithms.

In a twelfth aspect of the present invention, a system is provided for treating a lung passageway of a patient comprising, a) a generator configured to provide energy to a catheter which is configured to be positioned within the lung passageway so that the energy is transmittable to the lung passageway, wherein the generator includes at least two energy delivery algorithms and a processor, wherein the processor selects one of the at least two energy delivery algorithms and provides an electrical signal of the energy according to the one of the at least two energy delivery algorithms and wherein the energy removes cells from the airway wall that are contributing to abnormal function of the lung passageway while maintaining a collagen matrix structure within the airway wall so as to allow regeneration of the airway wall with normative healthy tissue, and b) at least one sensor in communication with the processor, wherein the sensor senses a condition of the lung passageway and the processor selects a different one of the at least two energy delivery algorithms and provides an electrical signal of the energy according to the different one of the at least two energy delivery algorithms.

In a thirteenth aspect of the present invention, a system is provided for treating a lung passageway of a patient comprising a) a generator configured to provide energy to a catheter which is configured to be positioned within the lung passageway so that the energy is transmittable to the lung passageway, wherein the generator includes at least two energy delivery algorithms and a processor, wherein the processor selects one of the at least two energy delivery algorithms and provides an electrical signal of the energy according to the one of the at least two energy delivery algorithms and wherein the energy detaches epithelial cells from the wall by dielectrophoresis so as to allow regeneration of the wall with normative healthy tissue, and b) at least one sensor in communication with the processor, wherein the sensor senses a condition of the lung passageway and the processor selects a different one of the at least two energy delivery algorithms and provides an electrical signal of the energy according to the different one of the at least two energy delivery algorithms.

In a fourteenth aspect of the present invention, a system is provided for treating a lung passageway of a patient comprising, a) a catheter having at least one electrode positionable near or against a wall of the lung passageway so as to transmit energy to the lung passageway, b) at least one sensor disposed along the catheter so as to senses a condition of the lung passageway to generate a condition value, and c) a generator having a processor configured to provide an alert if the sensor value is above a threshold.

In some embodiments, the at least one sensor comprises an impedance sensor and the condition value comprises an impedance of a portion of a wall of the lung passageway.

In some embodiments, the alert comprises an indication that at least one of the at least one electrodes is not properly positioned. In other embodiments, the alert comprises an indication that at least one of the at least one electrodes is defective.

In a fifteenth aspect of the present invention, a system is provided for treating a lung passageway of a patient comprising, a) a cardiac monitor configured to acquire a cardiac signal of the patient, b) a generator which provides an electrical signal of energy to at least one electrode which is positionable within the lung passageway so that the energy is transmittable to the lung passageway, wherein the generator provides the electrical signal in synchronization with the cardiac signal.

In some embodiments, the cardiac monitor is configured to send a cardiac sync pulse to the generator at a pre-determined point in the cardiac signal, and wherein the generator provides the electrical signal of energy after a pre-determined delay from receiving the cardiac sync pulse. In some embodiments, the pre-determined point is a peak of an R wave of the cardiac signal. In some embodiments, the pre-determined delay is in the range of 50-100 milliseconds.

In some embodiments, the generator includes a processor which monitors a plurality of cardiac sync pulses, calculates a time interval between successive cardiac sync pulse and prevents the generator from providing the electric signal if the time interval is not consistent for a pre-determined number of cardiac sync pulses. In some embodiments, the pre-determined number of cardiac sync pulses is five. In other embodiments, the pre-determined number of cardiac sync pulses is three. In some embodiments, the processor reduces the pre-determined number of cardiac sync pulses if the generator has prior been prevented from providing the electric signal. In some embodiments, the generator is configured to send the electrical signal during an ST segment of the cardiac signal. In some embodiments, the generator is configured to send the electrical signal during a QT interval of the cardiac signal. In some embodiments, the generator is configured to not send the electrical signal during a T wave of the cardiac signal. In some embodiments, the generator is configured to not send the electrical signal during a blanking period. In some embodiments, the blanking period is 100-200 milliseconds after an R wave peak of the cardiac signal.

In some embodiments, the system further comprises a catheter upon which the at least one electrode is mounted.

In some embodiments, the system further comprises an imaging modality configured to image the lung passageway. In some embodiments, the imaging modality comprises a bronchoscope.

In a sixteenth aspect of the present invention, a system is provided for reducing hypersecretion of mucus in a lung passageway of a patient, the system comprising, a) a catheter comprising an energy delivery body disposed near its distal end, wherein the energy delivery body comprises at least two protrusions expandable to contact a wall of the lung passageway, wherein each protrusion includes at least one electrode; and b) a generator which provides an electrical signal to the at least one electrode which transmits non-thermal energy toward the wall in an energy does, wherein the energy dose selectively treats particular cells associated with hypersecretion of mucus within the airway wall causing reduced hypersecretion of mucus by the airway wall.

In some embodiments, the at least two protrusions comprises a plurality of wires forming an expandable basket, wherein at least one of wires acts as the at least one electrode.

In some embodiments, the catheter includes a shaft and wherein the shaft does not pass through the expandable basket.

In some embodiments, the at least a portion of one of the plurality of wires is insulated from a nearby wire of the plurality of wires. In some embodiments, the at least a portion of one of the plurality of wires is insulated leaving an exposed portion of wire so as to create an active area which concentrates the energy dose at a particular location along the wall of the lung passageway.

In some embodiments, the plurality of wires is simultaneously energizable. In other embodiments, at least some of the plurality of wires are individually energizable.

In some embodiments, the at least one electrode comprises a separate electrode mounted on the at least two protrusions. In such embodiments, the separate electrode may have a coil shape.

In some embodiments, the catheter includes a shaft and wherein the at least two protrusions comprises a plurality of wires having one end attached to the shaft and one free end so as to form a half expandable basket.

In some embodiments, the system further comprises a sheath advanceable over the catheter so as the collapse the at least two protrusions.

In some embodiments, selectively treats comprises selectively removes the particular cells from the airway wall. The particular cells may comprise epithelial cells and not basal cells. In some instances, the epithelial cells comprise abnormal or hyperplastic goblet cells. In other instances, the epithelial cells comprise abnormal ciliated pseudostratified columnar epithelial cells.

In some embodiments, removes comprises cell detachment. In other embodiments, removes comprises cell death.

In some embodiments, the particular cells comprise cells of a basement membrane, and wherein selectively treats comprises modifying the cells of the basement membrane so as to modify the permeability of the basement membrane.

In some embodiments, the particular cells comprise submucosal glands, and wherein selectively treats comprises causing cell death of the submucosal glands.

In some embodiments, the particular cells comprise pathogens, and wherein selectively treats comprises causing cell death of the pathogens.

In some embodiments, selectively treats comprises selectively modifies the particular cells to alter mucus production.

In some embodiments, the electric signal has a waveform comprising at least one energy packet, wherein each energy packet comprises a series of pulses. In some instances, each pulse is between approximately 500 V to 10 kV.

In some embodiments, the system further comprises a temperature sensor disposed along the energy delivery body so as to contact the airway wall and monitor temperature at or in the airway wall.

In some embodiments, the generator includes a processor in communication with the temperature sensor, wherein the processor modifies the at least one energy delivery algorithm if the temperature increases to or above a temperature threshold for thermal tissue effects.

In some embodiments, the system further comprises an impedance sensor disposed along the energy delivery body so as to contact the airway wall and monitor impedance within the airway wall, wherein the impedance sensor communicates with an indicator that indicates a condition of the airway wall based on the impedance.

In some embodiments, the generator further comprises a mechanism for acquiring a cardiac signal of the patient and a processor configured to analyze the cardiac signal and identify a safe time period for transmitting the non-thermal energy to the airway wall of the lung passageway.

In some embodiments, the system further comprises at least one sensor configured to sense a parameter of the airway wall, wherein the generator further comprises a processor configured to modify the electric signal based on data from the at least one sensor so as to create a feedback loop.

In a seventeenth aspect of the present invention, a method is provided for reducing hypersecretion of mucus in a lung passageway of a patient comprising, a) positioning at least one electrode within the lung passageway so that the at least one electrode is disposed near or against a portion of an airway wall of the lung passageway, and b) energizing the at least one electrode so as to deliver non-thermal energy to the portion of the airway wall, wherein the non-thermal energy selectively treats particular cells within the portion of the airway wall associated with hypersecretion of mucus causing reduced hypersecretion of mucus by the lung passageway.

In some embodiments, selectively treats comprises selectively removes the particular cells from the airway wall. In some instances, the particular cells comprise epithelial cells and not basal cells. In some instances, the epithelial cells comprise abnormal or hyperplastic goblet cells. In other instances, the epithelial cells comprise abnormal ciliated pseudostratified columnar epithelial cells.

In some embodiments, removes comprises cell detachment. For example, removes may comprise cell detachment by dielectrophoresis. In some embodiments, removes comprises cell death.

In some embodiments, the particular cells comprise cells of a basement membrane, and wherein selectively treats comprises modifying the cells of the basement membrane so as to modify the permeability of the basement membrane.

In other embodiments, the particular cells comprise submucosal glands, and wherein selectively treats comprises causing cell death of the submucosal glands.

In yet other embodiments, the particular cells comprise pathogens, and wherein selectively treats comprises causing cell death of the pathogens.

In some embodiments, selectively treats comprises selectively modifies the particular cells to alter mucus production.

In some embodiments, the at least one electrode comprises a plurality of wires forming an expandable basket, and wherein positioning the at least one electrode within the lung passageway comprises expanding the expandable basket so that at least one of the plurality of wires contacts the airway wall of the lung passageway. In some embodiments, the plurality of wires acts as a monopolar electrode, and the method further comprises positioning a return electrode near the patient. In some embodiments, the plurality of wires acts as a bipolar electrode.

In some embodiments, the at least one electrode comprises at least two electrodes, and wherein energizing comprises energizing the at least two electrodes to act as a bipolar pair.

In some embodiments, the non-thermal energy has an energy dose, and the method further comprises re-energizing the at least one electrode so as to deliver non-thermal energy having a different energy dose.

In some embodiments, the re-energizing step is in response to a sensed condition of the portion of the airway wall. In some embodiments, the sensed condition comprises a temperature. In other embodiments, the sensed condition comprises an impedance.

In some embodiments, the method further comprises re-energizing the at least one electrode so as to selectively treat different cells within the portion of the airway wall. In some embodiments, the particular cells comprise epithelial cells and the different cells comprise submucosal cells.

In some embodiments, energizing the at least one electrode comprises energizing the at least one electrode in synchronization with a cardiac cycle of the patient. In some embodiments, in synchronization comprises outside of a T wave of the cardiac cycle.

In some embodiments, the method further comprises re-positioning the at least one electrode within the lung passageway so that the at least one electrode is disposed near or against a different portion of the airway wall of the lung passageway, and energizing the at least one electrode so as to deliver energy to the different portion of the airway wall. In some embodiments, the portion and the different portion are adjacent to each other.

In some embodiments, the method further comprises positioning the at least one electrode within a different lung passageway of the patient so that the at least one electrode is disposed near or against a portion of an airway wall of the different lung passageway, and energizing the at least one electrode so as to deliver energy to the portion of an airway wall of the different lung passageway.

In some embodiments, the non-thermal energy is provided by an electrical signal having a waveform comprising at least one energy packet, wherein each energy packet comprises a series of pulses. In some embodiments, each pulse is between approximately 500-4000 volts. In some embodiments, each energy packet has a frequency in the range of approximately 500-800 kHz.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 28A illustrates an embodiment wherein one energy delivery body energy is unconstrained at one end forming a half-basket shape when expanded.

FIG. 28B illustrates an embodiment wherein both the energy delivery bodies are comprised of braided metal wires configured to form half-baskets when expanded.

FIG. 29 illustrates a braided wire basket energy delivery body comprised of energizable wires wherein some of the wires are insulated with portions of the insulation removed to define an active area.

FIG. 30 illustrates another embodiment wherein a tube is laser cut to form a collapsed basket with both ends constrained via the tube itself.

FIG. 31 illustrates an embodiment of an energy delivery body comprised of wires which are insulated and one or more separate additional electrodes (shown as coils) are connected to the insulated basket wires to form active areas.

FIG. 32 illustrates an embodiment of an energy delivery body comprising a plurality of tines.

FIG. 35 illustrates an embodiment of a catheter having two energy delivery bodies, each energy delivery body having the shape of an expandable coil.

FIG. 36 illustrates an embodiment of an energy delivery body comprising a coil having a width and a length, wherein the length of the coil is pre-shaped into a substantially circular pattern.

FIG. 37 illustrates an embodiment of an energy delivery body comprising a rod having electrodes, wherein the length of the rod is pre-shaped into a substantially circular pattern.

FIG. 38 illustrates an embodiment of a catheter having a sheath withdrawn proximally thus exposing one or more prongs.

FIG. 38A is a cross-sectional illustration across A-A of FIG. 38.

FIG. 39 illustrates an embodiment of a prong having two electrodes attached to an insulating substrate therebetween as a means to maintain distance between the electrodes.

FIG. 40 illustrates an embodiment of a prong having a narrower insulating substrate than depicted in FIG. 36.

FIG. 41 illustrates an embodiment of a prong having yet narrower insulating substrates and greater than two electrodes.

FIG. 42 illustrates a plurality of electrodes mounted on an insulating substrate.

FIG. 43 illustrates the insulating substrate with electrodes as shown in FIGS. 36-37 configured as a helix.

FIG. 44 illustrates the insulating substrate with electrodes as shown in FIG. 38 configured as a helix.

FIGS. 45A-45B illustrate expanding an expandable member until a desired interface between the prongs and bronchial wall is achieved.

FIGS. 49A-49C illustrate introduction of a catheter having two energy delivery bodies through a bronchoscope.

FIG. 50 is a schematic illustration of a single target segment within a mainstem bronchi of a lung.

FIG. 51 is a schematic illustration of two target segments positioned adjacent to each other such that the overall target or treatment zone is generally contiguous.

FIG. 52 is a schematic illustration of two target zones within a patient.

FIG. 57A illustrates a section from an untreated airway, FIG. 57B illustrates a section from treated airway.

FIG. 58A illustrates a section of an untreated airway, FIG. 58B illustrates a section of a treated airway.

DETAILED DESCRIPTION OF THE INVENTION

Figure 1:
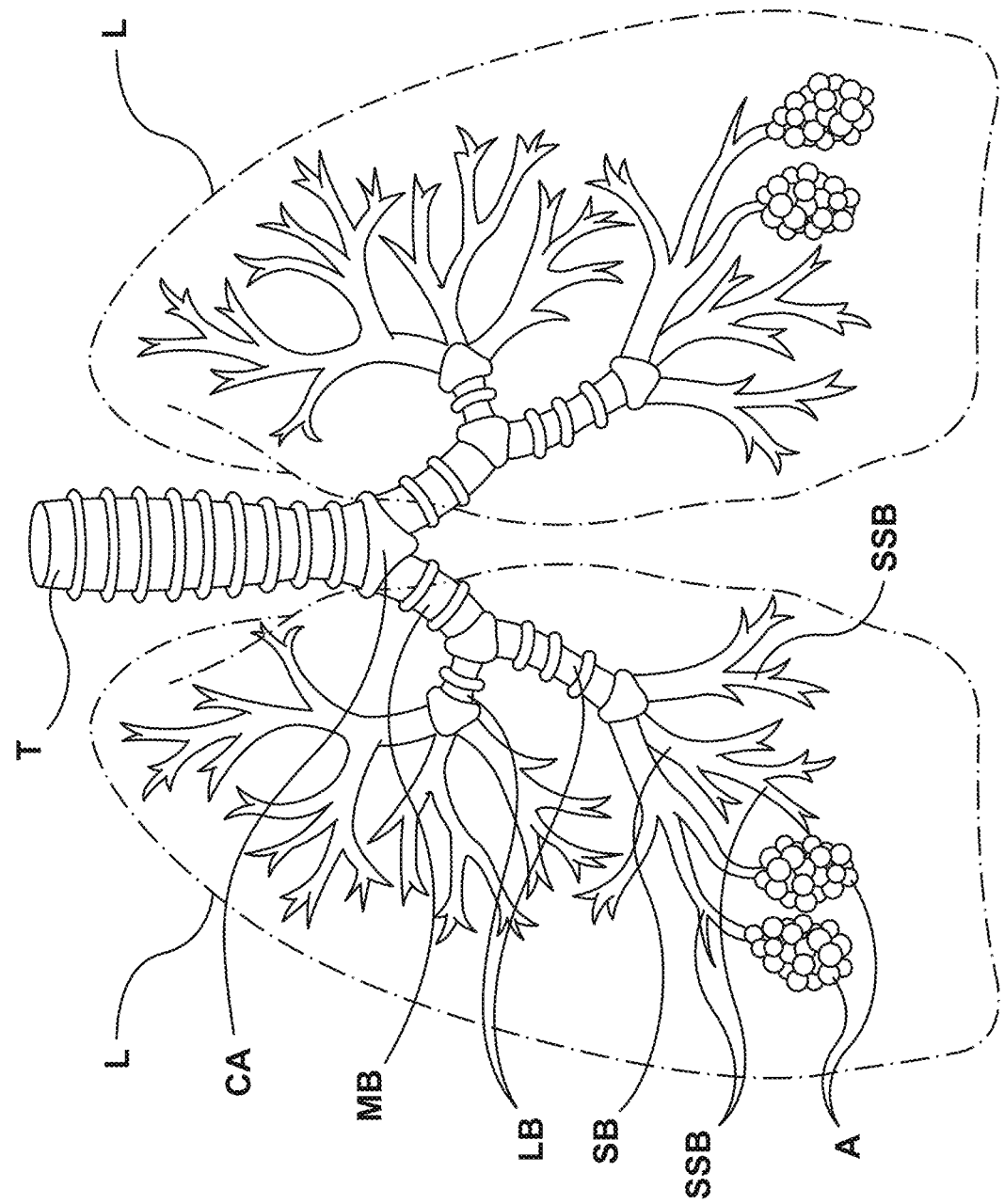
FIG. 1 provides an illustration of the pulmonary anatomy.
Figure 2:
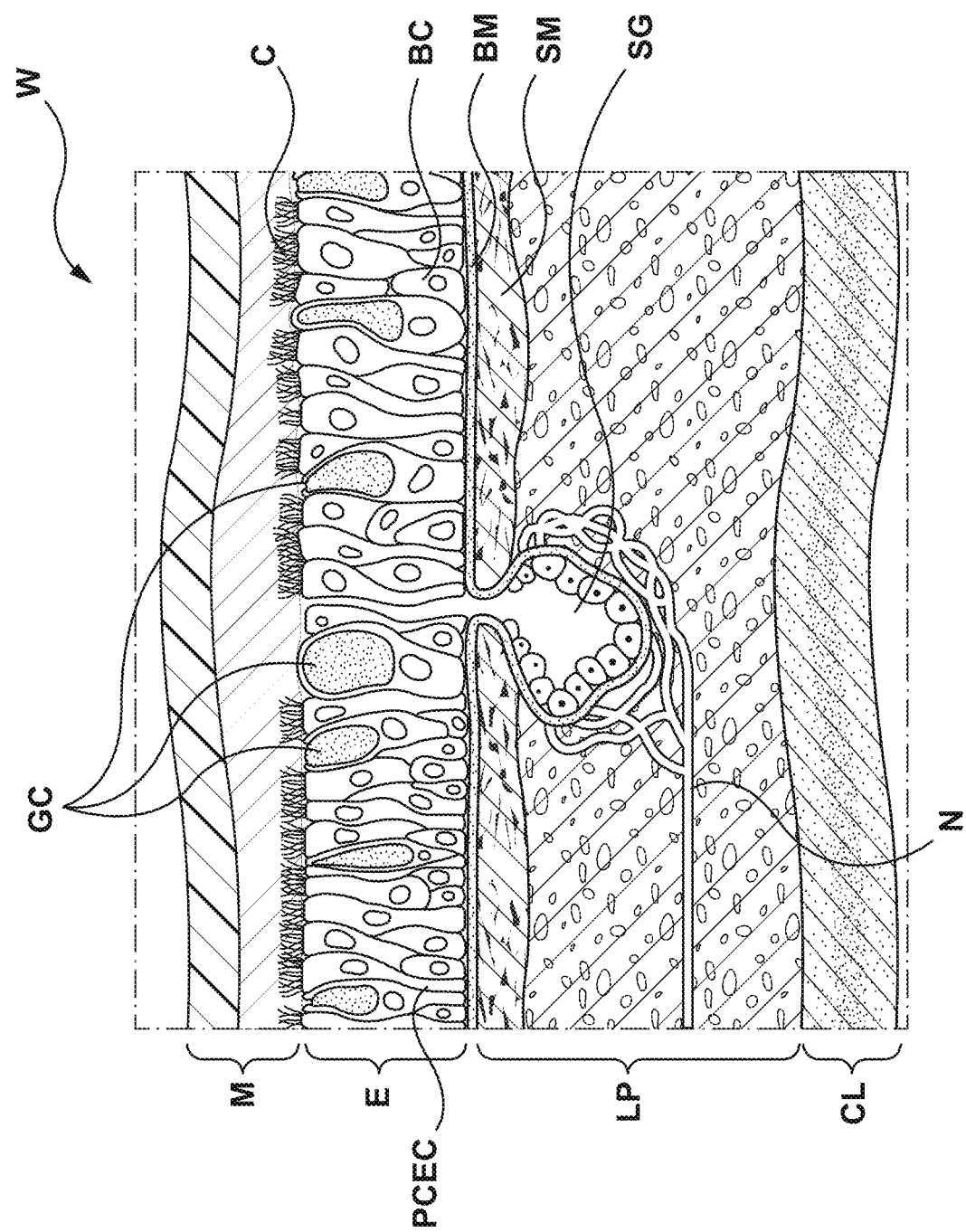
FIG. 2 illustrates a cross-sectional view representative of an airway wall having a variety of layers and structures.

Specific embodiments of the disclosed device, delivery system, and methods will now be described with reference to the drawings. Nothing in this detailed description is intended to imply that any particular component, feature, or step is essential to the invention.

I. OVERVIEW

The secretion of mucus in the bronchial airways is an inherent part of the defense of the lungs, protecting the interior membranes and assisting in fighting off infections. The amount of mucus secretion varies with a range of stimuli, including bacteria, particles and chemical irritants. Normal secretion levels rise and fall depending on the transient conditions of the environment. Mucus on the epithelial layer of the bronchial airways traps particles and the ciliated cells permits moving of the mucus out of the lower airways so that it can ultimately be cleared by coughing or swallowing. Mucus also contains antibacterial agents to aid in its defense function. Pathogens and harmless inhaled proteins are thus removed from the respiratory tract and have a limited encounter with other immune components. In the bronchial airways, mucus is produced by goblet cells. Goblet cells produce mucins that are complexed with water in secretory granules and are released into the airway lumen. In the large airways, mucus is also produced by mucus glands. After infection or toxic exposure, the airway epithelium upregulates its mucus secretory ability to cause coughing and release of sputum. Subsequently, the airway epithelium recovers and returns to its normal state, goblet cells disappear, and coughing abates.

However, in some instances, such as in the development of many pulmonary disorders and diseases, the body does not recover, chronically producing too much mucus and causing it to accumulate in the lungs. This creates symptoms such as chronic coughing, difficulty breathing, fatigue and chest pain or discomfort. Such hypersecretion of mucus occurs in many disease states and is a major clinical and pathological feature in cystic fibrosis (CF) related bronchiectasis, non-CF bronchiectasis, chronic obstructive pulmonary disease and asthma, to name a few.

These disorders are all associated with an impaired innate lung defense and considerable activation of the host inflammatory response. Abnormal levels of antimicrobial peptides, surfactant, salivary lysozyme, sputum secretory leukocyte protease inhibitor, and macrophages in addition to signaling of toll-like receptors (TLRs), trigger pathways for mucin transcription and NF-KB (nuclear factor kappa-light-chain-enhancer of activated B cells). The increased mucus production and decreased clearance causes increased exacerbations and airway epithelial injury. Ciliary activity is disrupted and mucin production is upregulated. There is expansion of the goblet cell population. Epithelial cell proliferation with differentiation into goblet cells increases. Likewise, inflammation is elevated during exacerbations which activates proteases, destroying the elastic fibers that allow air and $CO_2$ to flow in and out of alveoli. In response to injury, the airway epithelium produces even more mucus to clear the airways of inflammatory cells. This progresses the disorder. Pathogens invade the mucus, which cannot be cleared. This primes the airways for another exacerbation cycle. As exacerbation cycles continue, the excessive mucus production leads to a pathological state with increased risk of infection, hospitalization and morbidity.

To interrupt or prevent the cycle of disease progression, the airways are treated with a pulmonary tissue modification system useful for impacting one or more cellular structures in the airway wall such that the airway wall structures are restored from a diseased/remodeled state to a relatively normal state of architecture, function and/or activity. The pulmonary tissue modification system treats pulmonary tissues via delivery of energy, generally characterized by high voltage pulses. In some embodiments, the energy delivery allows for modification or removal of target tissue without a clinically significant inflammatory response, while in other embodiments, some inflammatory response is permissible. This allows for regeneration of healthy new tissue within days of the procedure.

In one method, the energy output from the pulmonary tissue modification system induces a separation in the epithelial layer E in which abnormal and dysfunctional ciliated pseudostratified columnar epithelial cells PCEC and hyperplastic and abnormal goblet cells GC are separated from the basal cells BC and pulled into the airway lumen, where they are expelled from the lumen of the airway. As a result, the basal cells BC are left on the basement membrane BM to regenerate normal goblet cells GC and normal ciliated pseudostratified columnar epithelial cells PCEC, thereby inducing reverse remodeling of the disease to reduce the mucus hypersecretion. The newly regenerated goblet cells GC are significantly less productive of mucus and the newly regenerated ciliated pseudostratified columnar epithelial cells PCEC regrow normally functioning cilia C, which more easily expel mucus M. The reduction in mucus volume is felt directly by the patient, whose cough and airway obstruction are reduced. Over the ensuing weeks, this translates into a reduction in exacerbations and an improved quality of life.

Figure 3:
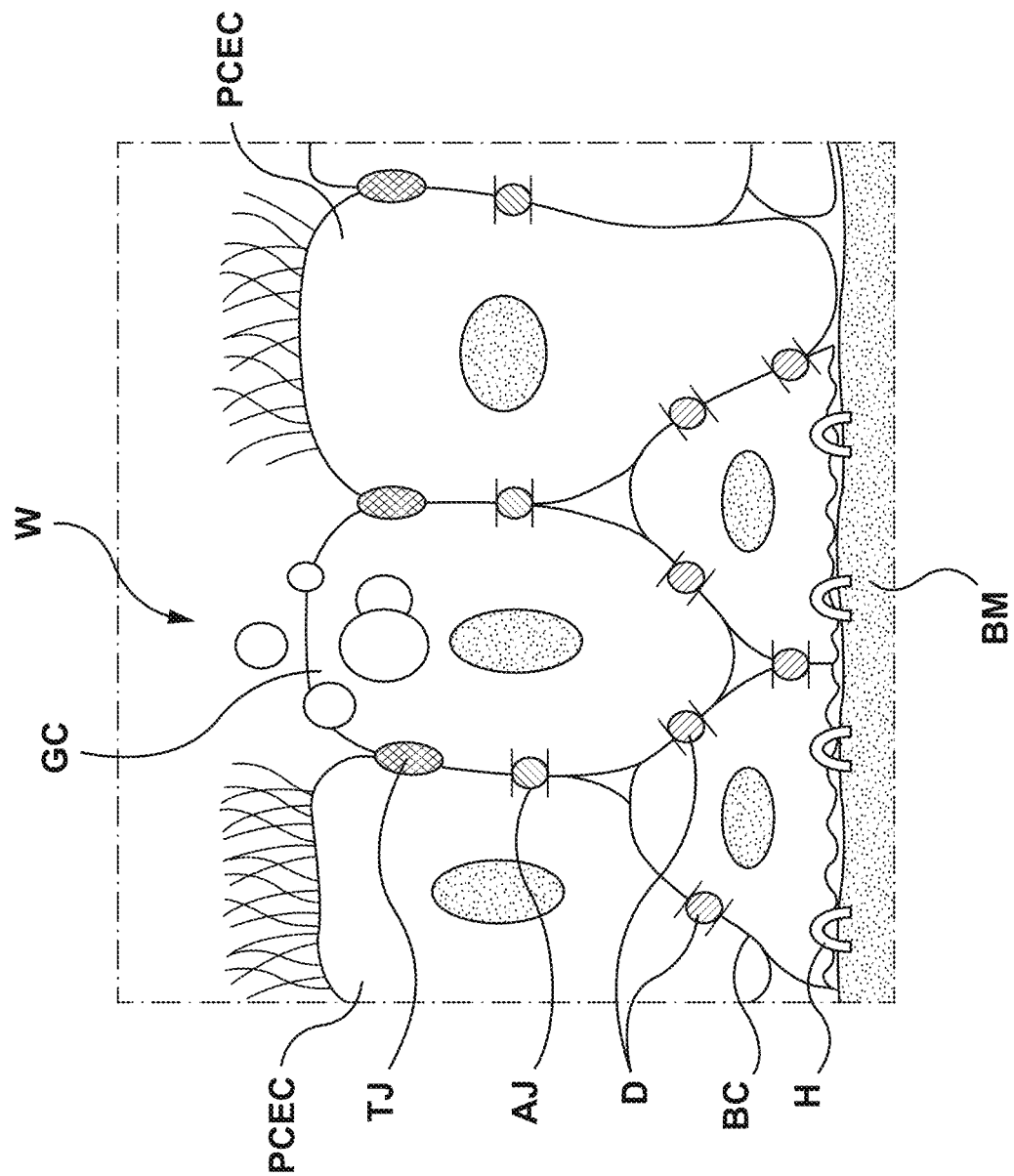
FIG. 3 provides a cross-sectional illustration of the epithelium of an airway wall showing types of cellular connection within the airway.
Figure 4B:
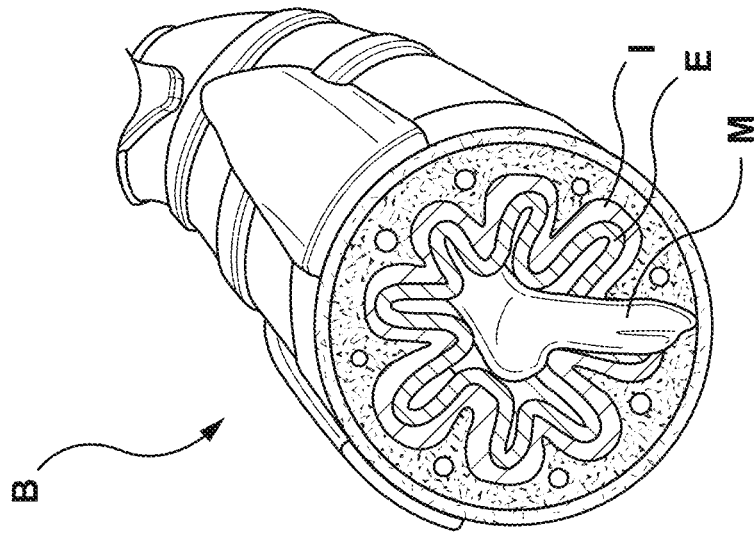
FIGS. 4A-4B depict bronchial airways in healthy and diseased states, respectively.
Figure 4A:
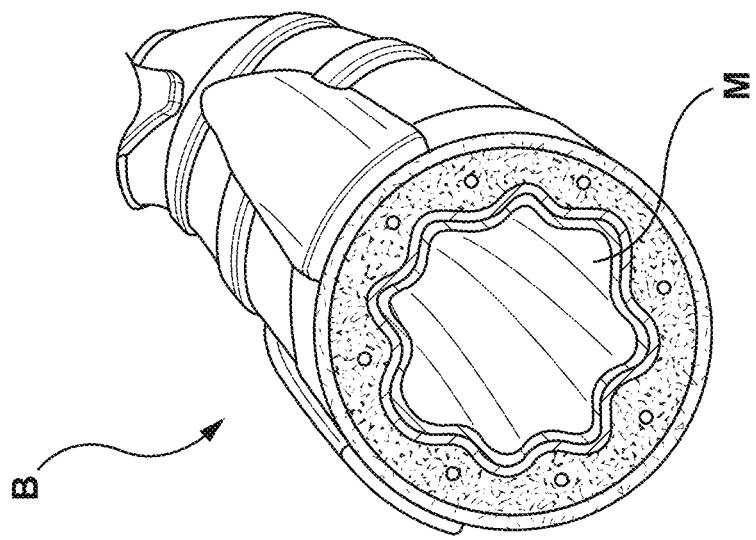

In some embodiments, the energy induces epithelial separation between the basal cells BC and more superficial goblet GC and ciliated pseudostratified columnar epithelial cells PCEC because of the relative strength of the cell-cell connections. The basal cells BC are connected to the basement membrane BM by hemidesmosomes H (illustrated in FIG. 3) whereas the basal cells BC connect to the goblet cells GC and ciliated pseudostratified columnar epithelial cells PCEC via desmosomes D (illustrated in FIG. 3). The energy parameters and electrode configurations of the pulmonary tissue modification system can be designed such that the desmosomes connections D separate but the hemidesmosomes H remain intact, thereby removing the surface cells, leaving the basal cells BC substantially intact, and ready to regenerate epithelium. The regenerative process is faster than would normally occur in trauma or with a thermal ablative modality where the basement membrane BM is disrupted and necrosis ensues. Basement membrane disruption and necrosis, such as in thermal ablation procedures, can cause activation of inflammatory pathways including T cells, macrophages, IL-13, IL-4, monocytes, proteases, cytokines, and chemokines among others. With methods disclosed herein, there is no substantial disruption of the basement membrane BM, and little or no acute inflammation. This allows for regeneration of healthy new target tissue within days of the procedure. It may be appreciated that in other embodiments the energy output from the pulmonary tissue modification system may induce other or additional changes to the airway wall W, leading to regeneration of healthy target tissue.

Figure 5:
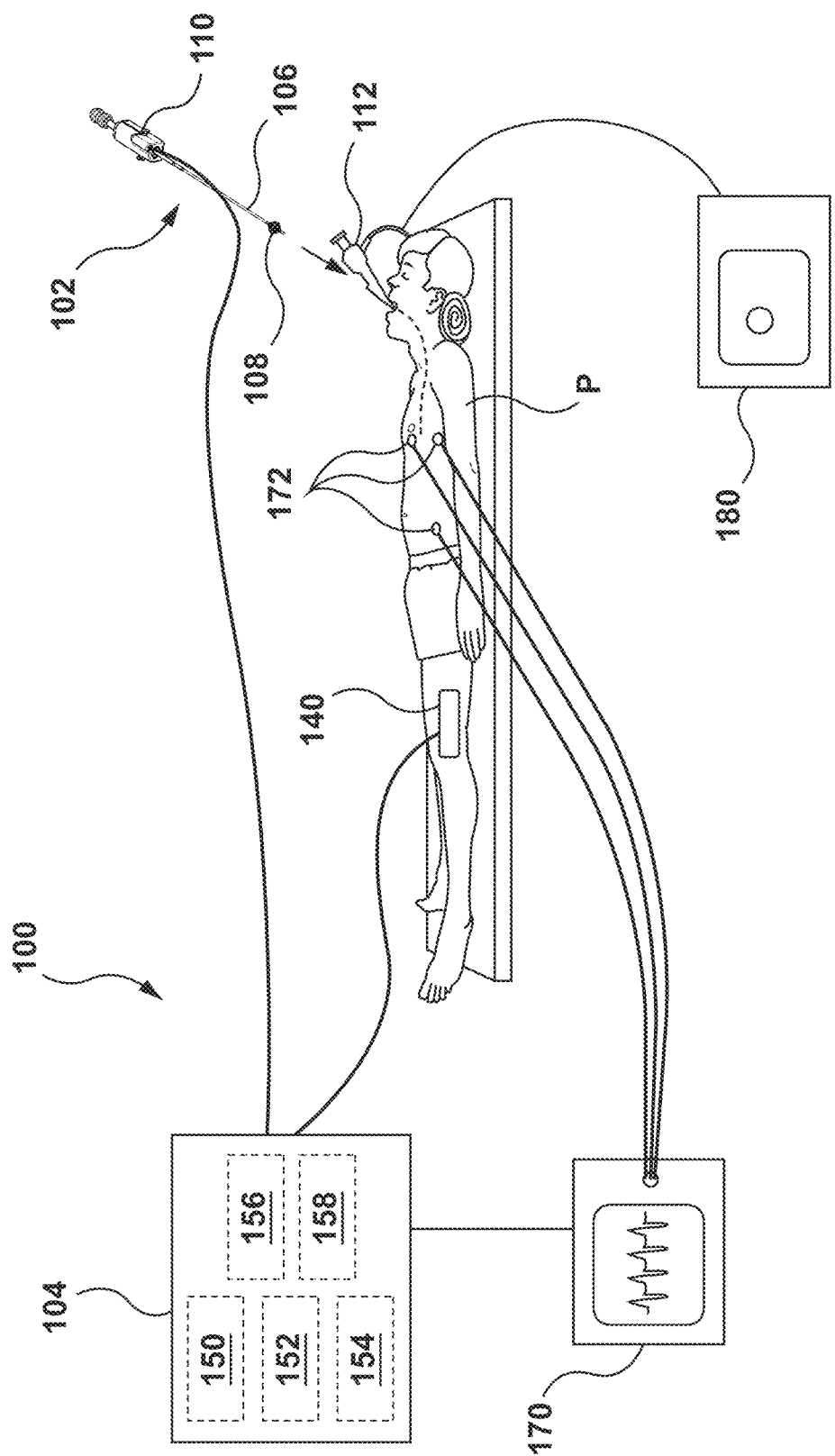
FIG. 5 illustrates an embodiment of a pulmonary tissue modification system used in treatment of a patient.

FIG. 5 illustrates an embodiment of a pulmonary tissue modification system 100 used in treatment of a patient P. In this embodiment, the system 100 comprises a therapeutic energy delivery catheter 102 connectable to a generator 104. The catheter 102 comprises an elongate shaft 106 having at least one energy delivery body 108 near its distal end and a handle 110 at its proximal end. Connection of the catheter 102 to the generator 104 provides electrical energy to the energy delivery body 108, among other features. The catheter 102 is insertable into the bronchial passageways of the patient P by a variety of methods, such as through a lumen in a bronchoscope 112, as illustrated in FIG. 5.

Figure 6:
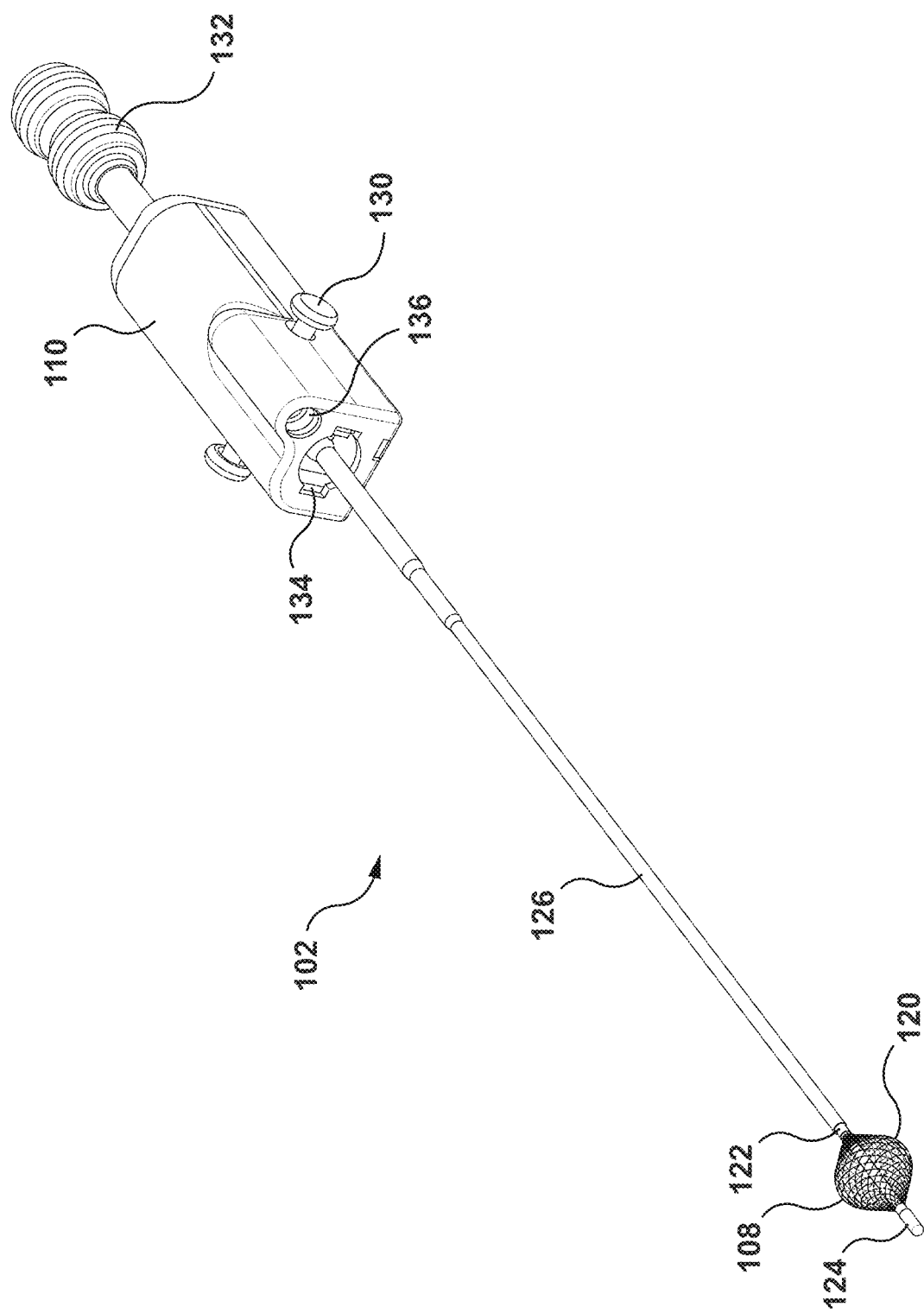
FIG. 6 provides a closer view of the embodiment of the therapeutic energy delivery catheter illustrated in FIG. 5.

FIG. 6 provides a closer view of the embodiment of the therapeutic energy delivery catheter 102 illustrated in FIG. 5. In this embodiment, the energy delivery body 108 comprises a single monopolar delivery electrode, however it may be appreciated that other types, numbers and arrangements may be used, further examples of which will be provided herein. In this embodiment, the energy delivery body 108 is comprised of a plurality of wires or ribbons 120 constrained by a proximal end constraint 122 and a distal end constraint 124 forming a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. In some embodiments, the energy delivery body 108 is self-expandable and delivered to a targeted area in a collapsed configuration. This collapsed configuration can be achieved, for example, by placing a sheath 126 over the energy delivery body 108. In FIG. 6, the catheter shaft 106 (within the sheath 126) terminates at the proximal end constraint 122, leaving the distal end constraint 124 essentially unconstrained and free to move relative to the shaft 106 of the catheter 102. Advancing the sheath 126 over the energy delivery body 108 allows the distal end constraint 124 to move forward, thereby lengthening/collapsing and constraining the energy delivery body 108.

The catheter 102 includes a handle 110 at its proximal end. In some embodiments, the handle 110 is removable, such as by pressing a handle removal button 130. In this embodiment, the handle 110 includes an energy delivery body manipulation knob 132 wherein movement of the knob 132 causes expansion or retraction/collapse of the basket-shaped electrode. In this example, the handle 110 also includes a bronchoscope working port snap 134 for connection with the bronchoscope 112 and a cable plug-in port 136 for connection with the generator 104.

Referring back to FIG. 5, in this embodiment, the therapeutic energy delivery catheter 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the catheter 102 and the return electrode 140. It may be appreciated that bipolar energy delivery and other arrangements may alternatively be used, as will be described in further detail herein. In this embodiment, the generator 104 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, but as new technology is developed any suitable element may be used. In addition, one or more communication ports are included.

It may be appreciated that in some embodiments, the generator 104 is comprised of three sub-systems; 1) a high energy storage system, 2) a high voltage, medium frequency switching amplifier, and 3) the system control, firmware, and user interface. The system controller includes a cardiac synchronization trigger monitor that allows for synchronizing the pulsed energy output to the patient's cardiac rhythm. The generator takes in AC (alternating current) mains to power multiple DC (direct current) power supplies. The generator's controller instructs the DC power supplies to charge a high-energy capacitor storage bank before energy delivery is initiated. At the initiation of therapeutic energy delivery, the generator's controller, high-energy storage banks and a bi-phasic pulse amplifier operate simultaneously to create a high-voltage, medium frequency output.

The processor 154 can be, for example, a general-purpose processor, a field programmable gate array (FPGA), an application specific integrated circuit (ASIC), a digital signal processor (DSP), and/or the like. The processor 154 can be configured to run and/or execute application processes and/or other modules, processes and/or functions associated with the system 100, and/or a network associated with the system 100.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a FPGA, an ASIC, a DSP) and/or software-based module (e.g., a module of computer code stored in memory and/or executed at the processor) capable of performing one or more specific functions associated with that module.

The data storage/retrieval unit 156 can be, for example, a random access memory (RAM), a memory buffer, a hard drive, a database, an erasable programmable read-only memory (EPROM), an electrically erasable read-only memory (EEPROM), a read-only memory (ROM), flash memory, and/or so forth. The data storage/retrieval unit 156 can store instructions to cause the processor 154 to execute modules, processes and/or functions associated with the system 100.

Some embodiments the data storage/retrieval unit 156 comprises a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) can be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as ASICs, Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, code used to produce a web service, and files containing higher-level instructions that are executed by a computer using an interpreter. For example, embodiments can be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the system 100 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

The user interface 150 can include a touch screen and/or more traditional buttons to allow for the operator to enter patient data, select a treatment algorithm (i.e. energy delivery algorithm 152), initiate energy delivery, view records stored on the storage/retrieval unit 156, or otherwise communicate with the generator 104.

Any of the systems disclosed herein can include a user interface 150 configured to allow operator-defined inputs. The operator-defined inputs can include duration of energy delivery or other timing aspects of the energy delivery pulse, power, target temperature, mode of operation, or a combination thereof. For example, various modes of operation can include system initiation and self-test, operator input, algorithm selection, pre-treatment system status and feedback, energy delivery, post energy delivery display or feedback, treatment data review and/or download, software update, or a combination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104 Here, the cardiac monitor 170 is used to continuously acquire the ECG. External electrodes 172 may be applied to the patient P and to acquire the ECG. The generator 104 analyzes one or more cardiac cycles and identifies the beginning of a time period where it is safe to apply energy to the patient P, thus providing the ability to synchronize energy delivery with the cardiac cycle. In some embodiments, this time period is within milliseconds of the R wave to avoid induction of an arrhythmia which may occur if the energy pulse is delivered on a T wave. It may be appreciated that such cardiac synchronization is typically utilized when using monopolar energy delivery, however it may be utilized in other instances.

In some embodiments, the processor 154, among other activities, modifies and/or switches between the energy-delivery algorithms, monitors the energy delivery and any sensor data, and reacts to monitored data via a feedback loop. It may be appreciated that in some embodiments the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data related to the treatments delivered and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154. Examples algorithms will be described in detail herein below. In some embodiments, the catheter 102 includes one or more sensors 160 that can be used to determine temperature, impedance, resistance, capacitance, conductivity, permittivity, and/or conductance, to name a few. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It may be appreciated that any of the systems disclosed herein can include an automated treatment delivery algorithm that could dynamically respond and adjust and/or terminate treatment in response to inputs such as temperature, impedance, treatment duration or other timing aspects of the energy delivery pulse, treatment power and/or system status.

In some embodiments, imaging is achieved with the use of a commercially-available system, such as a bronchoscope 112 connected with a separate imaging screen 180, as illustrated in FIG. 5. It may be appreciated that imaging modalities can be incorporated into the catheter 102 or used alongside or in conjunction with the catheter 102. The imaging modality can be mechanically, operatively, and/or communicatively coupled to the catheter 102 using any suitable mechanism.

Figure 7:
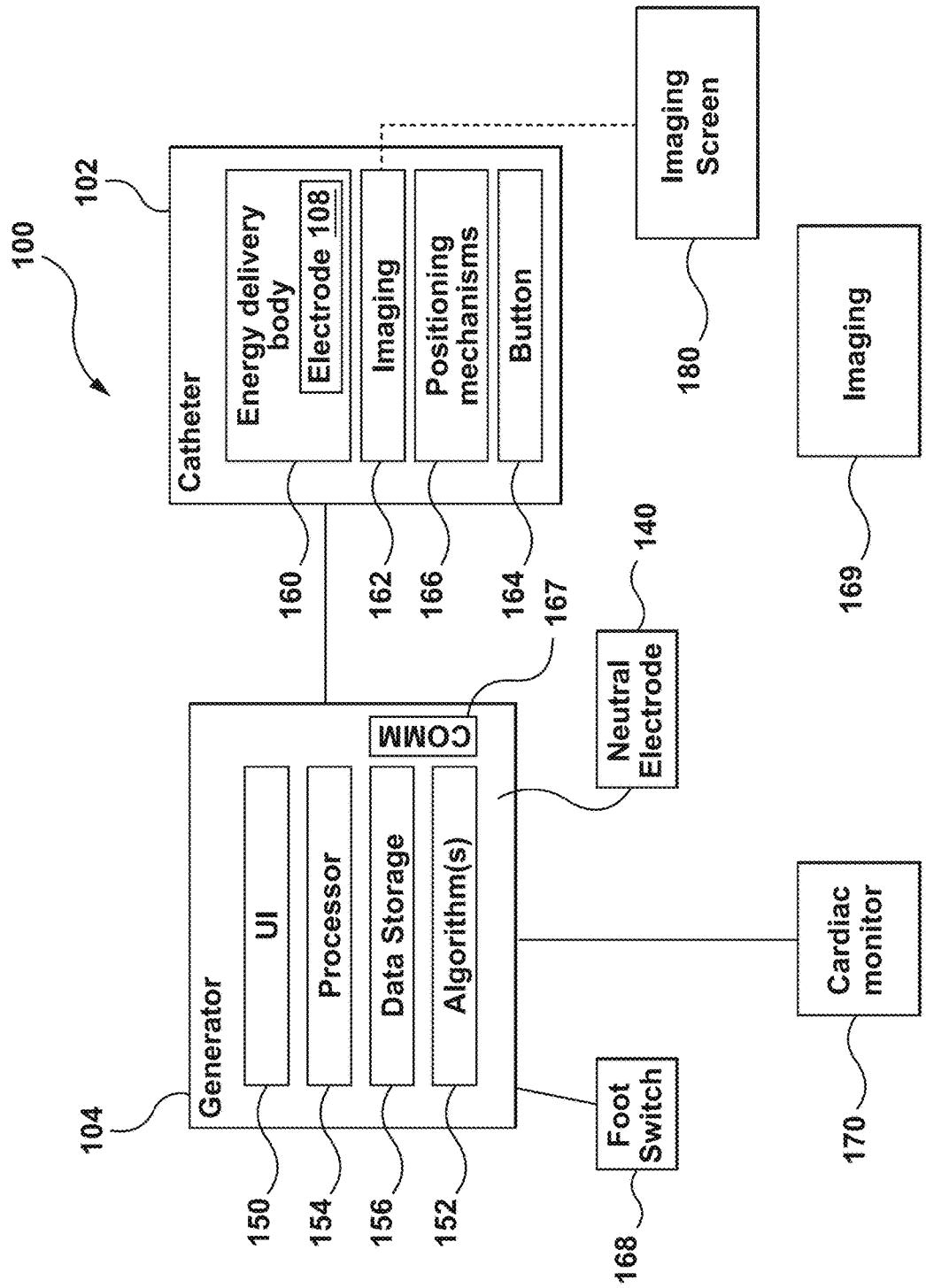
FIG. 7 is a schematic illustration of an embodiment of a pulmonary tissue modification system.

FIG. 7 is a schematic illustration of an embodiment of a pulmonary tissue modification system 100. In this embodiment, the catheter 102 is configured for monopolar energy delivery. As shown, a dispersive (neutral) or return electrode 140 is operatively connected to the generator 104 while affixed to the patient's skin to provide a return path for the energy delivered via the catheter 102. The energy-delivery catheter 102 includes one or more energy delivery bodies 108 (comprised of electrode(s)), one or more sensors 160, one or more imaging modalities 162, one or more buttons 164, and/or positioning mechanisms 166 (e.g., such as, but not limited to, levers and/or dials on a handle with pull wires, telescoping tubes, a sheath, and/or the like) the one or more energy delivery bodies 108 into contact with the tissue. In some embodiments, a foot switch 168 is operatively connected to the generator 104 and used to initiate energy delivery.

As mentioned previously, the user interface 150 can include a touch screen and/or more traditional buttons to allow for the operator to enter patient data, select a treatment algorithm 152, initiate energy delivery, view records stored on the storage/retrieval unit 156, or otherwise communicate with the generator 104. The processor 154 manages and executes the energy-delivery algorithm, monitors the energy delivery and any sensor data, and reacts to monitored data via a feedback loop. The data storage/retrieval unit 156 stores data related to the treatments delivered and can be downloaded by connecting a device (e.g., a laptop or thumb drive) to a communication port 167.

The catheter 102 is operatively connected to the generator 104 and/or a separate imaging screen 180. Imaging modalities 162 can be incorporated into the catheter 102 or used alongside or in conjunction with the catheter 102. Alternatively or in addition, a separate imaging modality or apparatus 169 can be used, such as a commercially-available system (e.g., a bronchoscope). The separate imaging apparatus 169 can be mechanically, operatively, and/or communicatively coupled to the catheter 102 using any suitable mechanism.

Figure 8A:
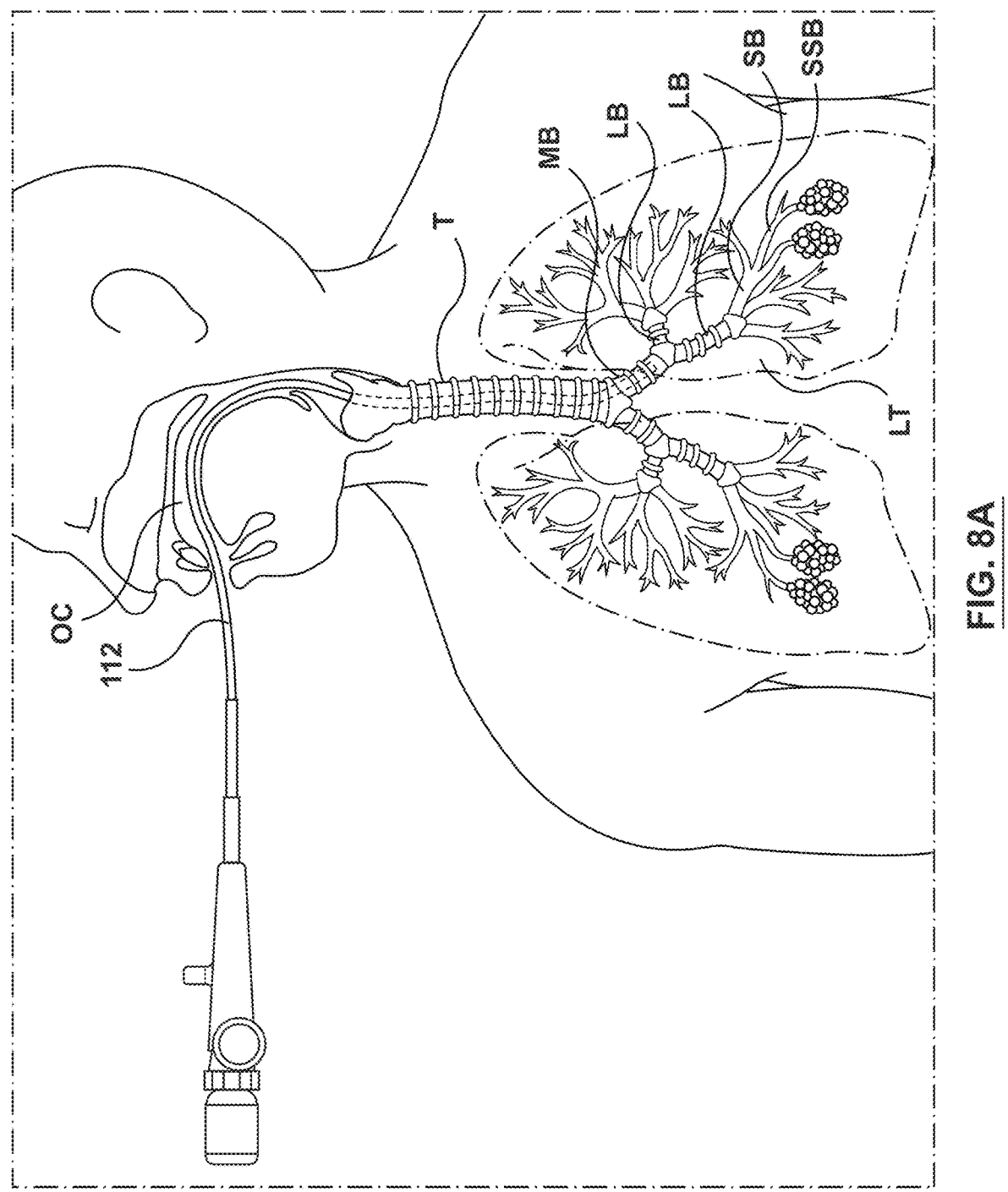
FIGS. 8A-8B illustrate a bronchoscope inserted in the mouth/oral cavity of the patient and the nose/nasal cavity of the patient, respectively.
Figure 8B:
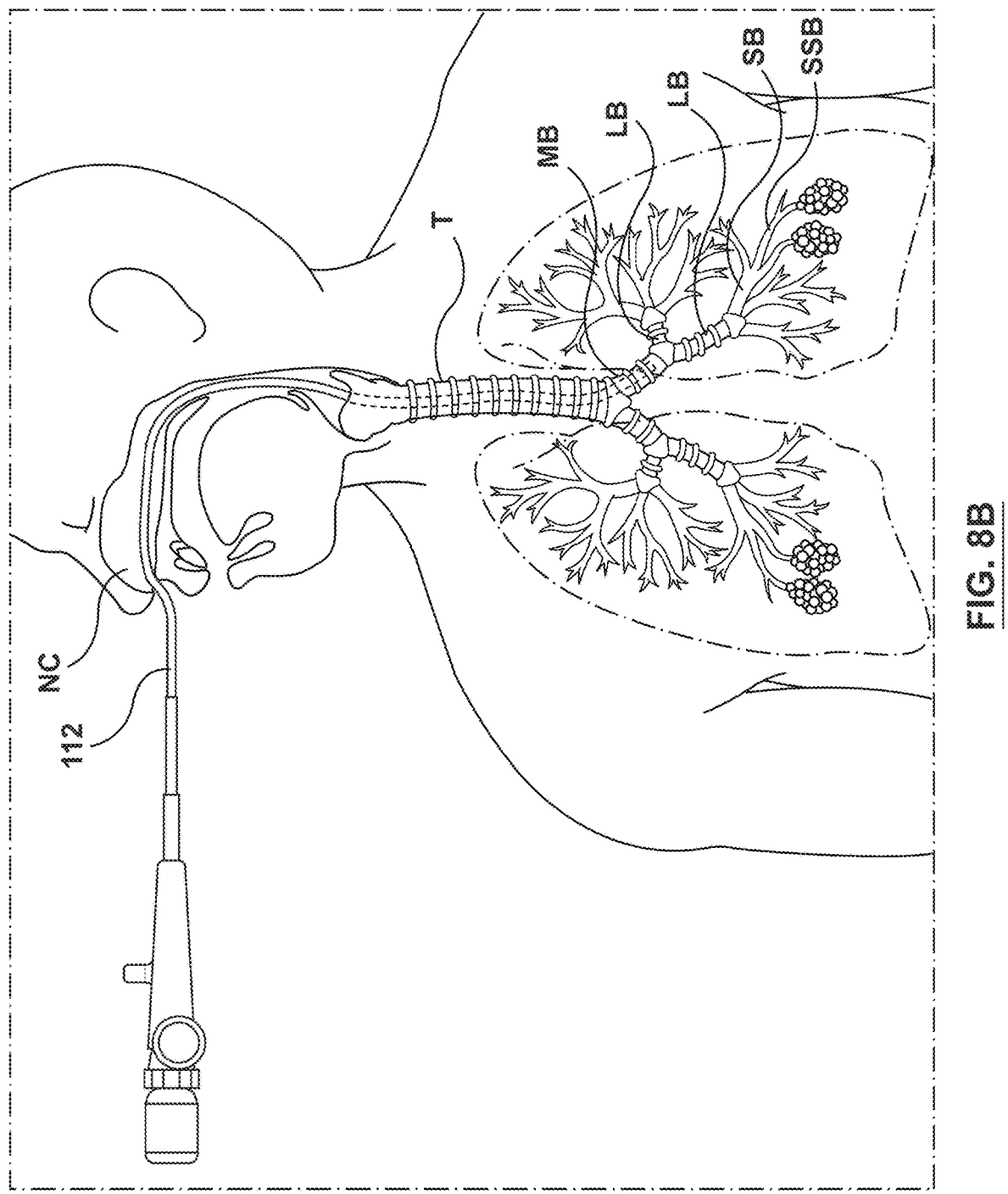

Referring to FIG. 8A, a bronchoscope 112 is inserted in the mouth or oral cavity OC of the patient P. It may be appreciated that methods for accessing the airway can include use of other natural orifices such as the nose or nasal cavity NC (illustrated in FIG. 8B). Alternatively, a suitable artificial orifice may be used (not shown e.g., stoma, tracheotomy). Use of the bronchoscope 112 allows for direct visualization of the target tissues and the working channel of the bronchoscope 112 can be used to deliver the catheter 102 as per the apparatuses and systems disclosed herein, allowing for visual confirmation of catheter placement and deployment. FIGS. 8A-8B illustrate advancement of the distal end of the catheter 102 into the trachea T and the mainstem bronchi MB, though it may be appreciated that the catheter 102 may be advanced into the lobar bronchi LB, more distal segmental bronchi SB and sub-segmental bronchi SSB if desired.

Figure 9:
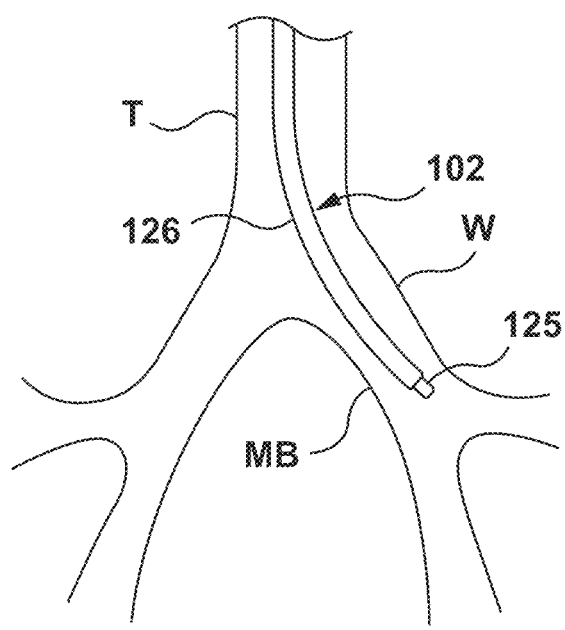
FIGS. 9, 10, 11 illustrate positioning of the distal end of the catheter into the mainstem bronchi for treatment of the airway.
Figure 10:
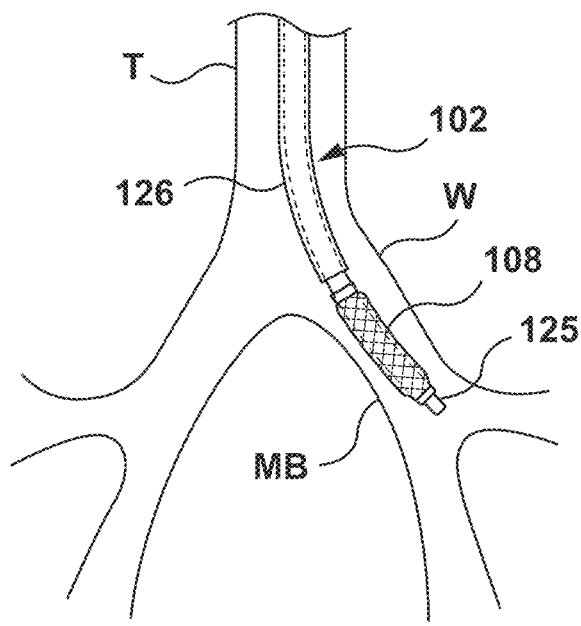
Figure 11:
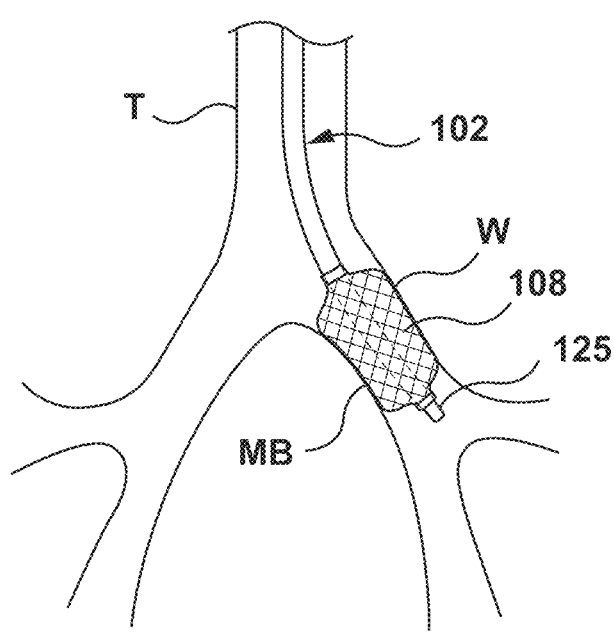

FIGS. 9-11 illustrate positioning of the distal end of the catheter 102 into the mainstem bronchi MB for treatment of the airway. In some embodiments, the catheter 102 has an atraumatic tip 125 to allow advancement through the airways without damaging or the airway walls W. FIG. 9 illustrates the catheter 102 advanced into the mainstem bronchi MB while the sheath 126 is covering the energy delivery body 108. Positioning of the catheter 102 may be assisted by various imaging techniques. For example, the bronchoscope 112 may be used to provide real-time direct visual guidance to the target site and may be used to observe accurate positioning of the catheter 102 before, during and after the delivery of treatment. FIG. 10 illustrates withdrawal of the sheath 126, exposing the energy delivery body 108. It may be appreciated that in some embodiments, the energy delivery body 108 is self-expanding so that the sheath 126 holds the energy delivery body 108 in a collapsed configuration. In such embodiments, withdrawal of the sheath 126 releases the energy delivery body 108, allowing self-expansion. In other embodiments, the energy delivery body 108 is expanded by other mechanisms, such as movement of the knob 132, which may occur after the sheath 126 is withdrawn. FIG. 11 illustrates the basket-shaped energy delivery body 108 in an expanded configuration, wherein the energy delivery body 108 contacts the airway walls W. Additional imaging can be used to verify positioning and/or make additional measurements (e.g., depth).

Once the energy delivery body 108 is desirably positioned, treatment energy is provided to the airway wall W by the energy delivery body 108. The treatment energy is applied according to at least one energy delivery algorithm.

In some embodiments, the user interface 150 on the generator 104 is used to select the desired treatment algorithm 152. In other embodiments, the algorithm 152 is automatically selected by the generator 104 based upon information obtained by one or more sensors on the catheter 102, which will be described in more detail in later sections. A variety of energy delivery algorithms may be used. In some embodiments, the algorithm 152 generates a signal having a waveform comprising a series of energy packets with rest periods between each packet, wherein each energy packet comprises a series of high voltage pulses. In some embodiments, each high voltage pulse is between about 500 V to 10 kV, or about 500 V to about 5,000 V, including all values and subranges in between. In some embodiments, the energy provided is within the frequency range of about 10 kHz to about 10 MHz, or about 100 kHz to about 1 MHz, including all values and subranges in between. The algorithm 152 delivers energy to the walls of the airway so as to provide the desired treatment with minimal or no tissue heating. In some embodiments, a temperature sensor is used to measure electrode and/or tissue temperature during treatment to ensure that energy deposited in the tissue does not result in any clinically significant tissue heating. For example, a temperature sensor can monitor the temperature of the tissue and/or electrode, and if a pre-defined threshold temperature is exceeded (e.g., 65° C.), the generator can alter the algorithm to automatically cease energy delivery or modify the algorithm to reduce temperature to below the pre-set threshold. For example, if the temperature exceeds 65° C., the generator can reduce the pulse width or increase the time between pulses and/or packets in an effort to reduce the temperature. This can occur in a pre-defined step-wise approach, as a percentage of the parameter, or by other methods.

Conventional radiofrequency ablation (RFA) kills cells by application of high frequency alternating current in the 350-550 kHz range, generating heat in the tissue to product thermal necrosis of the cells. Many RFA devices have been developed to treat cardiac arrhythmias, solid tumors, renal nerves, and others. Microwave ablation is another thermal ablation modality in which 300 MHz to 300 GHz alternating current is used, also leading to thermal necrosis. This energy source is employed to target solid tumors because of the large ablation zones and uniform heating. In general, heat-related thermal ablation denatures the proteins within the tissue, causes a significant inflammatory response and can be difficult to control, often leading to injury to non-target tissues. For certain types of treatments (e.g., tumor treatments), inflammation is acceptable, but when focused within the pulmonary airways, substantive inflammation can lead to serious complications (e.g., exacerbation). While the denaturation of proteins alone may or may not produce clinical morbidity, more intact, less denatured proteins allow for the opportunity to enhance the host response to various challenges to the immune system, whether that is to affect pathogens, tumor, etc. These limitations especially make heat-related thermal ablation in the airways less desirable.

In contrast, the algorithm 152 prescribes energy delivery to the airway walls W which is non-thermal, thereby reducing or avoiding inflammation. In some embodiments, the algorithm 152 is tailored to affect tissue to a pre-determined depth and/or to target specific types of cells within the airway wall. In some embodiments, the generator has several fixed algorithm settings whereby the targeted cell depth is reflected in each setting. For instance, one setting/algorithm may primarily affect the pathogens resident in the mucus layer, another setting/algorithm may target the epithelium, another setting/algorithm may primarily target the epithelium, basement membrane, submucosa and/or smooth muscle, while yet another setting/algorithm may primarily target the epithelium, basement membrane, submucosa, smooth muscle, submucosal glands and/or nerves. In some embodiments, treatment is performed at the same location, but in others, the operator may choose to affect certain cell types at different locations. The setting utilized by the operator may be dependent on the physiologic nature of the patient's condition.

The biological mechanisms and cellular processes by which the energy removes the cells will be described in more detail in later sections. The energy treats the airway wall W at the target location in a manner which allows the regeneration of healthy tissue. For example, normal goblet cells GC and normal ciliated pseudostratified columnar epithelial cells PCEC are able to regenerate, thereby inducing reverse remodeling of the disease to reduce the mucus hypersecretion. The newly regenerated goblet cells GC are significantly less productive of mucus and the newly regenerated ciliated pseudostratified columnar epithelial cells PCEC regrow normally functioning cilia C, which more easily expel mucus M. Thus, healthy new target tissue can be regenerated within days of the procedure. This dramatically reduces symptoms of cough and mucus hypersecretion in patients which results in fewer and less severe exacerbations and improvement in quality of life.

Figure 12:
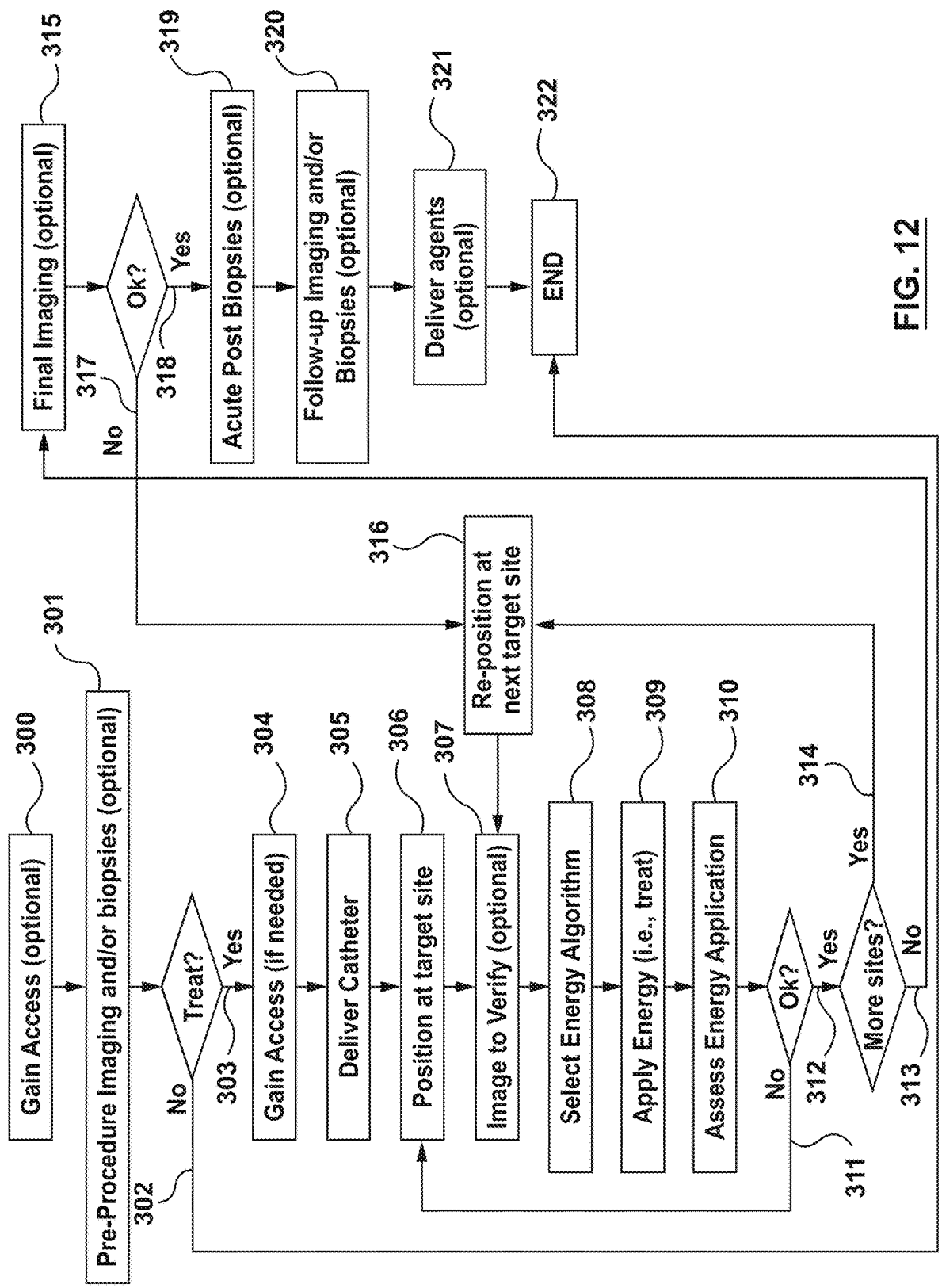
FIG. 12 is a flowchart illustrating methods described herein in a step-wise approach to treating patients.

FIG. 12 is a flowchart illustrating methods described herein in a step-wise approach to treating patients, wherein the methods are executed by a practitioner, therapeutic energy-delivery catheter, or generator as appropriate. In some embodiments, one or more of the steps disclosed herein can be optional. The first series of steps can be used to assess patient anatomy and/or suitability for the procedure to decide whether or not to treat. In some embodiments, this assessment can be optional, but can include one or more of the following steps. First, gain access 300 to the airway (if needed). Second, perform any suitable pre-procedural imaging, sputum sampling and/or biopsies that can be necessary and/or desired 301. Pre-procedural imaging can include a non-invasive CT scan, bronchoscopy, confocal laser endomicroscopy (CLE), optical coherence tomography (OCT) or any other appropriate technique along with any measurements that can be taken (e.g., depth). Sputum sampling can include nasal mucosa brushing, nasal washing, bronchial brushing, bronchial washing, and/or bronchoalveolar lavage. Then, decide whether or not to treat the patient. If the decision is 'No' 302, go to END 322. If the decision is 'Yes' 303, gain access, if needed 304. In some embodiments, the treatment can be performed one or more days after the pre-procedure assessment. In this embodiment, it would be required to gain access 304.

In some embodiments, the treatment can be performed immediately after the pre-procedure assessment. In this embodiment, it may not be necessary to gain access again. In this embodiment, the next step 305 of the procedure is to deliver the catheter. As described above, the catheter can be delivered by various methods, however, for the purposes of providing an example, the catheter is delivered via a working channel of a bronchoscope. In the next step 306, the catheter is positioned at a target site. Again, as an example, the bronchoscope can be used to provide real-time direct visual guidance to the target site and be used to observe accurate positioning of the catheter. This can include placement of one or more energy delivery bodies into contact with the airway wall. Additional imaging 307 can then be used to verify positioning and/or make additional measurements (e.g., depth). At the next step 308, the operator can optionally select the desired energy delivery algorithm 152. As described in detail above, this can include for example, selecting an algorithm based on target depth of treatment. Alternatively, the generator is configured to apply a pre-defined algorithm suitable for most patients. In this embodiment, the next step 309 is to execute or apply the energy delivery algorithm. This can be accomplished via a foot pedal or other mechanism described herein. After the energy is applied, the operator can assess the energy application 310. This can include performing additional imaging with or without measurements and/or reacting to messages communicated by the generator (e.g., an error with the energy delivery that can have led to incomplete treatment). If the treatment is not acceptable 311, then operator would go back to the Position at Target Site step 306. If the treatment is acceptable 312, then operator would proceed. The next step in the procedure can be to determine if more treatment sites are to be treated. If 'No' 313, the operator would then move on to Final Imaging 315 and the remaining steps until END 322. If 'Yes' 314, the operator would then re-position at the next target site 316 and repeat the steps for applying a treatment. Once all treatments are complete, the operator then moves on to optional Final Imaging 315, where the operator can perform additional confirmatory imaging to ensure all targeting areas were treated to his/her satisfaction. If 'No' 317, the operator would proceed back to 'Re-position at next target site' 316 and perform additional treatments. If 'Yes' 318, the operator can then decide to perform one or more acute biopsies and/or sputum samples 319 to compare to any pre-procedure biopsies and/or sputum samples 301 that can have been taken. At a later date, follow-up imaging and/or, biopsies, and/or sputum samples 320 can be taken and compared to any other images or, biopsies, and/or sputum samples to help assess and/or document the outcome of the therapy. The operator can then decide to deliver materials, active agents, etc. 321 to assist in the normative healing process and as such further reduce the potential for pen-procedural issues or complications. Moreover, this might further reduce the degree or frequency of exacerbations, especially in the short term. Some examples of these agents include isotonic saline gel, medicated films, antibacterials, antivirals, antifungals, anti-inflammatories, etc. As a result of exposing the tissue(s) to high-energy fields, the treated tissue(s) can be conditioned for improved agent uptake. The procedure then ends 322. The patient can then continue to be followed by a physician and can undergo this entire procedure again, should the disease or disorder recur and/or continue.

Thus, it is contemplated that in certain embodiments where the desired clinical effect was not achieved or where it was achieved but then subsequently the condition re-occurred, repeat procedures may be desired. In these embodiments, it might be desired not only to re-treat certain areas but also to target a different portion of the pulmonary anatomy. Thus, the system 100 may be used to specifically re-treat the same portion of tissue as the original treatment or a distinctly different potion of tissue from the first intervention.

While various embodiments have been described above, it should be understood that they have been presented by way of example, and not limitation. Where methods described above indicate certain events occurring in certain order, the ordering of certain events can be modified. Additionally, certain of the events can be performed concurrently in a parallel process when possible, as well as performed sequentially as described above.

II. ENERGY DELIVERY ALGORITHMS

As mentioned previously, one or more energy delivery algorithms 152 are programmable, or can be pre-programmed, into the generator 104 for delivery to the patient P. The one or more energy delivery algorithms 152 specify electric signals which provide energy delivered to the airway walls W which are non-thermal, reducing or avoiding inflammation. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the catheter 102 (particularly the one or more energy delivery bodies 108), and/or the choice of monopolar or bipolar energy delivery. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger surface area thus requiring a lower voltage to achieve the treatment effect, compare to monopolar. Likewise, this lower voltage may be used to reduce the depth of penetration, such as to affect the epithelial cells rather than the submucosal cells. In addition, lower voltage requirements may obviate the use of cardiac synchronization if the delivered voltage is low enough to avoid stimulation of the cardiac muscle cells.

It may be appreciated that a variety of energy delivery algorithms 152 may be used. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the frequency of each pulse, to name a few. There may be a fixed rest period between packets, or packets may be gated to the cardiac cycle and are thus variable with the patient's heart rate. A feedback loop based on sensor information and an auto-shutoff specification, and/or the like, may be included.

Figure 13:
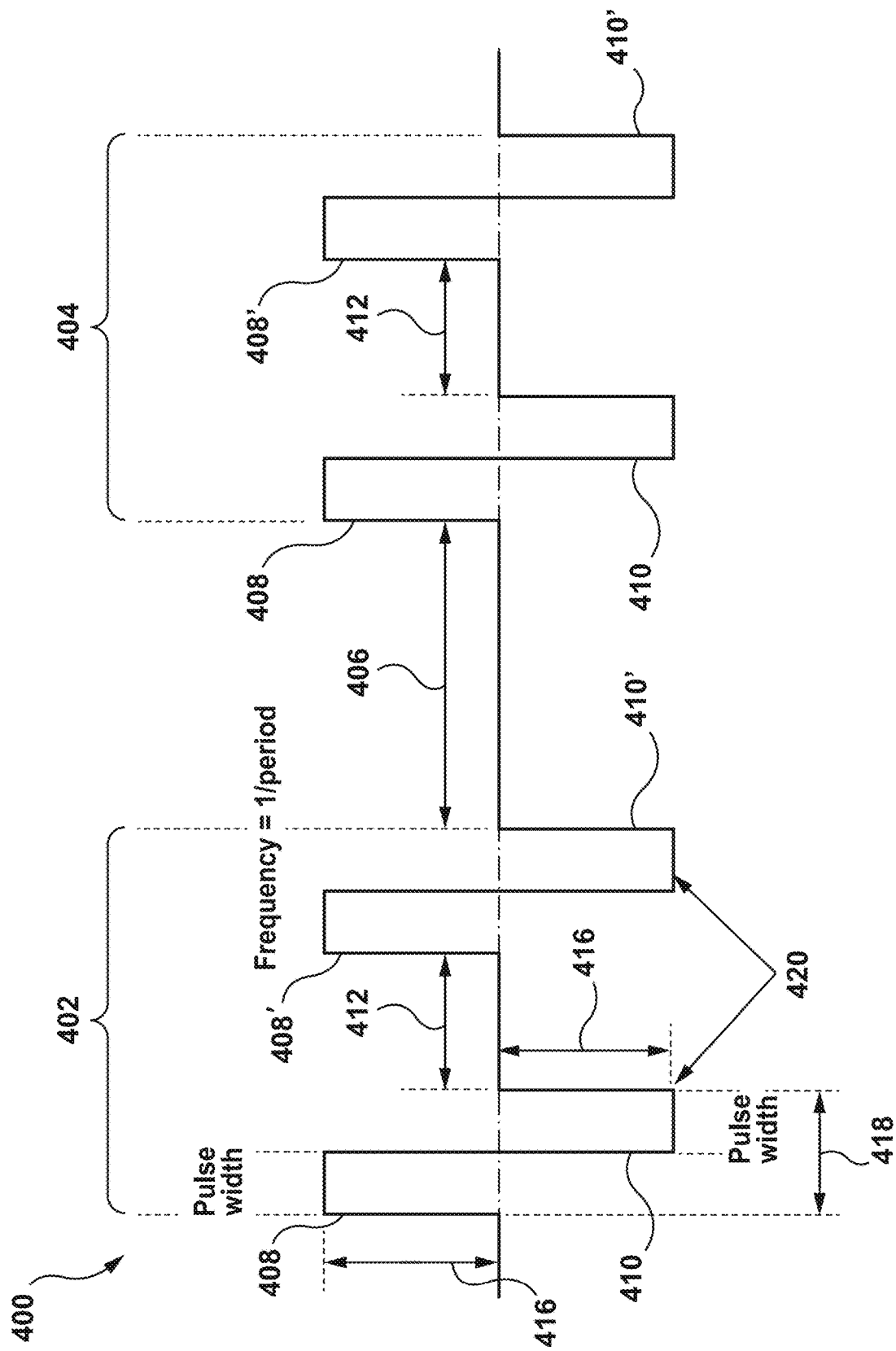
FIG. 13 illustrates an embodiment of a waveform of a signal provided by an energy delivery algorithm.

FIG. 13 illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic pulse (comprising a first positive peak 408 and a first negative peak 410) and a second biphasic pulse (comprising a second positive peak 408' and a second negative peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave. The positive voltage wave causes cellular depolarization in which the normally negatively charged cell briefly turns positive. The negative voltage wave causes cellular hyperpolarization in which the cell potential is negative.

In some embodiments, each high voltage pulse or the set voltage 416 is between about 500 V to 10 kV, particularly about 500 V to 4000 V. including all values and subranges in between. In some embodiments, each high voltage pulse is in range of approximately 1000 V to 2500 V which typically penetrates the airway wall W so as to treat or affect particular cells somewhat shallowly, such as epithelial cells. In some embodiments, each high voltage pulse is in the range of approximately 2600 V to 4000 V which typically penetrates the airway W so as to treat or affect particular cells somewhat deeply positioned, such as submucosal cells or smooth muscle cells. It may be appreciated that the set voltage 416 may vary depending on whether the energy is delivered in a monopolar or bipolar fashion. In some embodiments, the energy is delivered in a monopolar fashion and each high voltage pulse is in the range of approximately 2000 V to 3500 V, more particularly 2500 V. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V.

It may be appreciated that in some embodiments the set voltage 416 is between about 50 V and about 4 kV or about 500 V and about 4 kV, including all values and subranges in between. And in other embodiments, the set voltage 416 is in a range of about 500 V to about 5 kV, including all values and subranges in between.

The number of pulses per unit of time is the frequency. In some embodiments, the signal has a frequency in the range 100 kHz-1 MHz. In some embodiments, the signal has a frequency in the range of approximately 100-500 kHz which typically penetrates the airway W so as to treat or affect particular cells somewhat deeply positioned, such as submucosal cells or smooth muscle cells. In some embodiments, the signal has a frequency in range of approximately 600 kHz-1 MHz which typically penetrates the airway wall W so as to treat or affect particular cells somewhat shallowly, such as epithelial cells. It may be appreciated that at frequencies at or below 300 kHz, undesired muscle stimulation may occur. Therefore, in some embodiments, the signal has a frequency in the range of 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation. In some embodiments, biphasic pulses are utilized to reduce undesired muscle stimulation, particularly cardiac muscle stimulation. It may be appreciated that even higher frequencies may be used with components which minimize signal artifacts.

In some embodiments, the time between packets, referred to as the rest period 406, is set between about 0.1 seconds and about 5 seconds, including all values and subranges in between. In other embodiments, the rest period 406 ranges from about 0.001 seconds to about 10 seconds, including all values and subranges in between. In some embodiments, the rest period 406 is approximately 1 second. In particular, in some embodiments the signal is synced with the cardiac rhythm so that each packet is delivered between heartbeats, thus the rest periods coincides with the heartbeats. In other embodiments wherein cardiac synchronization is utilized, the rest period 406 may vary, as the rest period between the packets can be influenced by cardiac synchronization, as will be described in later sections.

The cycle count 420 is the number of pulses within each packet. Referring to FIG. 13, the first packet 402 has a cycle count 420 of two (i.e. two biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count. The higher the cycle count, the longer the packet duration and the larger the quantity of energy delivered. In some embodiments, packet durations are in the range of approximately 50 to 100 microseconds, such as 50 µs, 60 µs, 70 µs, 80 µs, 90 µs or 100 µs.

The number of packets delivered during treatment, or packet count, may include 1 packet, 2 packets, 3 packets, 4 packets, 5 packets, 10 packets, 15 packets, 20 packets, up to 5 packets, up to 10 packets, up to 15 packets, up to 20 packets, up to 100 packets, or up to 1,000 packets, including all values and subranges in between. In some embodiments, 5 packets are delivered, wherein each packet has a packet duration of 100 microseconds and a set voltage of 2500 V. In some embodiments, 5 to 10 packets are delivered, wherein each packet has a packet duration of 100 microseconds and a set voltage of 2500 V, which results in a treatment effect that has increased uniformity. In some embodiments, less than 20 packets, wherein each packet has a packet duration of 100 microseconds and a set voltage of 2500 V, are delivered to avoid affecting the cartilage layer CL. In some embodiments, a total energy-delivery duration between 0.5 to 100 milliseconds at a set voltage of 2500 V can be optimal for the treatment effect.

In some embodiments, the dead time 412 is set between about 0 and about 500 nanoseconds, including all values and subranges in between. In other embodiments, the dead time 412 is in a range of approximately 0 to 10 microseconds, or about 0 to about 100 microseconds, or about 0 to about 100 milliseconds, including all values and subranges in between. In some embodiments, the dead time 412 is in the range of 0.2 to 0.3 microseconds.

It may be appreciated that the specific settings to desirably alter target tissue are dependent on one another and the electrode design. Therefore, the embodiments provided herein depict specific waveform examples, and it is within the scope of this invention to use multiple waveforms and/or characteristics in any combination to achieve the desired tissue effects. A first example combination of parameters for an energy signal comprises a frequency of 600 kHz, a voltage of 3000 V and a packet count of 10. A second example combination of parameters for an energy signal comprises a frequency of 600 kHz, a voltage of 2500 V and a packet count of 5. A third example combination of parameters for an energy signal comprises a frequency of 600 kHz, a voltage of 2300 V and a packet count of 20. The first example led to greater epithelial and submucosal gland treatment due to the higher voltage. The second example led to less epithelial and submucosal gland treatment due to the lower voltage and lower packet count. The third example, yielded a stronger epithelial treatment effect and a lower submucosal glad treatment effect, due to the higher packet count and a lower voltage. This supports that lower voltages do not penetrate deep enough to have the same treatment effect on submucosal glands than higher voltages.

Figure 14:
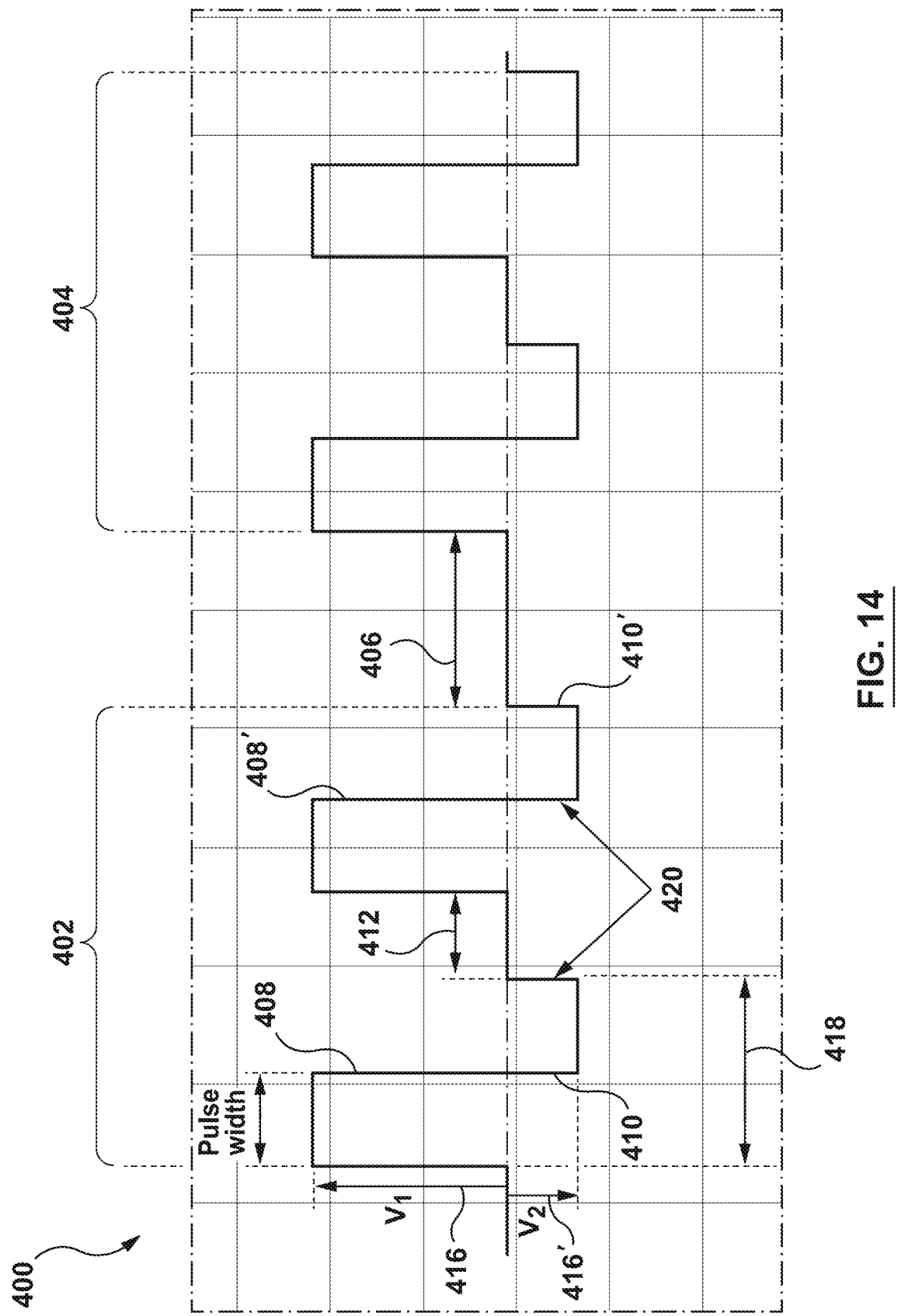
FIG. 14 illustrates an example waveform of another energy delivery algorithm.

FIG. 14 illustrates an example waveform 400 prescribed by another energy delivery algorithm 152. Here, two packets are shown, a first packet 402 and a second packet 404, wherein the packets 402, 404 are separated by a rest period 406. In this embodiment, each packet 402, 404 is comprised of a first biphasic pulse (comprising a first positive peak 408 and a first negative peak 410) and a second biphasic pulse (comprising a second positive peak 408' and a second negative peak 410'). The first and second biphasic pulses are separated by dead time 412 between each pulse. In this embodiment, the waveform 400 is asymmetric so that the set voltage is different for the positive and negative peaks. This asymmetrical waveform may result in a more consistent treatment effect as the dominant positive or negative amplitude leads to a longer duration of same charge cell membrane charge potential. In this embodiment, the first positive peak 408 has a set voltage 416 that is larger than the set voltage 416' of the first negative peak 410. In some embodiments, asymmetry also includes pulses having pulse widths of unequal duration. In some embodiments, the biphasic waveform is asymmetric such that the voltage in one direction (i.e., positive or negative) is greater than the voltage in the other direction but the length of the pulse is calculated such that the area under the curve of the depolarization equals the area under the curve of the hyperpolarization. Alternatively, the area under the curve of the depolarization and hyperpolarization may be unequal.

Figure 15:
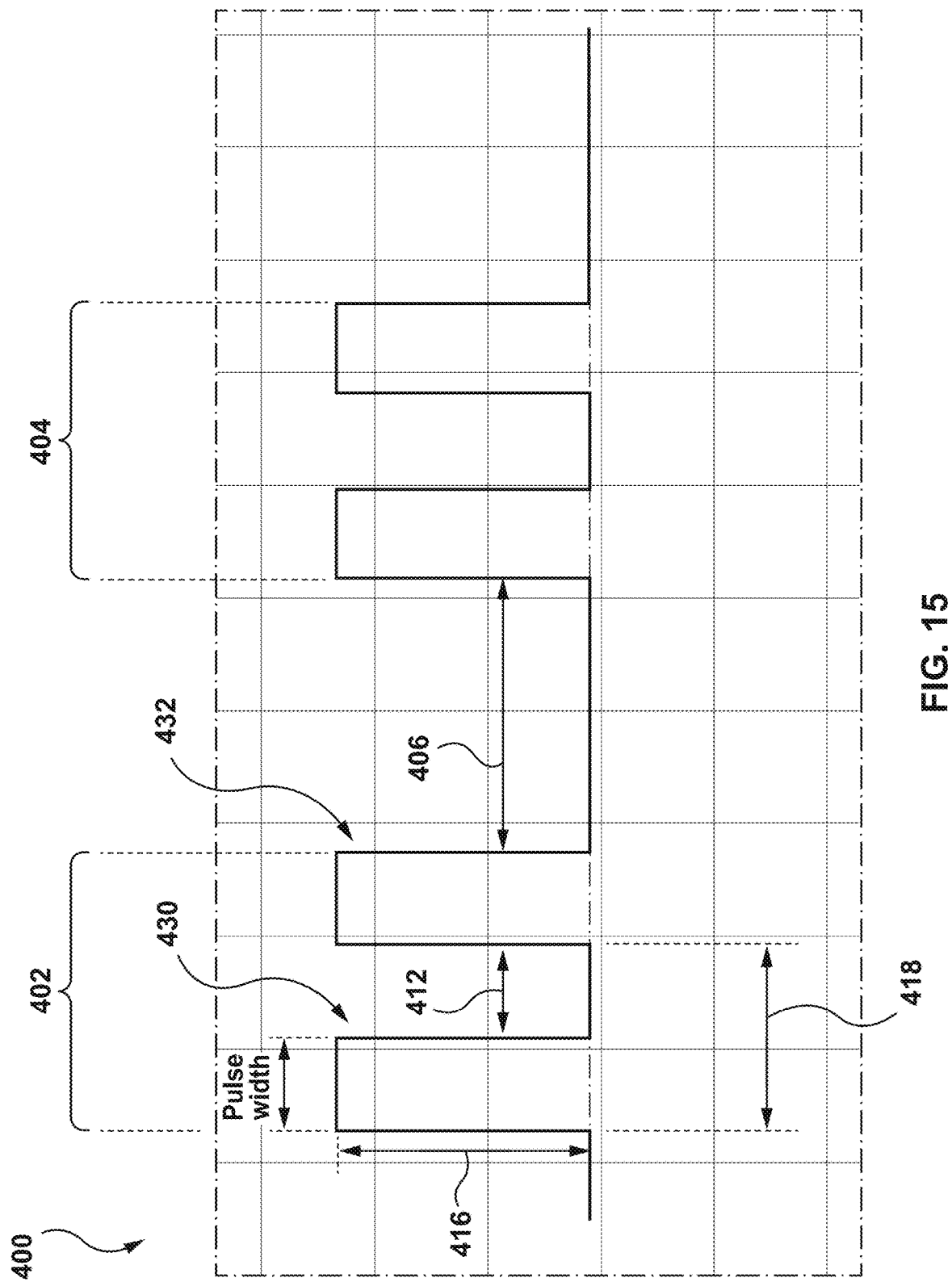
FIG. 15 illustrates an example waveform of another energy delivery algorithm.

FIG. 15 illustrates an example waveform 400 prescribed by another energy delivery algorithm 152. Again, two packets are shown, a first packet 402 and a second packet 404, wherein the packets 402, 404 are separated by a rest period 406. In this embodiment, each packet 402, 404 is comprised of a first monophasic pulse 430 and a second monophasic pulse 432. The first and second monophasic pulses 430, 432 are separated by dead time 412 between each pulse. This monophasic waveform could lead to a more desirable treatment effect as the same charge cell membrane potential is maintain for longer durations. However, adjacent muscle groups will be more stimulated by the monophasic waveform, compared to a biphasic waveform.

Figure 16:
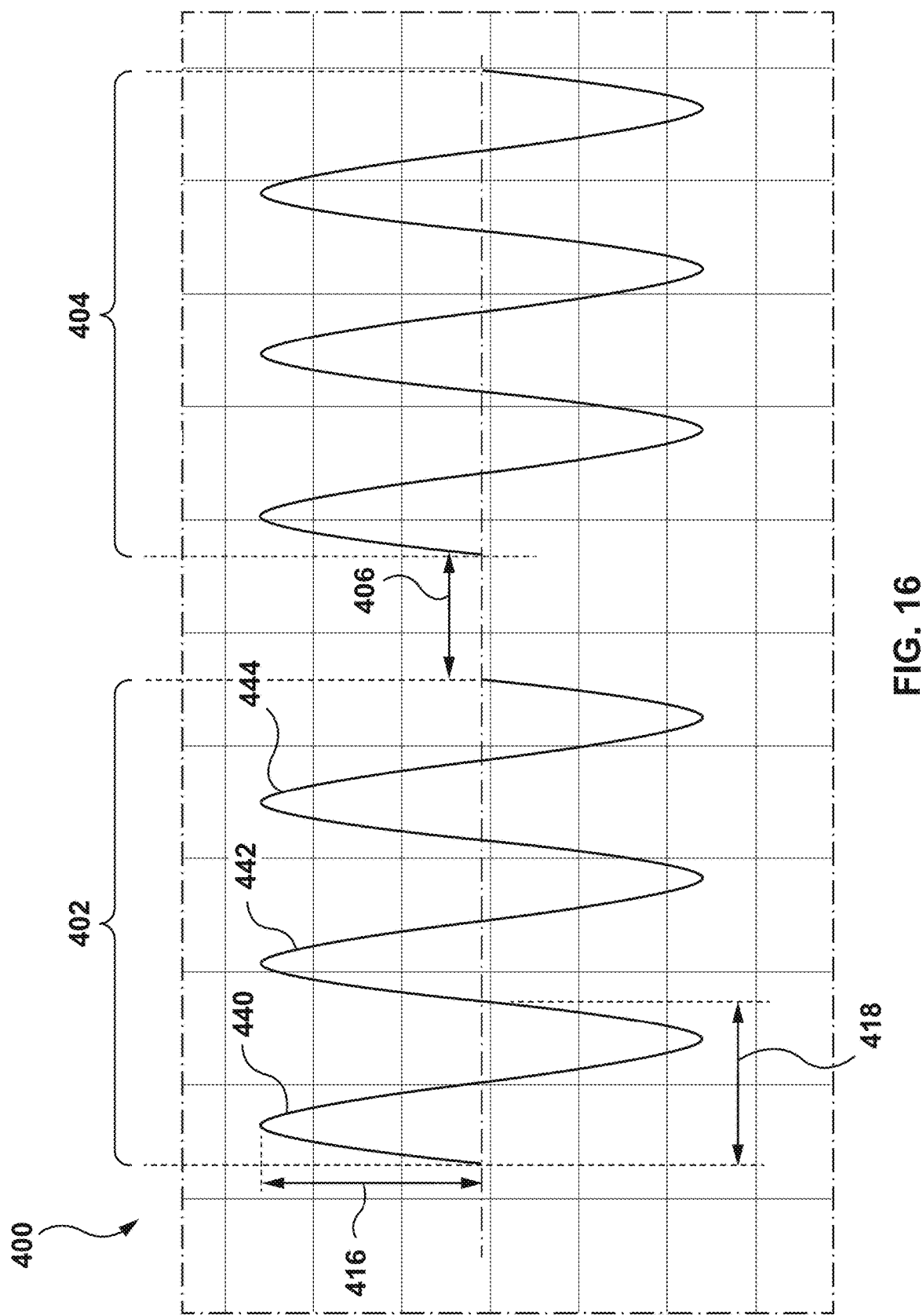
FIG. 16 illustrates an example waveform of another energy delivery algorithm.

FIG. 16 illustrates an example waveform 400 prescribed by another energy delivery algorithm 152. Again, two packets are shown, a first packet 402 and a second packet 404, wherein the packets 402, 404 are separated by a rest period 406. In this embodiment, each packet 402, 404 is comprised three biphasic pulses 440, 442, 444. And, rather than square waves, these pulses 440, 442, 444 are sinusoidal in shape. One benefit of a sinusoidal shape is that it is symmetrical. Symmetry may assist in reducing undesired muscle stimulation.

Energy delivery may be actuated by a variety of mechanisms, such as with the use of a button 164 on the catheter 102 or a foot switch 168 operatively connected to the generator 104. Such actuation typically provides a single energy dose. The energy dose is defined by the number of packets delivered and the voltage of the packets. Each energy dose delivered to the airway wall W maintains the temperature at or in the wall W below a threshold for thermal ablation, particularly thermal ablation of the basement membrane BM. In addition, the doses may be titrated or moderated over time so as to further reduce or eliminate thermal build up during the treatment procedure. Instead of inducing thermal effects, the energy dose provides energy at a level which induces biological mechanisms and cellular effects ultimately leading to the regeneration of healthy tissue.

III. BIOLOGICAL MECHANISMS & CELLULAR EFFECTS

As mentioned previously, the algorithm provides energy to the airway walls W at a level which induces biological mechanisms and cellular effects while reducing or avoiding inflammation. Example biological mechanisms and cellular process are described herein, but are not so limited.

The energy provided to the airway walls W may cause a variety of cellular effects which ultimately lead to the regeneration of healthy lung airway tissue. Example cellular effects include removal of particular cell types, such as by detachment of the cells from the airway wall W (so that the detached cells can be carried away by natural or induced methods) or by cell death (e.g. lysis and apoptosis). Other cellular effects include modification of particular cell types without removal, such as reprogramming the cells or conditioning the cells for improved agent uptake.

Figure 17:
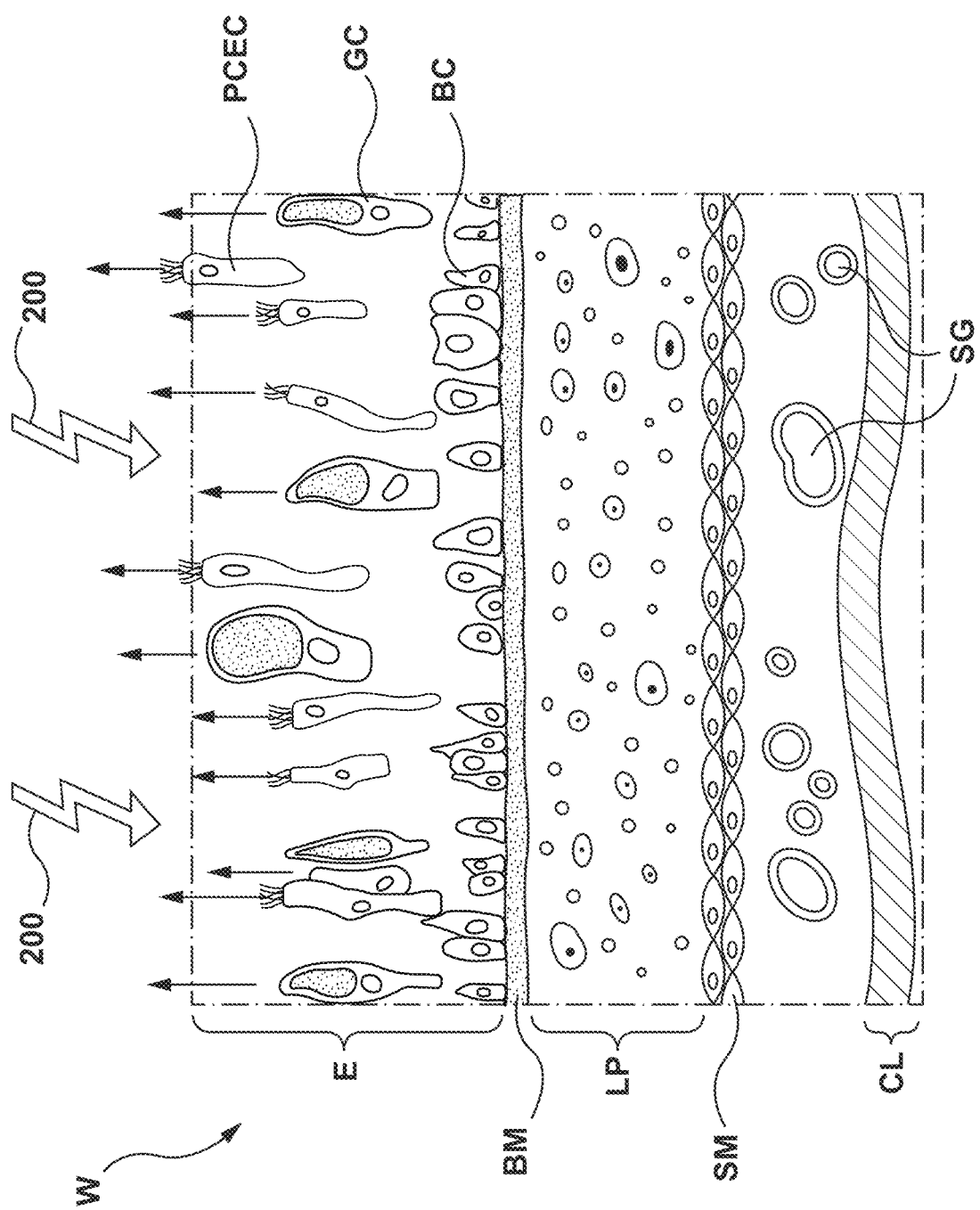
FIG. 17 illustrates an embodiment wherein delivered energy causes cells to be removed by detachment of the cells from the airway wall.

In some embodiments, particular cells are removed by detachment of the cells from the airway wall W. FIG. 17 illustrates an embodiment wherein energy (indicated by arrows 200) is provided to the airway wall W by the one or more energy delivery bodies. In this embodiment, the energy 200 has a targeted cell depth set to affect the epithelial layer E without extending beyond the basement membrane BM. The energy 200 is configured to cause particular epithelial cells, in this instance ciliated pseudostratified columnar epithelial cells PCEC and goblet cells GC, to detach from the remaining epithelial layer (e.g. basal cells BC) and/or the basement membrane BM. The detached cells are then free within the lung passageway, able to be removed by the natural process of expulsion or by interventional methods such as suction.

Figure 18:
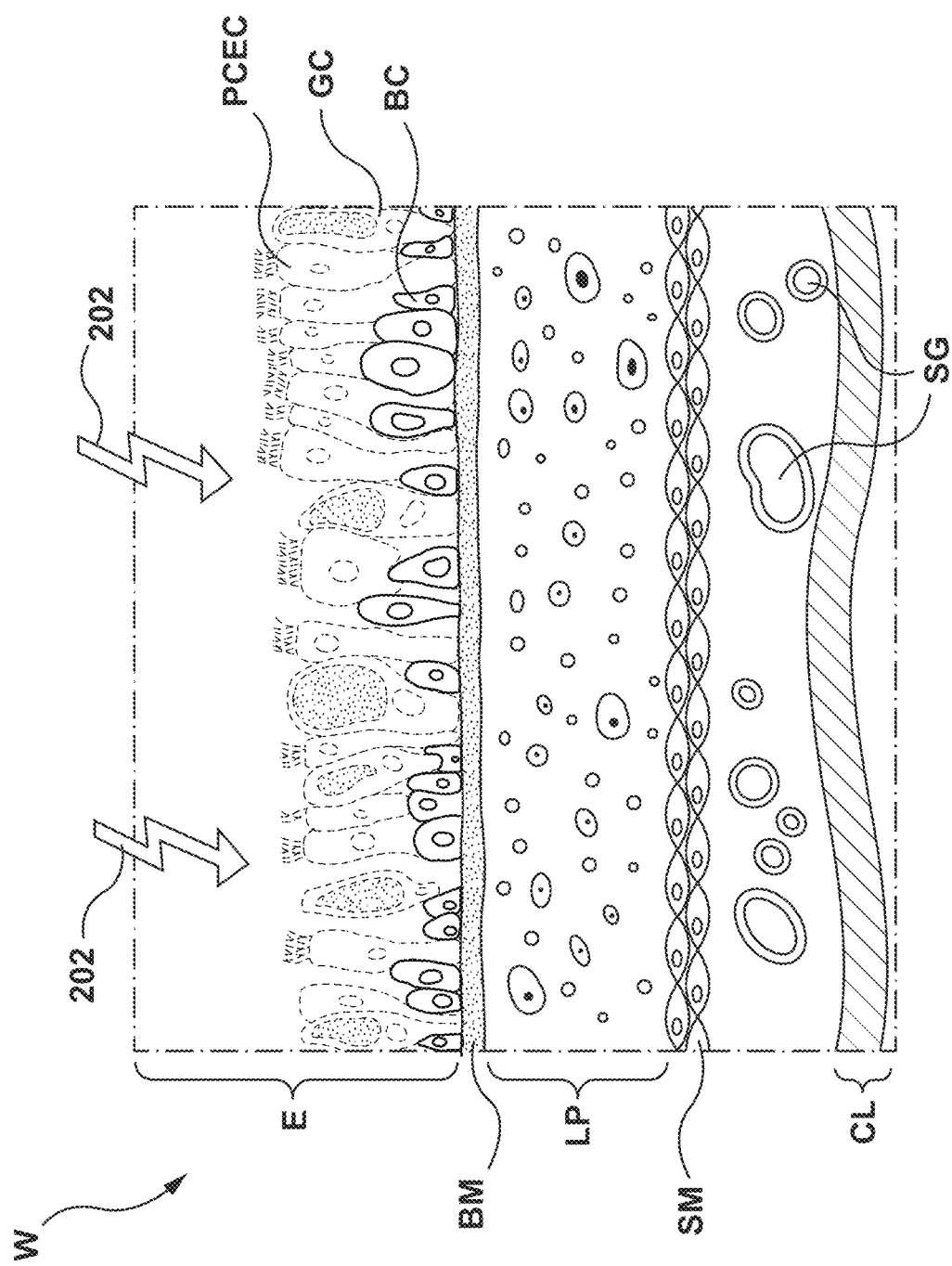
FIG. 18 illustrates an embodiment wherein delivered energy causes cells die, ultimately removing the cells from the airway wall.

In other embodiments, particular cells are removed by cell death, wherein the affected cells die by lysis or apoptosis, ultimately removing the cells from the airway wall W. FIG. 18 illustrates an embodiment wherein energy 202 is provided to the airway wall W by one or more energy delivery bodies and again, the energy 202 has a targeted cell depth set to affect the epithelial layer E without extending beyond the basement membrane BM. However, in this embodiment, the energy 202 is configured to cause particular epithelial cells, in this instance ciliated pseudostratified columnar epithelial cells PCEC and goblet cells GC, to die (as indicated by dashed line) while other cells (e.g. basal cells BC) remain. Cell death can be achieved by a variety of mechanisms. For example, in some embodiments, cell death occurs by destruction of the cell membrane. In such embodiments, the delivered energy may destroy the lipid bi-layer of the cell membrane such that the cell membrane is unable to maintain the barrier function of the cell. Without a plasma membrane, the cell cannot maintain proper intracellular concentrations of sodium, potassium, calcium and adenosine triphosphate (ATP). Consequently, the cell loses homeostasis and dies. In some embodiments, cell death occurs by disruption of intracellular organelles. In such embodiments, the delivered energy may permanently impede intracellular organelles from functioning. These organelles include endoplasmic reticulum, golgi apparatus, mitochondria, nucleus, nucleolus or others. Without the normal function of these intracellular organelles, the cell dies. It may be appreciated that in some instances, both the cell membrane and intracellular organelles are targeted by the delivered energy. Thus, if the delivered energy has only a partial effect on the cell membrane or intracellular organelles, the cumulative effect on both targets will ultimately yield cell death.

After cell death, the inflammatory cascade ensues. Cell fragments and intracellular contents signal leukocytes and macrophages to enter the affected area of the airway wall W. Over the course of hours to days, the dead cells are cleared from the area via phagocytosis. Unlike thermal ablation which damages the extracellular matrix, phagocytosis is limited to the cellular remains and not the collagen or matrix components of the extracellular matrix.

In some embodiments, particular cells are not removed, rather the targeted cells are modified or affected, such as reprogrammed. For example, in some embodiments, the ability of the goblet cells GC to secrete stored mucus or produce mucus at all is altered. Or, modification causes the cilia C on ciliated pseudostratified columnar epithelial cells PCEC to regain their function and better expel mucus up the airway. In other embodiments, ciliated pseudostratified columnar epithelial cells PCEC and goblet cells GC are unchanged but deeper structures are primarily affected such as a reduction in smooth muscle hypertrophy or neutralization of chronic inflammatory cells and eosinophils.

Whether the cells are removed or modified, the airway wall W regenerates and restores normal function. It may be appreciated that in some instances the epithelial cells may regenerate to their pre-treated state but the deeper cells, including the smooth muscle SM, eosinophils, submucosal glands SG, and chronic inflammatory cells, may be permanently reduced.

As mentioned previously, the algorithms may be tailored to affect tissue to a pre-determined depth and/or to target specific types of cells within the airway wall. For instance, various algorithms may specifically target the mucus layer M, the epithelial layer E, the basement membrane BM, the lamina propria LP, the smooth muscle cells SM, the submucosa, submucosal glands SG, nerves N, or various combinations of these. In one embodiment, the algorithm is configured to generate energy that penetrates the epithelial layer E of the airway wall W up to the basement membrane BM. Within this embodiment, a variety of different cell types may be targeted. For example, the energy may be configured to target the ciliated pseudostratified columnar epithelial cells PCEC and goblet cells GC causing their removal while leaving the basal cells BC behind. In such embodiments, the airway wall W may have abnormal and non-functioning ciliated pseudostratified columnar epithelial cells PCEC and hyperplastic, abnormal goblet cells GC causing mucus hypersecretion. The delivered energy causes the abnormal ciliated pseudostratified columnar epithelial cells PCEC and goblet cells GC to be removed, such as by cell death or detachment, leaving the basal cells BC intact along the basement membrane BM. Recall, the ciliated pseudostratified columnar epithelial cells PCEC and goblet cells GC are connected to each other by tight junctions TJ and adherens junctions AJ. In addition, the ciliated pseudostratified columnar epithelial cells PCEC and goblet cells GC are connected to the basal cells BC by desmosomes D. In some embodiments, the energy is configured so as to overcome the tight junctions TJ and adherens junctions AJ, and additionally the desmosomes D, allowing removal of ciliated pseudostratified columnar epithelial cells PCEC and goblet cells GC. Likewise, the energy may be configured to allow preservation of the hemidesmosomes H which connect the basal cells BC to the basement membrane 126. Thus, the basal cells BC remain intact.

Removal of ciliated pseudostratified columnar epithelial cells PCEC and goblet cells GC can reduce mucus production and mucus secretion by a variety of mechanisms. For example, such removal can mute the signaling mechanisms that lead to the expression of proteins found in mucin, thereby reducing mucus production. In particular, Muc5ac is a protein found in the mucin in the airway goblet cells GC that is encoded by the MUC5AC gene. There are several ligands and transcription factors that are involved in Muc5ac expression. Interleukin-13 binds to a receptor that includes the interleukin-4Rα subunit, activating Janus kinase 1 (Jak1), leading to the phosphorylation of Stat6. There is no consensus Stat6 binding site in the MUC5AC and Muc5ac promoter, but Stat6 activation leads to increased expression of SPDEF (SAM pointed domain-containing Ets transcription factor), which up-regulates multiple genes involved in mucous metaplasia, and inhibits expression of Foxa2, which negatively regulates Muc5ac. Several ligands bind ErbB receptors, including epidermal growth factor, transforming growth factor α, amphiregulin, and neuregulin, activating mitogen-activated protein kinases (MAPK). Hypoxia-inducible factor 1 (HIF-1) also can be activated downstream of ErbB receptors, and there is a conserved HIF-1 binding site in the proximal MUC5AC and Muc5ac promoter. Complement C3 and β2-adrenergic-receptor signaling, also amplify Muc5ac production, whereas transcription factors such as Sox2, Notch, E2f4, and Math primarily regulate development.

In the case of removal of ciliated pseudostratified columnar epithelial cells PCEC and goblet cells GC, by cell death or detachment, the signaling mechanisms that lead to Muc5ac expression are muted. Therefore, mucus is not produced, resulting in a decrease in mucus in the airway. This leads to benefits in patients with COPD (chronic bronchitis, emphysema), asthma, interstitial pulmonary fibrosis, cystic fibrosis, bronchiectasis, acute bronchitis and other pulmonary diseases or disorders.

Removal of such epithelial cells can also reduce mucus secretion by a variety of mechanisms. In particular, removal of the mucus producing goblet cells GC leaves no cells to secrete mucus into the airway. Secretion of mucus is induced by the molecular mechanism of mucin exocytosis. A mucin-containing secretory granule is docked to the plasma membrane by the interaction of a granule-bound Rab protein with an effector protein that acts as a tether to Munc18, which binds the closed conformation of Syntaxin anchored to the plasma membrane. Secretion is triggered when ATP binds to P2Y2 purinergic receptors (P2Y2R) coupled to Gq, activating phospholipase C (PLC), which generates the second messengers diacylglycerol (DAG) and inositol triphosphate (IP3). DAG activates Munc1314 to open Syntaxin so it can form a four-helix SNARE (soluble N-ethylmaleimide-sensitive factor attachment protein receptor) complex with SNAP-23 (synaptosomal-associated protein 23) and VAMP (vesicle-associated membrane protein), drawing together the granule and plasma membranes. IP3 induces the release of calcium from IP3 receptors (IP3R) in the endoplasmic reticulum (ER), activating Synaptotagmin to induce final coiling of the SNARE complex, which results in fusion of the membranes and release of the mucins.

With the removal of these epithelial cells, the signaling mechanisms that lead to mucin exocytosis are muted. Therefore, less mucus is secreted, resulting in a decrease in mucus in the airway. This leads to benefits in patients with COPD (chronic bronchitis, emphysema), asthma, interstitial pulmonary fibrosis, cystic fibrosis, bronchiectasis, acute bronchitis and other pulmonary diseases or disorders.

In some embodiments, the basal cells BC left on the basement membrane BM are able to regenerate normal goblet cells GC and normal ciliated pseudostratified columnar epithelial cells PCEC, thereby inducing reverse remodeling of the disease to reduce the mucus hypersecretion. In some embodiments, ciliated pseudostratified columnar epithelial cells PCEC additionally repopulate by migration from surrounding areas of the airway wall W to assist in regeneration of healthy tissue in the target area. The goblet cells GC typically regenerate at a lower level as compared to mild, moderate, or severe goblet cell hyperplasia that is present before the application of energy. The newly regenerated goblet cells GC are significantly less productive of mucus and the newly regenerated ciliated pseudostratified columnar epithelial cells PCEC regrow normally functioning cilia C, which more easily expel mucus M. Thus, healthy new target tissue can be regenerated within days of the procedure. This dramatically reduces symptoms of cough and mucus hypersecretion in patients which results in fewer and less severe exacerbations and improvement in quality of life.

It may be appreciated that in other embodiments, the energy may be configured to target the abnormal goblet cells CG causing their removal, such as by cell death or detachment, leaving behind the ciliated pseudostratified columnar epithelial cells PCEC and the basal cells BC. Removal of the abnormal goblet cells CG can reduce mucus production and/or mucus secretion by many of the mechanisms described above. Likewise, the energy may be configured to target the abnormal ciliated pseudostratified columnar epithelial cells PCEC causing their removal, such as by cell death or detachment, leaving behind the goblet cells CG and the basal cells BC. Likewise, the energy may be configured to target the abnormal basal cells BC causing their removal, such as by cell death or detachment, leaving behind the ciliated pseudostratified columnar epithelial cells PCEC and goblet cells GC. In any of these combinations of cell removal, it may be appreciated that the remaining cells may be additionally modified or affected by the delivered energy or by energy delivered subsequently. For example, abnormal goblet cells CG left behind may be modified so as to reduce mucus production and/or mucus secretion while remaining intact. It may also be appreciated that cell populations may be partially removed wherein some cells of a particular cell type are removed by the delivered energy while some remain, optionally modified.

In other embodiments, the algorithm is configured to generate energy that penetrates the epithelial layer E of the airway wall W up to and including the basement membrane BM. In such embodiments, changes to the epithelial layer E may occur as described above. Additionally, the basement membrane BM may be affected by the delivered energy so as to assist in remodeling the airway wall W to a healthy state. In some embodiments, the basement membrane BM is altered so as to stabilize or reduce the thickness of the basement membrane BM. Basement membrane BM thickening is a feature of many pulmonary diseases, including chronic bronchitis and asthma. Thus, the delivered energy may target the basement membrane BM so as halt or reverse such thickening. In some embodiments, such altering of the basement membrane BM affects the ability of cells, such as neutrophils, and inflammatory molecules, such as cytokines, to cross the basement membrane BM, thus assisting in regeneration of a healthy airway wall W.

In some embodiments, the algorithm is configured to generate energy that penetrates the epithelial layer E of the airway wall W and beyond the basement membrane BM. The position of various layers of the airway wall W beyond the basement membrane BM may vary due to variations in the anatomy along the lung passageways. For example, the position of the smooth muscle layer SM may vary along the length of the lung passageway, ranging from adjacent to the basement membrane BM to below the lamina propria LP. Thus, energy delivery may be titrated to target select layers of the airway wall W for a particular lung passageway segment. For example, the algorithm may be chosen or adjusted to affect the smooth muscle layer SM at its particular location. Smooth muscle hypertrophy is a feature of many pulmonary diseases, including chronic bronchitis, asthma and several other airway diseases resulting in airway hyperreactivity. In some embodiments, the delivered energy induces cell death of smooth muscle cells. This may reduce airway hyperreactivity and cause desired bronchodilation.

In some embodiments, the algorithm is chosen or adjusted to affect the submucosal glands SG. Submucosal glands overproduce and hypersecrete mucus in diseased airways. In some embodiments, the delivered energy induces cell death of submucosal glands SG. A reduction in submucosal glands SG may lead to less mucus in the airways and improvement in patient outcomes.

In some embodiments, the algorithm is chosen or adjusted so that the delivered energy affects the lamina propria LP. The lamina propria LP is comprised of loose connective tissue. The connective tissue and matrix architecture of the lamina propria LP is very compressible and elastic which allows expansion of the lung passageways. In addition, the loose structure allows for the presence of many cell types. The cell population of the lamina propria LP is variable and can include, for example, fibroblasts, lymphocytes, plasma cells, macrophages, eosinophilic leukocytes, and mast cells. Patients with airway disease often have chronic inflammation, specifically increased populations of lymphocytes and macrophages. In some embodiments, the delivered energy reduces the quantity of inflammatory cells, particularly lymphocytes, macrophages and/or eosinophils, thus reducing inflammation. Such energy removes, such as by cell death, cells from the lamina propria LP while maintaining the extracellular matrix. By maintaining the matrix architecture, stem cells and/or other cells are able to repopulate the matrix forming a healthy tissue. This is in contrast to fibrosis or other scar forming mechanisms wherein the layers of the airway wall W, including the extracellular matrix, are permanently changed, such as by melting or collapsing the layers together. In addition, the cartilage layer CL is not injured so as to maintain the structural integrity of the airway and prevent collapse.

Thus, it may be appreciated that one or more algorithms may be used to provide energy to affect one or more layers of the airway wall W. The energy may penetrate to a particular depth within the airway wall W, affecting numerous layers extending from the surface of the wall W to the particular depth. Or, the energy may be configured to affect cells at a particular depth without affecting surrounding layers. The affects may include cell removal, such as by cell death or detachment, or modification of the cell, such as to change particular functioning of the cell. In some instances, only a portion of cells of the same type or in the same layer may be affected by the delivered energy. Optionally, additional energy, either utilizing the same or different algorithm, may be delivered to affect a larger portion or all of the cells of the same type or in the same layer. Or, additional energy, either utilizing the same or different algorithm, may be delivered to increase the affect. For example, additional energy may result in cell removal of previously modified cells. Still further, additional energy, either utilizing the same or different algorithm, may be delivered to affect a different portion or depth of the airway wall.

The actual mechanisms by which the cells are removed or modified may vary depending on the algorithm 152, energy delivery bodies 108, and patient anatomy, to name a few. In some embodiments, cells are removed (e.g. detached) by dielectrophoresis.

Dielectrophoresis describes the movement of particles under the influence of applied electric fields which are non-uniform. The dielectrophoretic motion is determined by the magnitude and polarity of the charges induced in a particle by the applied field. The dipole moment induced in a particle can be represented by the generation of equal and opposite charges at the particle boundary. Since this induced charge is not uniformly distributed over the particle surface, it creates a macroscopic dipole. Since the applied field is non-uniform, the local electric field and resulting force on each side of the particle will be different. Thus, depending on the relative polarizability of the particle with respect to the surrounding medium, it will be induced to move either towards the inner electrode and the high-electric-field region (positive dielectrophoresis) or towards the outer electrode, where the field is weaker (negative dielectrophoresis). The dielectrophoretic force is a function of cell volume and polarization, the conductivity and permittivity of the surrounding media, and the frequency and spatial gradients of the magnitude of the generated electric field.

In some embodiments, removal of the abnormal epithelial cells, such as ciliated pseudostratified columnar epithelial cells PCEC and goblet cells GC, is the result of dielectrophoresis induced by one or more energy pulses delivered by the energy delivery body 108. In particular, in some embodiments, the epithelial layer E is separated by the action of dielectrophoresis, wherein the abnormal ciliated pseudostratified columnar epithelial cells PCEC and goblet cells GC are pulled away from the anchored basal cells BC and removed from the airway wall W. Recall, the basal cells BC are connected to the basement membrane BM by hemidesmosomes H whereas the basal cells BC connect to the goblet cells GC and ciliated epithelial cells EC via desmosomes D. The energy parameters and electrode configuration can be designed such that the desmosomes connections D separate but the hemidesmosomes H remain intact, thereby removing the surface cells, leaving the basal cells BC substantially intact, and ready to regenerate epithelium.

Figure 19:
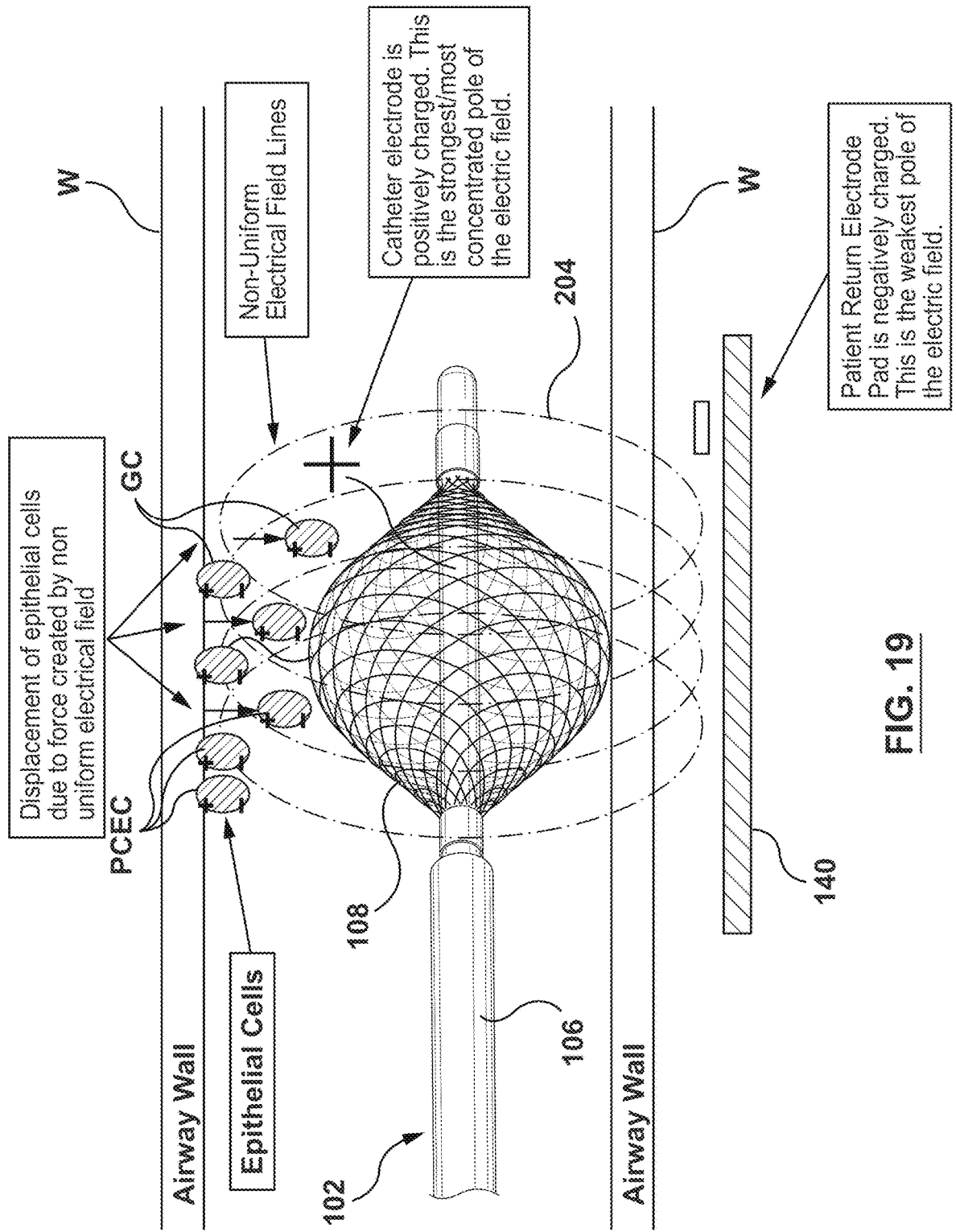
FIG. 19 schematically illustrates removal of epithelial cells by a dielectrophoresis effect.

FIG. 19 schematically illustrates removal of epithelial cells by a dielectrophoresis effect. Here, a distal portion of an embodiment of a catheter 102 having an energy delivery body 108 is illustrated positioned within a lung passageway. Energy 204 is delivered from the energy delivery body 108, as indicated by dashed electric field lines. The electric field is non-uniform due to the shape of the energy delivery body 108 and the placement of the return electrode 140 which is applied externally to the skin of the patient P. In this embodiment, the energy delivery body 108 is positively charged. This is the strongest/most concentrated pole of the electric field. The return electrode 140 is negatively charged and is the weakest pole of the electric field. Consequently, the non-uniform electric field causes detachment and displacement of the epithelial cells (e.g. ciliated pseudostratified columnar epithelial cells PCEC and goblet cells GC) from the airway walls W (as indicated by downward arrows). The epithelial cells are then removed by natural or induced mechanisms.

It may be appreciated that in some embodiments, the cells are removed or modified by other mechanisms, such as electroporation. Reversible electroporation is a non-thermal technique in which short, high voltage pulses generate intense electric fields that increase cell membrane voltage, leading to the creation of pores in cell membranes (e.g., plasma membrane). These pores allow chemicals, DNA, and/or other agents to be introduced into the cell. Thus, in some embodiments, reversible electroporation may be used, such as to modify cells in the airway wall W, such as to increase uptake of drugs or agents. Irreversible electroporation (IRE) is a non-thermal ablation technique in which short, high voltage pulses generate intense electric fields that increase cell membrane voltage, leading to the creation of pores in cell membranes (e.g., plasma membrane), inducing necrosis of cells. without substantial protein denaturation. Thus, in some embodiments, irreversible electroporation may be used, such as to remove cells by cell death. It may also be appreciated that in some embodiments, cells are removed or modified by a combination of mechanisms, such as a combination of dielectrophoresis and electroporation.

Alternatively or in addition to affecting tissue cells within the airway wall W, the delivered energy may affect pathogens resident in or near the airway wall W. Example pathogen types include without limitation bacteria (e.g., *Haemophilus influenzae*, *Streptococcus pneumoniae*, *Moraxella catarrhalis*, *Staphylococcus aureus*, *Pseudomonas aeruginosa*, *Burkholderia cepacia*, opportunistic gram-negatives, *Mycoplasma pneumoniae*, and *Chlamydia pneumoniae*), viruses (rhinoviruses, influenze/parainfluenza viruses, respiratory syncytial virus, coronaviruses, herpes simplex virus, adenoviruses), and other organisms (e.g., fungi).

In some embodiments, the pulmonary tissue modification system 100 may additionally or alternatively be useful for impacting pathogens found within a lumen of an airway (e.g. within the mucus layer M) or within tissue layers of the airway wall W of a patient such that infection is controlled, reduced, and/or eliminated. In some embodiments, the energy output from system 100 affects the mucus layer M and any pathogens that may be resident in or near the airway. The mucus layer M may become less viscous, thus making it easier for the patient to expel via coughing. The pathogens may be killed or programmed to die (e.g., apoptosis), thereby reducing or eliminating infection.

In some embodiments, the system 100 may assist the patient in developing antibodies or other commensal and supportive immune responses to targeted pathogens, improving future immunity and resistance to that pathogen in the future. Since the system 100 affects pathogens in a substantially non-thermal manner, leading to cell death, the cellular fragments still contain proteins. As these more intact proteins are released into the local environment and the circulation, the immune system develops new methods of surveillance, recognition and threat responses to these challenges, which can enhance host defense from those challenges or pathogens in the future.

As mentioned previously, it may be appreciated that the energy signal parameters may be manipulated to cause differing effects, such as differing depths of penetration. In some instances, the system 100 can be configured such that only the mucus layer M and any resident pathogens are affected. In some instances, the separation of the epithelial layer E occurs. In some instances, the system 100 can be configured such that the epithelial layer E separation occurs, pathogens are affected, and/or deeper structures are affected via a single energy delivery algorithm. In some instances, the generator can have a variety of energy delivery algorithms stored within it, and the user can apply two or more of these algorithms to tailor therapy to an individual patient. This may be done in a single therapy session or multiple therapy sessions in order to address the needs of individual patients.

In some instances, it can be desirable to affect deeper cells including smooth muscle cells SM submucosal glands SG, and/or nerves N. A patient's pathology can be more complex than mucus hypersecretion caused by the epithelium E and therefore the procedural intent is to affect deeper structures. Airway smooth muscle cells SM are known to contribute to bronchial hyper-responsiveness, submucosal glands SG can contribute to severe mucus hypersecretion, and nerves N innervate both submucosal glands SG and airway smooth muscle SM. Alternatively, patients with mixed pathologies such as asthma and chronic obstructive pulmonary disease (COPD) (e.g. Asthma-COPD Overlap Syndrome) can benefit from a procedure that targets several mechanisms (e.g., mucus hypersecretion, smooth muscle hypertrophy, cilia dysfunction, and/or the like) and/or target tissues. The energy dose can be titrated (e.g., iteratively modified based on sensor and/or other feedback) to affect structures deep to the epithelium E. In some instances, as the energy dose is increased, the submucosal glands SG undergo a mild partial membrane lysis or a significant loss of structural integrity. Uniquely and unlike thermal energy, the lamina propria LP, which is a cell layer that sits between the epithelium E and submucosal glands SG, remains unchanged. A thermal energy source would cause significant changes in the structure of the extracellular matrix and cause fibrosis.

In addition to the submucosal glands SG, the smooth muscle SM can be affected depending on the dosing, ranging from focal changes to obliteration which causes removal of the epithelium E over days to weeks. The cartilage layer CL, the deepest structure in the airway wall, is unaffected by the energy and shows no signs of inflammation or necrosis, acting as an insulative barrier.

IV. SENSORS

In some embodiments, one or more sensors 160 are included in the system 100 to measure one or more system or tissue parameters. Example sensors 160 include temperature sensors, impedance sensors, resistance sensors, surface conductance sensors, membrane potential sensors, capacitance sensors, and/or force/pressure sensors, or combinations thereof. Thus, parameters measured by sensors 160 can include impedance, membrane potential or capacitance, and/or temperature, to name a few. Sensors 160 can be used for (a) obtaining a baseline measure, (b) measuring a parameter during the delivery of energy, and/or (c) measuring a parameter following energy delivery, among others.

Sensors 160 can be positioned on energy delivery bodies 108, adjacent to energy delivery bodies 108, or in any suitable location along the distal portion of the catheter 102. Temperature sensors can monitor the temperature of an electrode and/or the electrode/tissue interface. Impedance sensors can monitor the impedance of the tissue across any two electrodes. Conductance sensors can monitor the transmission of electrical energy across any two electrodes. Force/pressure sensors can monitor the amount of force or pressure that the electrodes are placing on the tissue.

This sensor information can be used as feedback to the system in order to, as non-limiting examples, determine proper deployment of energy delivery bodies 108, drive a therapeutic algorithm 152, and/or stop energy delivery for safety reasons. Sensors 160 can also be used to sense when an adequate treatment is achieved. An algorithm 152 within the generator 104 can also use the sensed data to automatically titrate the therapeutic algorithm 152 such that the target tissue treatment is achieved. Said another way, one or more parameters and/or aspects of the therapeutic algorithm can be modified based on the sensor data in an iterative manner. For example, in some embodiments, the power and/or energy duration can be increased or decreased based on the sensor data.

A. Impedance Sensors

1. Ensuring Proper Placement of Energy Delivery Bodies

In some embodiments, one or more impedance sensors are used to determine if the energy delivery bodies 108 are properly inserted and deployed in the airway of the lung. In some embodiments, a short duration, low voltage signal is delivered to the energy delivery bodies 108 during their placement and deployment/expansion within the targeted area of the airway. Based on measured electrical current feedback received by the generator 104 from the one or more impedance sensors, the generator's processor 154 performs a calculation using the set voltage and actual current to calculate the impedance. Calculated impedance is then compared to impedance values that are considered acceptable for the properly inserted and deployed energy delivery bodies 108. If the calculated impedance is outside of the range of acceptable impedances, the generator 104 displays a specific message and/or emits a specific sound alerting the operator. For example, if the energy delivery bodies 108 are still within the bronchoscope 112, the generator 104 may measure a very high impedance outside of the acceptable range. In such instances, the generator may then display a message (e.g., Check Electrode Position) until the operator repositions the energy delivery bodies 108 into the airway where the impedance is significantly lower and within the acceptable range. At this point, the message may change (e.g., Ready).

It may be appreciated that other types of sensors, such as temperature, force or pressure sensors may additionally or alternatively be used to verify electrode to tissue contact prior to initiation of treatment. It may also be appreciated that sufficient contact between electrodes and the walls of the airway is an important factor for effective treatment. Solid and consistent contact is desired to satisfactorily couple the energy from the electrode to the tissue and to achieve desired tissue effects.

2. Ensuring Proper Functioning of Catheter

In some embodiments, one or more impedance sensors are utilized to determine if the catheter 102 is functional or potentially defective. In such embodiments, a short duration, low voltage signal (e.g., a signal having a duration from 1-5 packets, and a voltage of about 500V) is delivered to the energy delivery bodies during their placement and deployment/expansion within the targeted area. Based on the measured electrical current feedback received by the generator 104, the generator's processor 154 performs a calculation using the set voltage and actual current to calculate the impedance. Calculated impedance is compared to the impedance values that are considered acceptable for a catheter that is functioning properly. If the calculated impedance is outside of the range of acceptable impedances, the generator 104 optionally displays a specific message and/or emits a specific sound alerting the operator. For example, if the catheter is defective, the impedance may be very high. In this embodiment, the generator 14 displays a message (e.g., 'Replace Catheter'). Once replaced, the generator 104 may then detect a much lower impedance within the acceptable range and display another message (e.g., 'Position Catheter'). Thus, impedance measurements can be used to avert a safety concern by detecting a malfunctioning catheter.

3. Modifying the Energy Algorithm

In some embodiments, impedance measurements can be made prior to or after applying energy in order to define which energy delivery algorithm 152 to apply and/or the need to apply additional energy to the target location. In some embodiments, pre-treatment impedance measurements can be used to determine the settings of various signal parameters. In other embodiments, sensors can be used to determine if the energy-delivery algorithm should be adjusted.

In some embodiments, the impedance measurement is performed as follows. A short duration, low voltage signal is delivered to the energy delivery body 108 via a generator (e.g., the generator 104) once positioned at a targeted area within a lung passageway. Based on the measured electrical current feedback received by the generator 104, the generator 104 performs a calculation using the set voltage and actual current to calculate the impedance. The calculated impedance is compared to impedance values that are considered acceptable for the measured impedance. Then, the energy delivery algorithm 152 is modified or tailored based upon the measured impedance. Parameters that can be adjusted include, but are not limited to, voltage, frequency, rest period, cycle count, dead time, packet count or number of packets, or a combination thereof. Thus, a feedback control loop can be configured to modify a parameter of energy delivery based on the measured one or more system or tissue parameters.

In some embodiments, one or more impedance sensors are used to monitor the electrical properties of the tissue. Impedance values can be regarded as an indicator of tissue state. In some embodiments, impedance is measured at different frequencies to provide an impedance spectrum. This spectrum characterizes the frequency dependent, or reactive, component of impedance. Tissue has both resistive and reactive components; these are components of complex impedance. Reactance is the frequency dependent component of impedance that includes tissue capacitance and inductance. Changes in the state of the tissue can result in changes to overall impedance as well as to changes in the resistive or reactive components of complex impedance. Measurement of complex impedance involves the conduction of a low voltage sensing signal between two electrodes. The signal can include but not be limited to a sine wave. Changes in complex impedance, including changes in resistance or reactance, can reflect the state of treated tissue and therefore be used as indicators that treatment is affecting tissue, not affecting tissue, and or that treatment can be complete. Impedance values can also change depending on the contact conditions between the sensors and airway tissue. In this way, sensors can also be used to determine the state of contact between electrodes and the tissue.

In some instances, the generator 104 instructs the user that additional energy delivery at the target location is not needed. Optionally, the generator 104 displays a specific message and/or emits a specific sound alerting the operator as to which energy delivery algorithm 154 has been selected, or that treatment is complete at that target location. Thus, the generator 104 can be configured to automatically select the appropriate algorithm for a particular measured impedance or shut off the delivery of energy signals if the treatment is determined to be completed. Further, impedance or other sensors can be used to determine that a treatment should be automatically stopped due to a safety concern.

B. Temperature Sensors

In some embodiments, one or more temperature sensors are used to measure electrode and/or tissue temperature during treatment to ensure that energy deposited in the tissue does not result in clinically significant tissue heating. In some embodiments, the temperature measured at or near the electrodes is also used to determine the state of contact between the electrode and tissue prior to treatment. This can be achieved by applying energy at a level sufficient to generate heat but insufficient to cause substantial thermal injury. The temperature may differ in its steady state value or in its variability depending upon whether the electrode is pressed against the airway wall, moving, or suspended in the airway lumen.

In some embodiments, one or more temperature sensors are disposed along the surface of one or more energy delivery bodies 108 so as to contact the tissue and ensure that the tissue is not being heated above a pre-defined safety threshold. Thus, the one or more temperature sensors can be used to monitor the temperature of the tissue during treatment. In one embodiment, temperature changes that meet pre-specified criterion, such as temperature increases above a threshold (e.g., 40° C., 45° C., 50° C., 60° C., 65° C.) value, can result in changes to energy delivery parameters (e.g. modifying the algorithm) in an effort to lower the measured temperature or reduce the temperature to below the pre-set threshold. Adjustments can include but not be limited to increasing the rest period or dead time, or decreasing the packet count. Such adjustments occur in a pre-defined step-wise approach, as a percentage of the parameter, or by other methods.

In other embodiments, one or more temperature sensors monitor the temperature of the tissue and/or electrode, and if a pre-defined threshold temperature is exceeded (e.g., 65° C.), the generator 104 alters the algorithm to automatically cease energy delivery. For example, if the safety threshold is set at 65° C. and the generator 104 receives the feedback from the one or more temperature sensors that the temperature safety threshold is being exceeded, the treatment can be stopped automatically.

C. Sensors to Monitor Electrode Contact

In some embodiments, multiple sensors (e.g. temperature, impedance, force, pressure etc.) are placed in various locations, such as circumferentially, on the surface of the one or more energy delivery bodies 108. In such configurations, the sensors may be used to indicate if the contact between the surface of the one or more energy delivery bodies 108 and the bronchial airway wall surface is sufficient, such as suitably circumferential and/or stable. If sensors indicate that the contact is not sufficient, such as not circumferential (e.g., non-uniform temperature, impedance, force etc.) and/or stable (e.g., continuously changing temperature, impedance, force, etc.), the operator may adjust the level of the expansion for the one or more energy delivery bodies or choose a catheter 102 with different sized energy delivery bodies 108 that better match the internal diameter of the bronchus/bronchi that are being treated. In some embodiments, the generator 104 is configured to interpret the degree, quality, and/or stability of contact and provide the operator feedback to aid in the proper positioning of energy delivery bodies. For example, as the operator is in the process of positioning the one or more energy delivery bodies which is not in circumferential contact, the user interface 150 on the generator 104 may display a message such as "Poor Contact".

In some embodiments, force or pressure sensors can be used to detect and measure the contact force between the energy delivery bodies and the walls of the airway and thereby determine the contact conditions between energy delivery bodies and tissue.

It may be appreciated that any of the system 100 embodiments disclosed herein can incorporate one or more sensors to monitor the application of the therapy.

V. CARDIAC SYNCHRONIZATION

Figure 20:
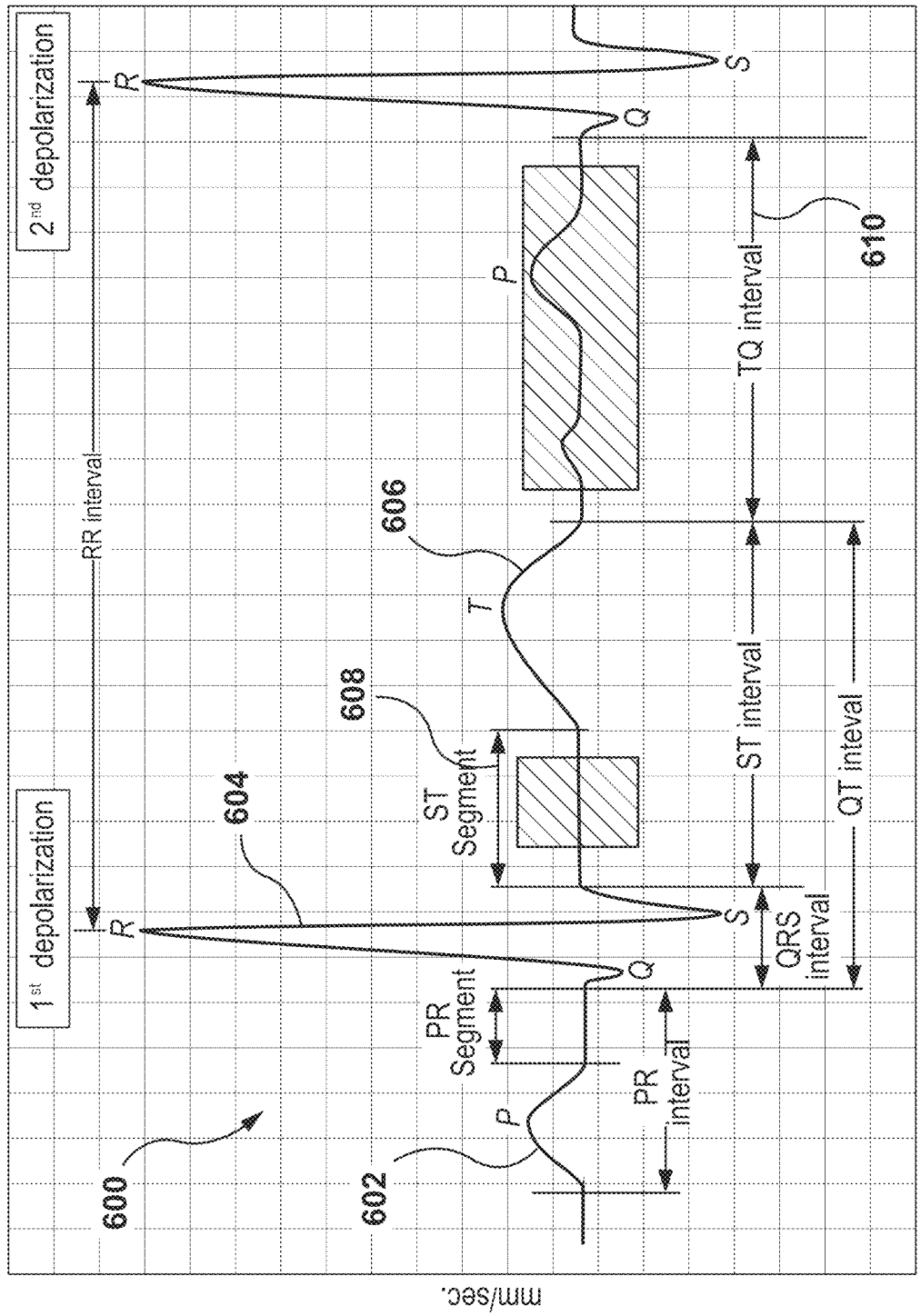
FIG. 20 is a graph illustrating portions of a sample electrocardiogram (ECG) trace of a human heart highlighting periods wherein it is desired to deliver energy pulses to the lung passageway via the energy delivery body.

In some embodiments, the energy signal is synchronized with the patient's cardiac cycle to prevent induction of cardiac arrhythmias. Thus, the patient's cardiac cycle is typically monitored with the use of an electrocardiogram (ECG). Referring to FIG. 20, a typical ECG trace 600 includes a repeating cycle of a P wave 602 representing atrial depolarization, a QRS complex 604 representing ventricular depolarization and atrial repolarization, and a T wave 606 representing ventricular repolarization. To safely deliver energy within the airway in close proximity to the heart, synchronization between energy delivery and the patient's cardiac cycle is employed to reduce the risk of cardiac arrhythmia. High voltage energy can trigger a premature action potential within the cardiac muscle as the delivered energy increases the cardiac muscle cell membrane permeability allowing ion transport, which can induce cardiac arrhythmias, especially ventricular fibrillation. To avoid cardiac arrhythmias, the electrical energy is delivered to the airway in a fashion that is outside the "vulnerable period" of the cardiac muscle. Within one cardiac cycle (heartbeat), the vulnerable period of the ventricular muscle is denoted on an ECG by the entire T wave 606. Typically, for ventricular myocardium, the vulnerable period coincides with the middle and terminal phases of the T wave 606. However, when high energy pulses are delivered in close proximity to the ventricle, the vulnerable period can occur several milliseconds earlier in the heartbeat. Therefore, the entire T wave can be considered to be within the vulnerable period of the ventricles.

The remaining parts of a cardiac cycle are the P wave 602 and the QRS complex 604, which both include periods when atrial or ventricular muscle is refractory to high voltage energy stimuli. If high voltage energy pulses are delivered during the muscle's refractory period, arrhythmogenic potential can be minimized. The ST segment 608 (interval between ventricular depolarization and repolarization) of the first cardiac cycle and the TQ interval 610 (interval including the end of the first cardiac cycle and the mid-point of the second cardiac cycle) are the periods where high voltage energy can be delivered without induction of cardiac arrhythmia due to the cardiac muscle depolarized state (refractory period). FIG. 20 includes shaded boxes that indicate example portions of the cardiac cycle during which energy can be applied safely.

Figure 21:
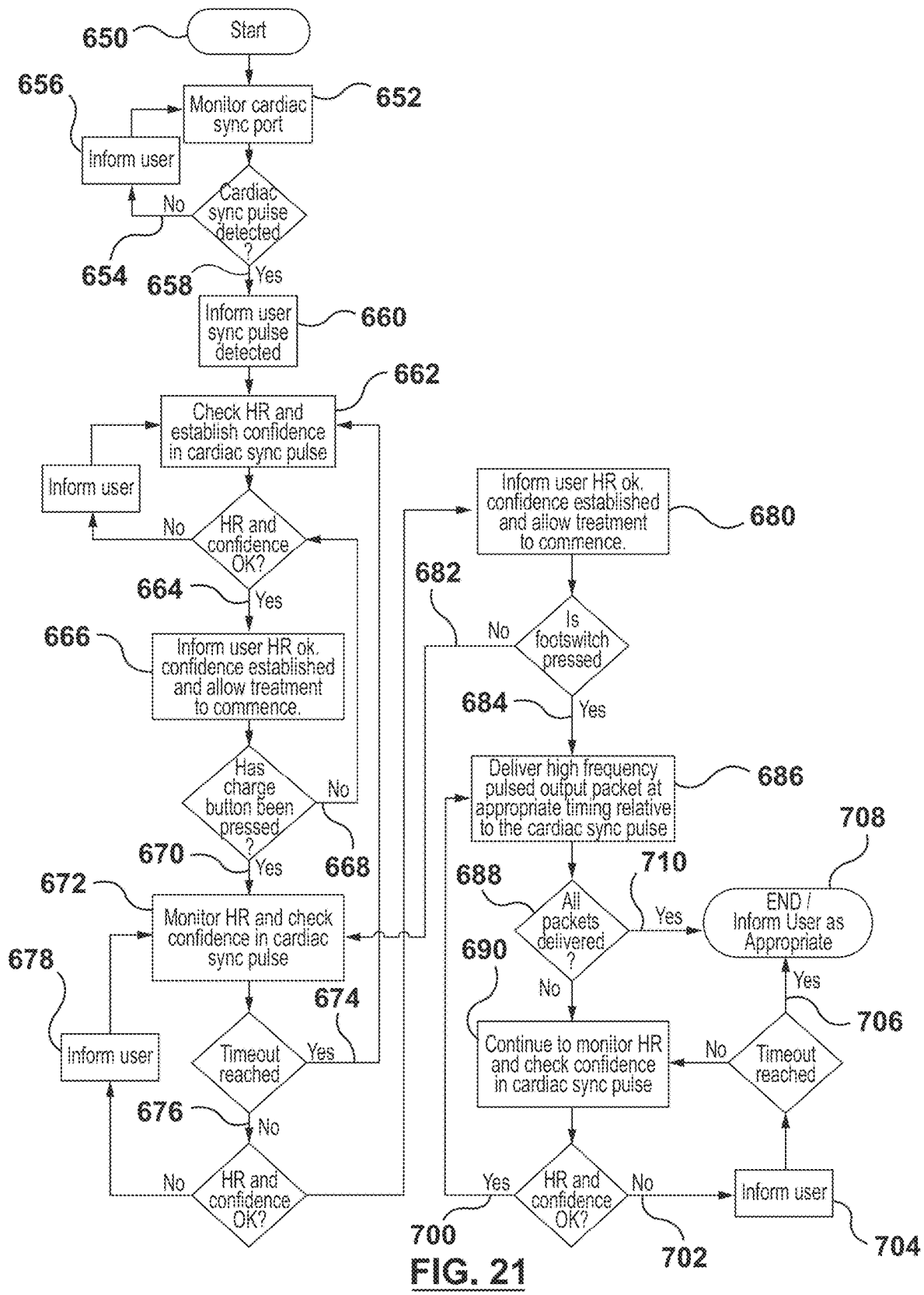
FIG. 21 is a flowchart depicting an embodiment of a method for synchronizing the delivery of energy with the cardiac cycle.

FIG. 21 is a flowchart depicting an embodiment of a method for synchronizing the delivery of energy with the cardiac cycle, according to some embodiments. In this embodiment, the electrocardiogram (ECG) is acquired by an external cardiac monitor 170 (such as the cardiac monitors available from AccuSync Medical Research Corporation) operatively connected to a communications port 167 on the energy producing generator 104, although it is understood that any suitable monitor may be employed. Here, the cardiac monitor 170 is used to continuously acquire the ECG, analyze one or more cardiac cycles, and identify the beginning of a time period where it is safe to apply energy. In some embodiments, when the cardiac monitor 170 detects this event/beginning (e.g., the R wave of an ECG trace), it sends a low voltage transistor to transistor logic (TTL) pulse (e.g., ≤5 V) to the communications port 167. At the start step 650, the processor 154 of the energy producing generator 104 monitors (at step 652) the communications port 167 to determine if the cardiac sync pulse is detected. If a TTL pulse is not detected (at step 654) by the generator 104, the user interface 150 is used to inform the user (at step 656). For example, the user interface 150 may display a solid red heart and/or any other suitable visual indicator. Once a cardiac sync pulse is detected (at step 658) by the generator 104, the user interface 150 is used to inform the user (at step 660). For example, the solid red heart may turn to a yellow blinking heart, turning on at the time the cardiac sync pulse is detected.

Because the external cardiac monitor 170 can send false TTL pulses and because the generator should not allow treatment to continue if the patient's heart rate is outside of the normal expected limits, is erratic, and/or has a widened QRS complex not associated with/different from the patient's baseline rhythm, the next step can involve checking the heart rate to establish confidence in the TTL pulse (i.e., cardiac sync pulse) (at step 662). In one embodiment, the processor 154 of the generator 104 is used to monitor the TTL pulses and calculate the time between each beat, referred to as $\Delta t1$, $\Delta t2$, $\Delta t3$, $\Delta t4$, $\Delta t5$. These values can be stored within the data storage module 156 of the generator 104 as a rolling buffer having the last five $\Delta t$ calculations. Next, the average of those five values can be calculated, referred to as $\Delta t$-ave. The next one or more TTL pulses detected can be used to calculate the next $\Delta t(s)$ (e.g., $\Delta t6$, $\Delta t7$, etc.), which can also be stored in the data storage module 156. For example, two TTL pulses can be utilized.

Next, the algorithms module 152 of the generator 104 is used to compare these values to a set of criteria that, if met, provide confidence that the patient's heart rhythm is normal/consistent and that the TTL pulse is reliable. For example, the heart rate can be calculated and checked to ensure it is between 40-150 beats per minute (bpm). In this example, $\Delta t6$ and $\Delta t7$ can also be compared to $\Delta t$-ave to verify that the heart rate is not erratic. In one embodiment, $\Delta t6$ and/or $\Delta t7$ can be within ±15% of $\Delta t$-ave in order to continue. In this example, both criteria must be met in order to confirm confidence (at step 664); however, in other embodiments, both criteria may not be required. Once confidence is confirmed, the user interface 150 can be used to inform the user that it is safe to continue (at step 666). For example, the yellow flashing heart on the user interface 150 can change to a green flashing heart. Next, the user interface 150 is used to direct the user to charge the high energy storage unit (e.g., one or more capacitors) of the generator 104. In one example, the user interface 150 displays a soft-key labeled 'Charge', which the user may press to charge the high energy storage unit. If the charge button has not been pressed (at step 668), the processor 154 continues to check heart rate and confidence in the TTL signals.

Once the processor 154 recognizes that the charge button has been pressed (at step 670), the processor 154 continues to check heart rate and confidence in the TTL signals (at step 672). During that time, if a predefined/predetermined amount of time has passed (e.g., about 30, 40, 50, 60, or up to 120 seconds, including all values and sub ranges in between) without verification that the heart rate and TTL confidence is established (at step 674), the system aborts the charging mode and reverts to the system status wherein it is checking heart rate and establishing confidence in the cardiac sync pulse (at step 662). If the timeout is not reached (step 676), the user interface 150 informs the user (at step 678) until confidence is established (at step 680). The user interface 150 can change such that the soft-key is now labeled 'Ready'. The system 100 is now waiting for the footswitch 168 to be pressed.

While the system 100 waits for the footswitch 168 to be pressed (at step 348), it continues to monitor heart rate and check for confidence (672). Another timeout can be predefined (e.g., about 30, 40, 50, 60, or up to 120 seconds, including all values and sub ranges in between), such that if the user does not press the footswitch 168 within that time (e.g., timeout is reached, as illustrated, at step 674), the system aborts being ready to deliver energy and returns to the system status wherein it is checking heart rate and establishing confidence in the TTL pulses (at step 662). Once the user presses the footswitch (at step 684), energy delivery can commence (at step 686). However, the generator 104 can be configured to wait until the next cardiac pulse is detected to further ensure that energy delivery occurs after the R-wave is detected. In one embodiment, the energy is not delivered until about 50 milliseconds after the leading edge of the TTL pulse is detected; however this value could range from about 0-300 milliseconds. The first energy packet can then be delivered (at step 686). The processor 104 then checks to determine if all packets have been delivered (at step 688). If not, the processor 154 continues to monitor heart rate and check confidence in the TTL pulses (at step 690) and energy delivery can continue once confidence in the cardiac sync pulse (at step 662) is re-established.

In some instances, it may be beneficial to ignore TTL pulses immediately following energy delivery, as they may be false triggers caused by the high voltage energy being delivered. For example, the processor 154 can ignore TTL pulses for about 400 ms after energy is delivered or about 450 ms after the leading edge of the last TTL pulse. In other situations, the TTL pulses can be ignored for about 50 ms- to about 1 second, including all values and sub ranges in between. Once the processor detects the next TTL pulse, the next $\Delta t$ can be calculated and compared against the criteria (at step 690) previously defined (i.e., based on a rolling average). Due to the potential for transient delays in the heart beat following energy delivery, if the next $\Delta t$ falls outside of the criteria, it is simply ignored. Then, the next $\Delta t$ can then be calculated and compared against the criteria previously defined. If the criteria are met (at step 700), the next packet is delivered (at step 686). If all packets have not been delivered, the system continues to monitor the heart rate and check for confidence in the cardiac sync pulse (at step 690) as previously described. If confidence is established (at step 700), the cycle continues. If confidence is not established (at step 702), the user is informed (at step 704), for example, by the heart turning yellow and flashing or turning solid red.

If the system 100 cannot determine acceptable confidence or no longer detects a TTL pulse within a certain amount of time (e.g., about 10, 20, 30, 40, 50, or 60 seconds), a timeout will be reached (at step 706), and the user interface 150 can be used to notify the user (at step 708). At this time, the cycle can end, and any remaining packets would not be delivered. The process then returns to start (at step 650). If the system can determine acceptable confidence (at step 700) within the set time limit, a timeout will not be reached (at step 688), and the cycle continues with continued monitoring of heart rate and checks for confidence (at step 690), as previously described. If confidence is gained (at step 700), the next energy packet is delivered (at step 686). Once all packets are delivered, the treatment is deemed complete (at step 710) and the user is informed of completion of treatment (at step 708). If the current associated with delivery of any of the high energy packets (at step 686) exceeds a set value (e.g., about 45 amps), the cycle can also end (at step 708).

It may be appreciated that in some embodiments, components for acquiring the electrocardiogram 170 are integrally formed with the generator 104. If the cardiac monitor is limited to acquiring up to a 5-lead ECG, and it may be beneficial to incorporate additional leads into the system. This would further eliminate the need to use the communications port 167 to receive cardiac sync pulses. Rather, the processor 154 can be configured to detect the R-waves directly and to assess the integrity of the entire QRS complex.

In some embodiments, the processor 154 may be configured to use either fewer or more than five $\Delta t$'s to calculate $\Delta t$-ave. In some embodiments, the processor 154 may be configured to use between three and ten $\Delta t$'s to calculate $\Delta t$-ave. Further, the processor 154 may be configured to use a $\Delta t$ other than $\Delta t6$ and $\Delta t7$ to confirm confidence. For example, the processor 154 may be configured to use any subsequent $\Delta t$. The processor 154 may also be configured to allow heart rates beyond the 40-150 bpm described above. For example, the processor 154 may be configured to allow heart rates in the range of 30-160 bpm, including all values and sub ranges in between. The processor 154 may also be configured to allow Δt6 or Δt7 to be more or less than ±10%. For example, the processor 154 may be configured to allow Δt6 or other data point, including rolling averages, to be within ±3% to ±50%. User interface 150 examples provided herein are merely examples, and should not be considered limiting.

Thus, it may be appreciated that generator can be configured to continuously monitor the patient's heart rate, and in case cardiac arrhythmias are induced, the treatment will be automatically stopped and an alarm can sound.

VI. IMAGING

Methods associated with imaging that can be useful include: (a) detecting diseased target tissue, (b) identifying areas to be treated, (c) assessing areas treated to determine how effective the energy delivery was, (d) assessing target areas to determine if areas were missed or insufficiently treated, (e) using pre- or intra-procedural imaging to measure a target treatment depth and using that depth to choose a specific energy delivery algorithm to achieve tissue effects to that depth, (f) using pre or intra-procedural imaging to identify a target cell type or cellular interface and using that location or depth to choose a specific energy delivery algorithm to achieve tissue effects to that target cell type or cellular interface, and/or (g) using pre-, intra-, or post-procedural imaging to identify the presence or absence of a pathogen with or without the presence of inflamed tissue.

In some embodiments, confocal laser endomicroscopy (CLE), optical coherence tomography (OCT), ultrasound, static or dynamic CT imaging, X-ray, magnetic resonance imaging (MRI), and/or other imaging modalities can be used, either as a separate apparatus/system, or incorporated/integrated (functionally and/or structurally) into the pulmonary tissue modification system 100 by either incorporating into the energy delivery catheter 102 or a separate device. The imaging modality (or modalities) can be used to locate and/or access various sections of tissue as demonstrated by a thick area of epithelium, goblet cell hyperplasia, submucosal glands, smooth muscle, and/or other aberrancies relative to where the system is deployed in the chest. In some embodiments, the targeted depth of treatment can be measured and used to select a treatment algorithm 152 sufficient to treat to the targeted depth. At least one energy delivery body can then be deployed at the site of abnormal airway wall tissue and energy delivered to affect the target tissue. The imaging modality (or modalities) can be used before, during, between, and/or after treatments to determine where treatments have or have not been delivered or whether the energy adequately affected the airway wall. If it is determined that an area was missed or that an area was not adequately affected, the energy delivery can be repeated followed by imaging modality (or modalities) until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, imaging combined with the use of a fluorescent agent (e.g., fluorecein) can be performed to enhance recognition of pathogens that may be in the airway. The fluorescent agent can be chosen to directly tag certain pathogens (e.g., bacteria) or indirectly tag cells associated with various infectious states (e.g., neutrophils), which will then be visible. In some embodiments, such an imaging method/approach can include the steps of gaining access to the airway, delivering the fluorescent agent to within the airway, exciting the fluorescent agent by delivering an excitation signal into the airway, and assessing the presence or absence of fluorescence in response to the excitation signal.

A. Imaging for Access

In general, the methods, apparatuses, and systems disclosed herein can access pulmonary tissue or a target region (e.g., trachea, mainstem bronchi, lobar bronchi, segmental bronchi, sub-segmental bronchi, parenchyma) via a natural orifice route (e.g., from the mouth or nose), an artificially created orifice (e.g., via a tracheotomy, via a surgically created stoma, and/or any suitable intra-operative and/or surgical orifice), and/or via an artificially created orifice through the airway into other areas of the lung and/or tissue (e.g., parenchyma). The type of approach utilized can depend on factors such as a patient's age, comorbidities, need for other concomitant procedures, and/or prior surgical history.

Figure 22:
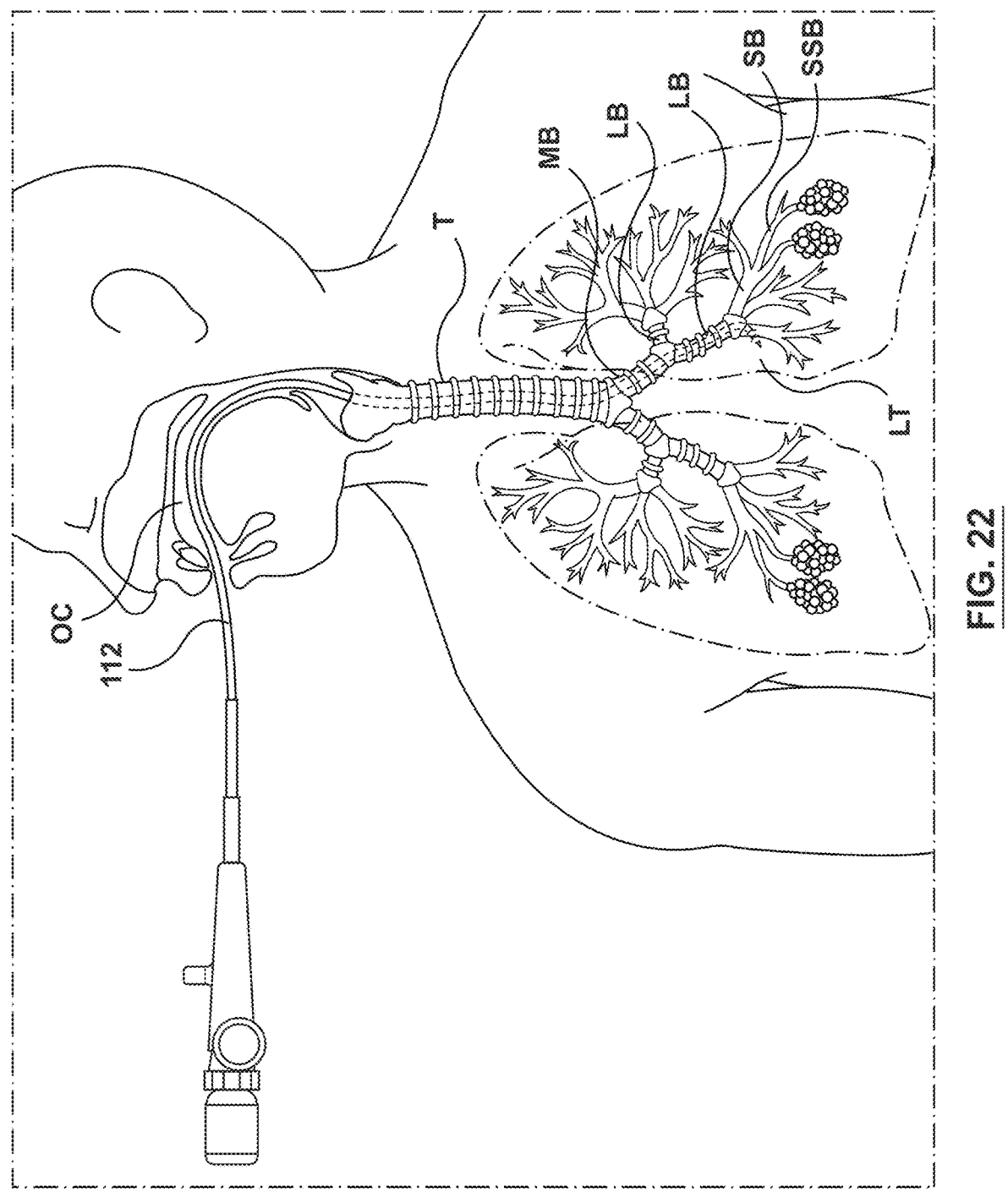
FIG. 22 illustrates accessing lung tissue, such as parenchyma, via the nose or mouth.

Methods for accessing the airway and/or other lung tissue (e.g., parenchyma) can include using the working channel of a bronchoscope delivered via the nose or mouth, into the trachea and/or more distal bronchi. As illustrated previously in FIGS. 8A-8B, a bronchoscope 112 may be inserted in the mouth or oral cavity OC of the patient P or other natural orifices such as the nose or nasal cavity NC. Similarly, other lung tissue LT, such as parenchyma, may be accessed by via the nose or mouth, as illustrated in FIG. 22. As shown, the distal end of the catheter 102 is advanced into the trachea T, the mainstem bronchi MB, and into the lobar bronchi LB crossing from an airway into the surrounding lung tissue LT. This may be achieved with a tool or catheter having a guidance system which allows for guidance outside of the lung passageway.

It may be appreciated that in some instances, direct visualization may not be necessary and/or desired, and the treatment catheter can be delivered directly into the airway via the nose or mouth.

Figure 23A:
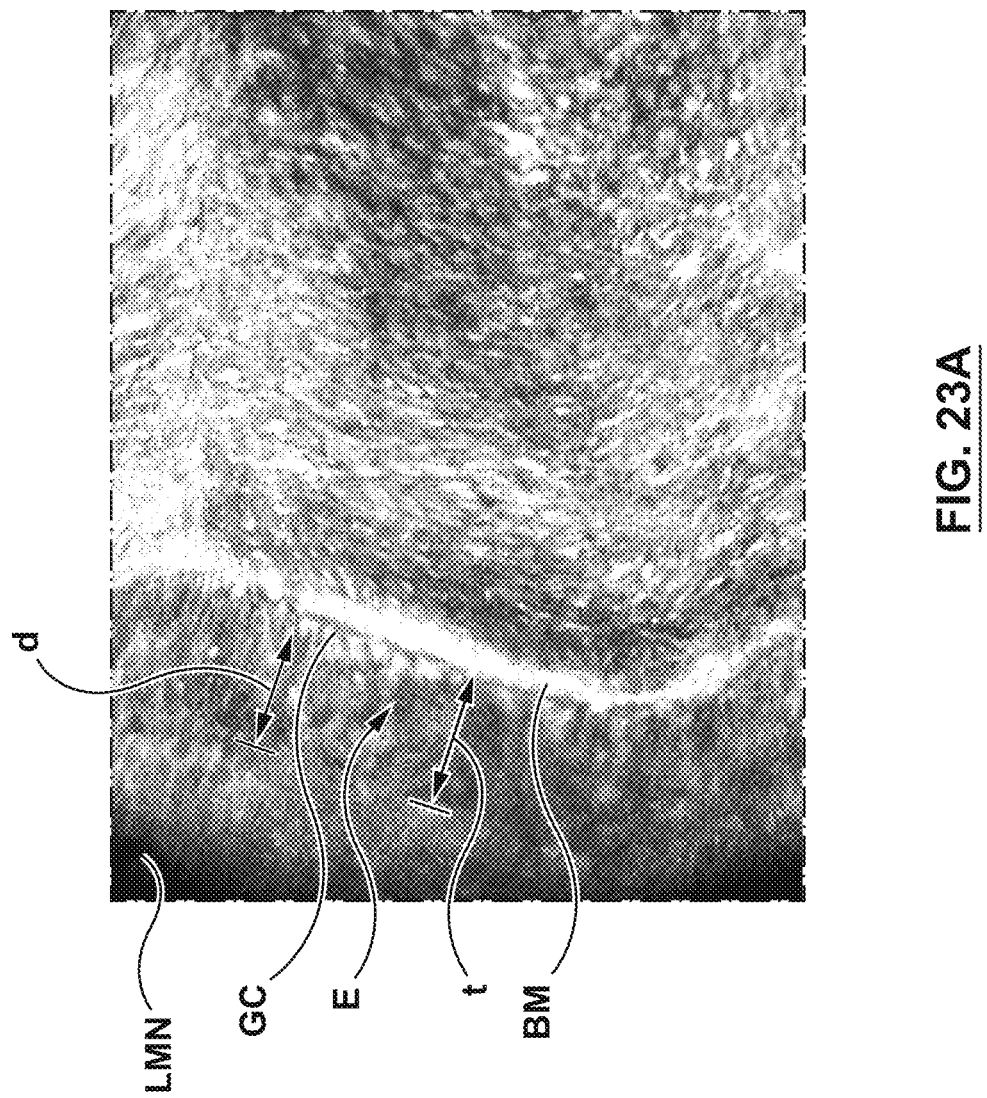
FIGS. 23A-23B depict example images of lung passageways obtainable using confocal laser endomicroscopy (CLE) and optical coherence tomography (OCT), respectively.
Figure 23B:
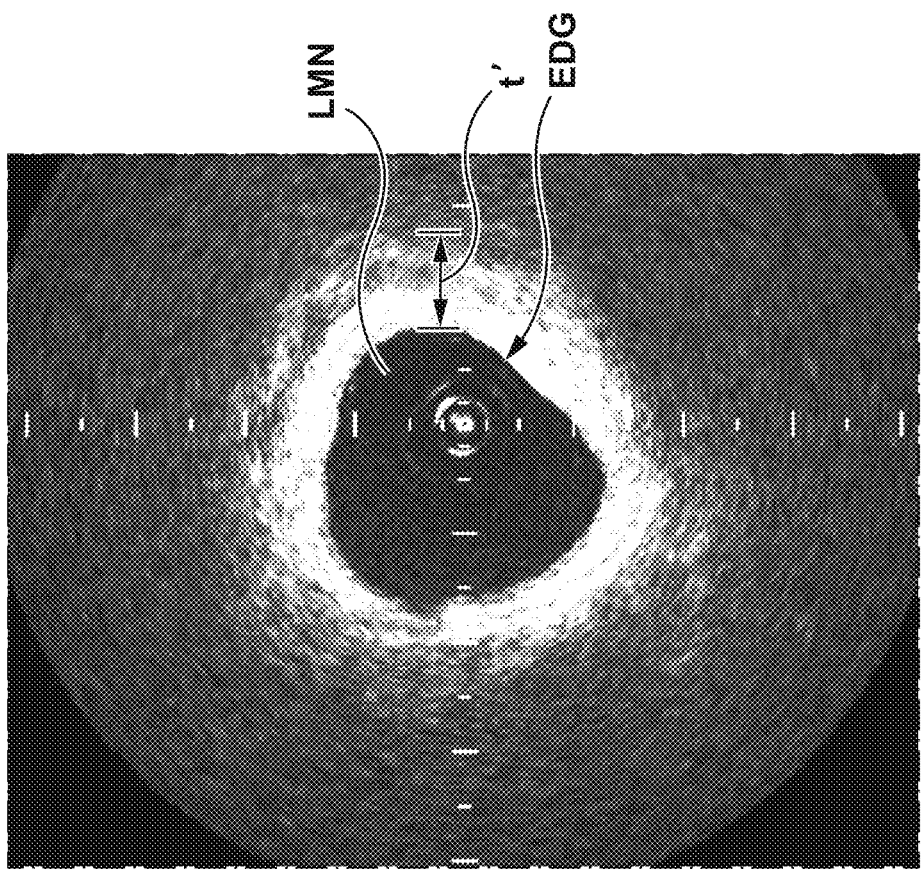

In other embodiments, accessing the airway and/or lung tissue (e.g., parenchyma) is achieved via other appliances inserted into the chest. Likewise, in some embodiments, one or more of a variety of imaging modalities (e.g., CLE, OCT) are used either along with direct visualization, or instead of direct visualization. As an example, a bronchoscope 112 can be delivered via the mouth to allow for direct visualization and delivery of the catheter 102, while an alternate imaging modality can be delivered via another working channel of the bronchoscope 112, via the nose, or adjacent to the bronchoscope via the mouth. In some embodiments, the imaging modality (e.g., direct visualization, CLE, and/or OCT) is incorporated into the catheter 102 with appropriate mechanisms to connect the imaging modality to either the system generator 104 or commercially available consoles. FIGS. 23A and 23B depict example images obtainable using CLE and OCT, respectively. These images can be used to guide delivery to a pre-determined location previously identified on CT scan using airway wall thickness (AWT) measurements, to target treatment based on visualization of cell structures, and/or to assess the effectiveness of treatment

B. Imaging for Treatment Planning

Methods associated with imaging can include using imaging pre-treatment to plan the procedure. Imaging can be used for detecting diseased target tissue, identifying areas to be treated, and/or for determining the appropriate energy delivery algorithm to achieve a desired depth of treatment. For example, a CT scan can be obtained preoperatively or intraoperatively, from which an AWT or Pi10 (theoretical airway wall thickness for an airway with an internal perimeter of 10 mm) measurement is obtained. Target zones can be identified using these metrics. Referring again to FIGS. 23A-23B, CLE or OCT can be used to measure a target treatment depth. The desired treatment depth can be based upon the thickness t of the epithelium E, as measured from the airway lumen LMN to the basement membrane BM; the distance d to a target cell type such as goblet cells GC or smooth muscle (not shown), and/or any other structure that the physician determines to be medically appropriate. FIG. 23B provides an example OCT image of a diseased airway. The thickness t' of the airway can be determined by measuring the distance from the airway lumen LMN to the outer edge EDG of the airway. Those measurements can then be used to choose a specific energy delivery algorithm 152 to achieve tissue effects to that depth. For example, the generator 104 can have a user interface 150 (such as a touch screen) that allows the selection of desired treatment depth. Once the operator chooses the desired depth, the system 100 can be configured to automatically select the appropriate energy delivery algorithm 152 to achieve that depth. Other anatomical assessments can also be made to help select target treatment sites. For example, using CLE, one can assess the size and/or density of goblet cells GC along with the distance d from the airway lumen LMN to the goblet cells GC to target both a treatment location and a target depth. These methods would allow for the therapy to be customized to each patient.

In some embodiments, the use of the bronchoscope 112 may allow for pre-procedural planning, wherein a sputum sample is acquired for analysis. If one or more pathogens are found, this information may be use for determining the appropriate energy delivery algorithm 152 to achieve a desired depth of treatment as a consequence of the initial data. In some cases, such as the combination of pathogen identification in conjunction with improved tissue imaging, it may be desirable to limit the treatment depth to merely the mucus layer M, where pathogens thrive; whereas, in other cases, it may be desirable to affect deeper airway structures. For planning the treatment, a sputum sample may be obtained and assessed to determine if an infection of the tracheobronchial tree may be present. If an infection is deemed to be present, the generator can be programmed to affect the mucus layer of the airway without substantially impacting other layers, which contains the pathogens causing the infection, or other pulmonary tissues. The method of performing sputum testing can also be used to assess the effect of the treatment. For assessing the effect of the treatment, additional sputum samples, as well as biopsies, can be taken following the energy-delivery procedure or at a later time. By comparing these samples and biopsies to the planning samples and each other, the effectiveness of the procedure can be determined. These data, combined with a clinical examination of the patient, can be used to further optimize therapy.

The method of performing one or more tissue biopsies can be used to plan treatment and/or assess the effect of the treatment. For planning the treatment, a biopsy can be performed and assessed microscopically to determine patient suitability (e.g., excessive mucus production, goblet cell density, goblet cell hypertrophy, epithelial thickness, inflammation, basement membrane thickening, submucosal inflammation, submucosal eosinophilia, submucosal gland thickening, smooth muscle hypertrophy, or other parameters) and/or degree of airway obstruction (e.g., thickness of epithelial and/or other layers). By measuring one or more of these parameters, the generator can be programmed to affect a certain depth of tissue, allowing for customization of the energy-delivery algorithm for each patient. For example, voltage can be increased for patients with thicker epithelial layers. For assessing the effect of the treatment, additional biopsies can be performed immediately following the energy-delivery procedure or at a later time. By comparing these biopsies to the planning biopsy and each other, the effectiveness of the procedure can be determined. For example, if the post treatment biopsy showed no change from the planning biopsy, either that location was not treated or insufficient energy was applied to affect the tissue. But, if the post treatment biopsy showed a reduction in epithelial thickness and/or structure (i.e., regeneration of healthy epithelium), the effectiveness of the energy delivery can be verified. By performing multiple biopsies along the airway, one could further assess whether or not a sufficient percentage of the total surface area was treated. These data, combined with a clinical examination of the patient can be used to further optimize therapy.

C. Imaging During Treatment

Use of a bronchoscope 112 allows for direct visualization of the target tissues and visual confirmation of catheter 102 placement and deployment. In some embodiments, direct visualization may not be necessary and the catheter 102 is delivered directly into the airway. Alternatively, a variety of imaging modalities (e.g., CLE, OCT) can be used either along with direct visualization or instead of direct visualization. As an example, a bronchoscope 112 can be delivered via the mouth to allow for direct visualization and delivery of the catheter 102, while an alternate imaging modality can be delivered via another working channel of the bronchoscope 112, via the nose, or adjacent to the bronchoscope via the mouth. In some embodiments, the imaging technology (e.g., direct visualization, CLE, and/or OCT) can be incorporated into the catheter with appropriate mechanisms to connect the imaging technology to either the system generator or commercially available consoles.

D. Imaging Post Treatment

In some embodiments, methods associated with imaging can include using imaging (e.g., using the imaging modality 169) to assess the effectiveness of the procedure intraoperatively and/or post procedure. In some embodiments, during the procedure, the operator can use imaging to assess target treatment areas to determine if areas were missed or insufficiently treated. For example, if an area was insufficiently treated, the operator can observe that the target depth was not achieved. The operator can then re-measure the depth, select an appropriate treatment algorithm 152, and treat again in the same location. In some embodiments, if the generator 104 does not have a variety of pre-set algorithms based on desired depth, the same energy delivery algorithm can be used. Imaging can be also used post procedure to monitor the healing process and correlate tissue changes to clinical outcomes. The healing process can make it easier to visualize tissue changes and assess the effectiveness of the procedure. These data can further lead to the physician deciding to perform additional procedures to affect additional tissue.

VII. CATHETER EMBODIMENTS

A variety of energy delivery catheter 102 embodiments are envisioned. Characteristics and features described herein can be used in any combination to achieve the desired tissue effects. Typically, such catheters 102 are sized and configured to treat lung passageways having a lumen diameter of approximately 3-20 mm. Typically, energy delivery bodies 108 expand within the lung passageway lumen so as to reside near, against, in contact, or exerting pressure or force against the wall W of the lumen. In some embodiments, the energy delivery body 108 expands to a diameter of up to 22 mm, particularly 3-20 mm or 3-22 mm.

Figure 24:
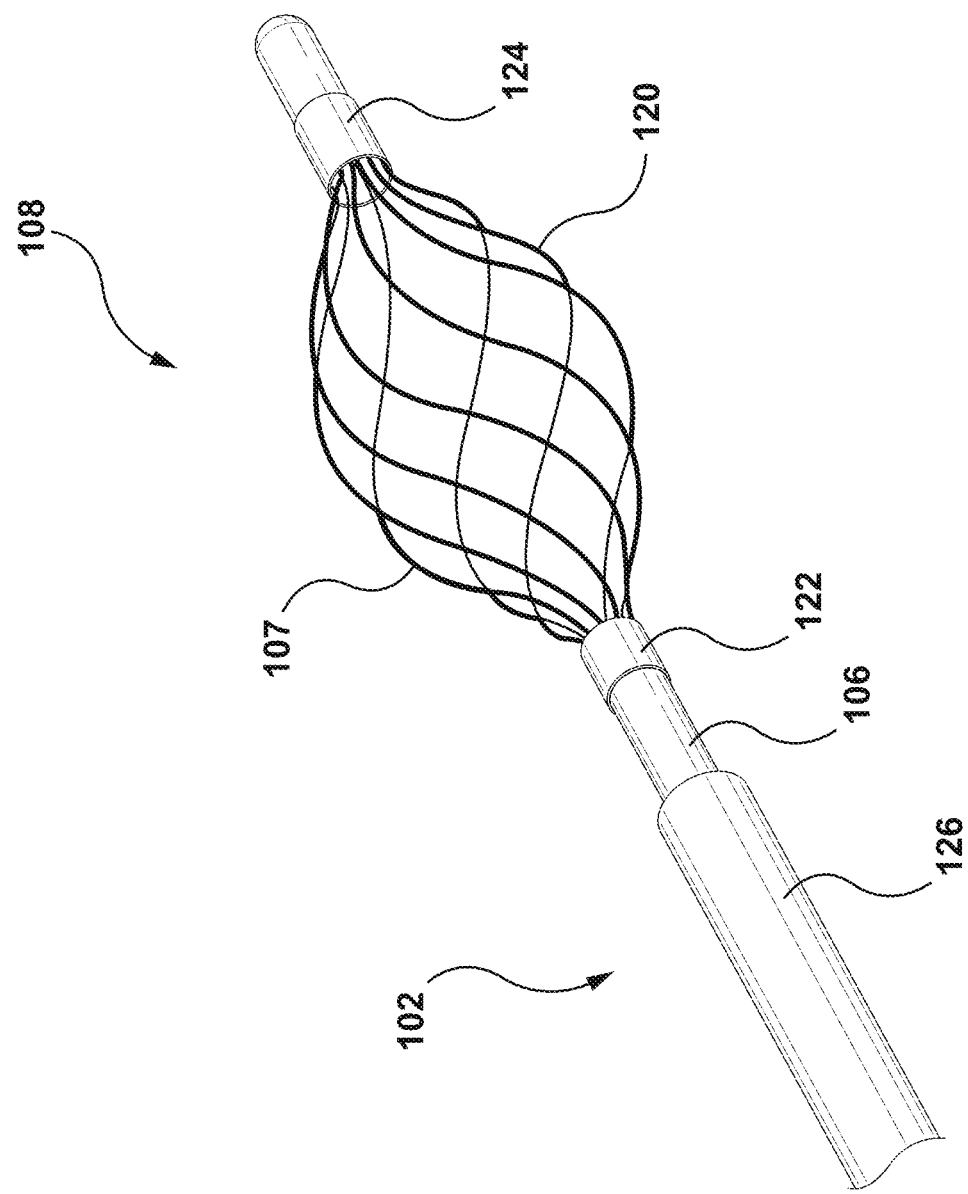
FIG. 24 depicts an embodiment of an energy delivery catheter having a single energy delivery body comprised of an electrode formed by a plurality of ribbons or wires forming a spiral-shaped basket.

FIG. 24 depicts an embodiment of an energy delivery catheter 102 having a single energy delivery body 108 comprised of at least two protrusions, each protrusion extending radially outwardly so as to contact an inner luminal wall of a lung passageway. It may be appreciated that although a single protrusion may be present, typically two protrusions are present to apply substantially opposing forces to the wall of the lung passageway to support the catheter therebetween. In this embodiment, the at least two protrusions comprise a plurality of ribbons or wires 120 which are constrained by a proximal end constraint 122 and a distal end constraint 124 forming a spiral-shaped basket. In this embodiment, the proximal end constraint 122 is attached to a shaft 106, and the shaft 106 does not pass through the energy delivery body 108. This allows the energy delivery body 108 to collapse upon itself without having the added dimension of the shaft 106 therein. The energy delivery body 108 is delivered to the targeted area in a collapsed configuration. This collapsed configuration can be achieved, for example, by placing a sheath 126 over the energy delivery body 108. In FIG. 24, since the shaft 106 terminates at the proximal end constraint 122, the distal end constraint 124 is essentially unconstrained and free to move relative to the shaft 106 of the catheter 102. Advancing a sheath 126 over the energy delivery body 108 allows the distal end constraint 124 to move forward, thereby lengthening/collapsing and constraining energy delivery body 108. Retraction of the sheath 126 allows the energy delivery body 108 to expand, such as through self-expansion. It may be appreciated that in an alternative embodiment, the ribbons or wires 120 are straight instead of formed into a spiral-shape (i.e., configured to form a straight-shaped basket). In still another embodiment, the energy delivery body 108 is laser cut from a tube.

In some embodiments, the energy delivery body 108 comprises a plurality of electrodes 107, wherein each wire 120 acts as a separate electrode 107 and is able fire separately using the wire next to it as a return electrode or using a dispersive electrode attached to the patient as a return electrode. In some instances, each wire 120 of the energy delivery body 108 can be electrically isolated from each other wire 120, and separate conductor wires can transmit the energy from the generator 104 to the wires 120 of the energy delivery body 108. In other instances, two or more wires 120 can be electrically connected to one another to form one or more sets of wires. The algorithm 152 of the generator 104 can perform the appropriate switching from one wire (or set of wires) to another as well as the alternation of the wire's function between active and return (ground) states.

Figure 25:
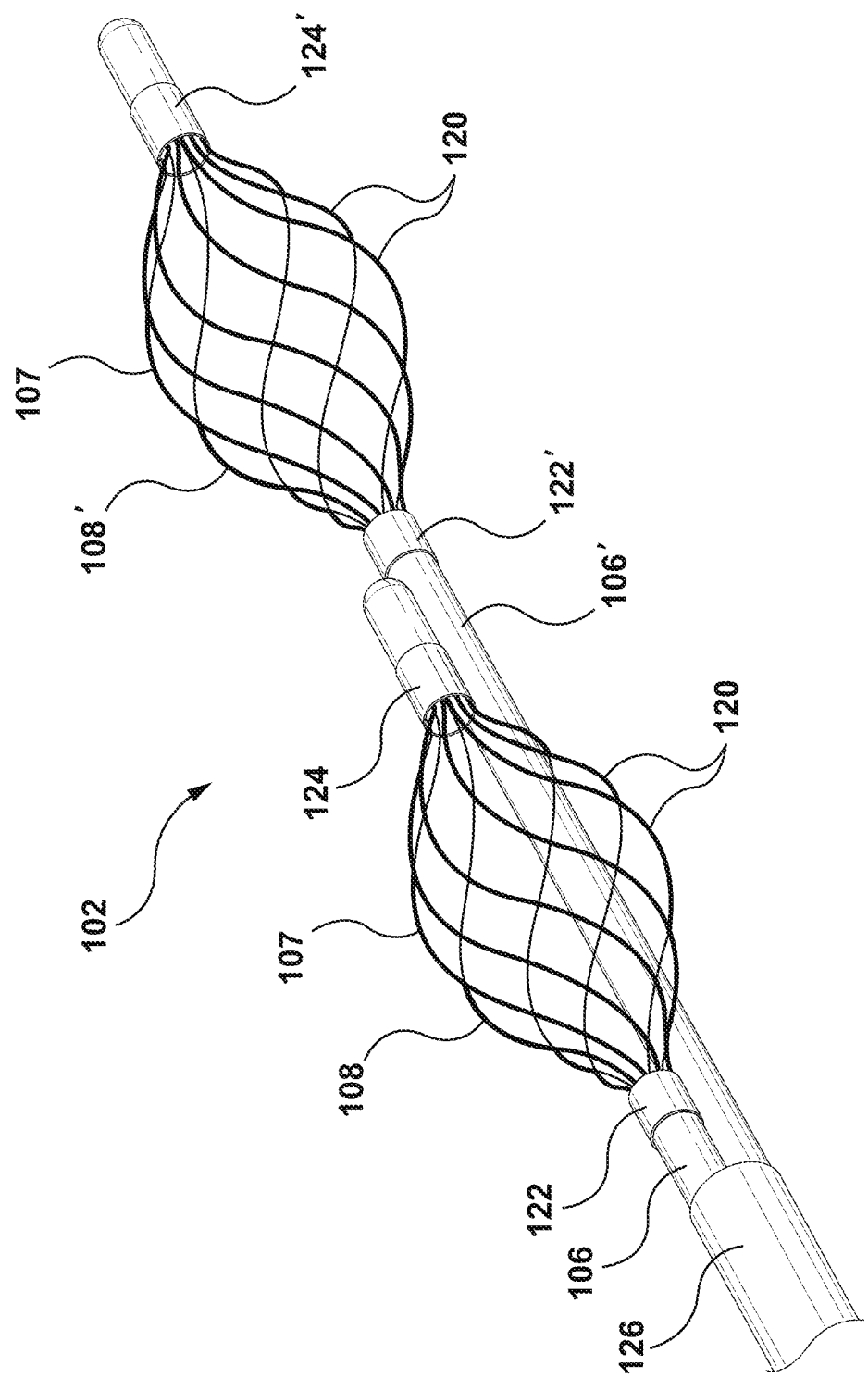
FIG. 25 depicts an embodiment wherein the energy delivery catheter includes two energy delivery bodies.

FIG. 25 depicts an embodiment wherein the energy delivery catheter 102 includes two energy delivery bodies, a first energy delivery body 108 and a second energy delivery body 108', wherein each body 108, 108' functions similarly to the embodiment of FIG. 24. In this embodiment, the first energy delivery body 108 is disposed along a distal end of a first shaft 106 and the second energy delivery body 108' is disposed along a distal end of second shaft 106'. As shown, the shafts 106,106' are aligned in parallel so that together they are passable through a sheath 126. In some embodiments, the shafts 106, 106' are fixed together so that they move in unison. In such embodiments, the shafts 106, 106' are typically arranged so that the energy delivery bodies 108, 108' are staggered, such as having the second energy delivery body 108' disposed more distally than the first energy delivery body 108, as shown in FIG. 25. In such arrangement, the energy delivery bodies 108, 108' may be separated by any suitable distance. Likewise, the energy bodies 108, 108' are arranged in relation to the shafts 106, 106' so that expansion of the energy bodies 108, 108' are not impinged by in any way. For example, in this embodiment, the energy delivery bodies 108, 108' are arranged so that the second shaft 106' does not interfere with the expansion of the first energy delivery body 108. Rather, the second shaft 106' passes through the basket-shaped energy delivery body 108, between the wires 120. In some embodiments, the shafts 106, 106' are not fixed together and are able to move in relation to each other, in particular the shafts 106, 106' are able to slide longitudinally in parallel to each other. In such embodiments, the shafts 106, 106' may be moved in relation to each other to increase or reduce the distance between the energy delivery bodies 108, 108'. Once a desired distance is achieved, the shafts 106, 106' may be fixed in place to maintain the desired distance between the energy delivery bodies 108, 108'.

In the embodiment illustrated in FIG. 25, each energy delivery body 108, 108' is comprised of a spiral-shaped basket made up of electrodes 107 in the form of wires 120. The energy delivery bodies 108, 108' can be activated in a bipolar fashion and/or a monopolar fashion. It may be appreciated that in alternative embodiments, the wires or ribbons 120 can be straight instead of formed into a spiral-shape (i.e., configured to form a straight-shaped basket). In some embodiments, the energy delivery bodies 108, 108' are laser cut from a tube. In this embodiment, the first shaft 106 terminates at the first proximal end constraint 122 of the first electrode body 108, leaving the first distal end constraint 124 essentially unconstrained. The second shaft 106' terminates at a second proximal end constraint 122' of the second electrode body 108' leaving the second distal end constraint 124' essentially unconstrained. Advancing a sheath 126 over the energy delivery bodies 108, 108' allows the distal end constraints 124, 124' to move forward, thereby collapsing, lengthening and constraining the energy delivery bodies 108, 108'. Retraction of the sheath 126 exposes the energy delivery bodies 108, 108' for expansion and delivery of energy.

Figure 26:
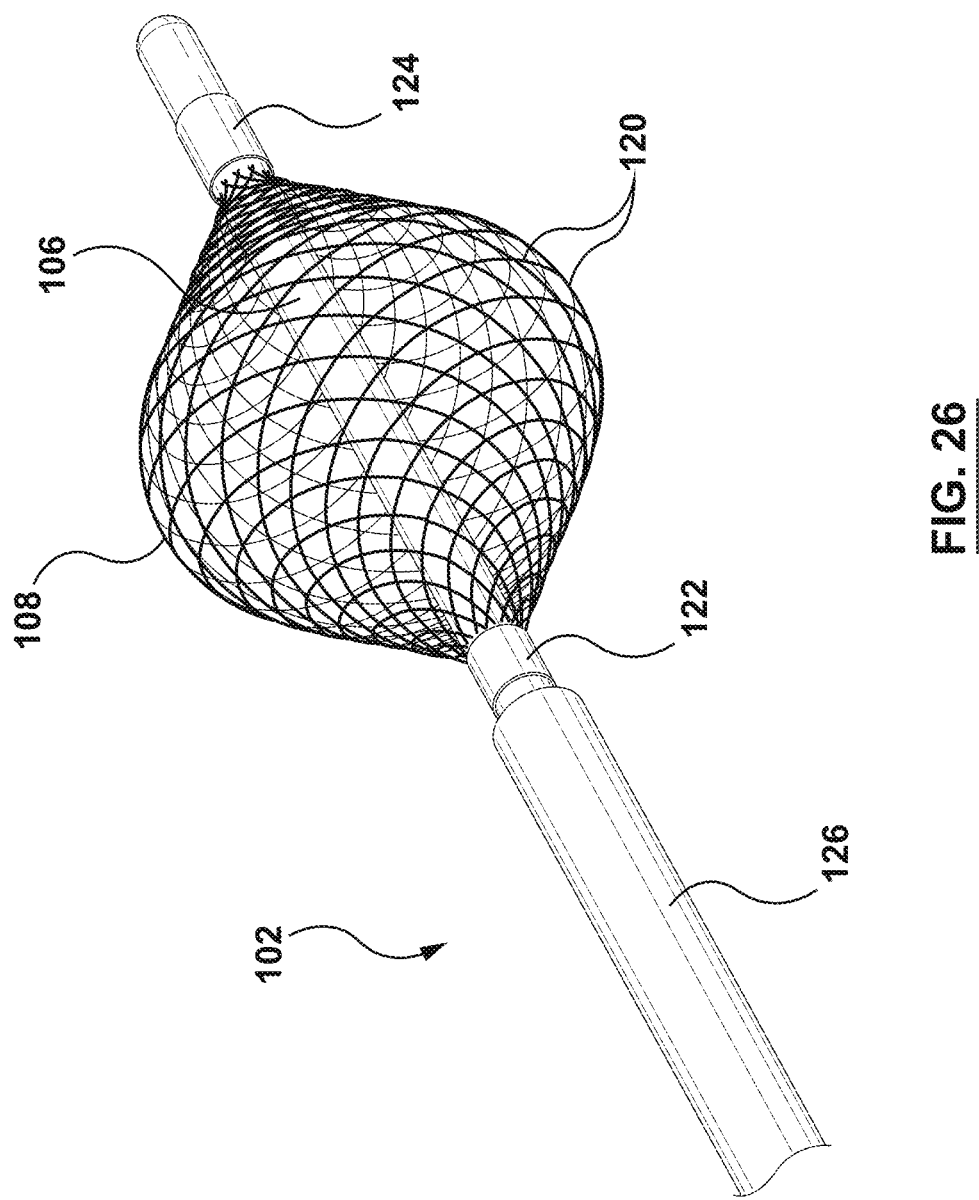
FIG. 26 depicts an embodiment of an energy delivery catheter having a single energy delivery body comprised, wherein the energy delivery body is mounted on a shaft which extends through the energy delivery body.

FIG. 26 depicts an embodiment of an energy delivery catheter 102 having a single energy delivery body 108 comprised of a monopolar electrode 107 formed by a plurality of ribbons or wires 120, wherein the energy delivery body 108 is mounted on a shaft 106 which extends through the energy delivery body 108. Again, the energy delivery body 108 has a basket shape constrained by a proximal end constraint 122 and a distal end constraint 124. In this configuration, in order for the energy delivery body 108 to collapse, either the proximal end constraint 122 or distal end constrain 124 slide freely on the shaft 106 while the other end is fixedly attached to the shaft 106. Upon the delivery of the energy delivery body 108 to the target treatment area, the sheath 126 is withdrawn by the operator via, for example, a lever or slider or plunger of the catheter's handle 110, which is operatively connected to the sheath 126. The withdrawal of the sheath 126 removes the restraint keeping the energy delivery body 108 collapsed, thus allowing its expansion leading to the wires 120 of the energy delivery body 108 contacting the bronchial wall.

In some embodiments, the collapsed configuration of the energy delivery body 108 can be achieved by mechanisms which restrict its expansion without the use of a sheath 126. For example, in some embodiments, a pull wire is attached to the proximal end constraint 122 of the energy delivery body 108 and extends down a lumen along the shaft 126 where it is operatively connected to a lever, slider, or plunger of the catheter's handle 110. In this embodiment, the distal end constraint 124 is fixedly attached to the shaft 106 and the proximal end constraint 122 is configured to slide freely on the shaft 106. While the pull wire is under pull force, the proximal end constraint 122 is positioned so that the energy delivery body 108 is collapsed. The pull wire can be maintained in this position by restraint within the handle 110. Release of the pull force, such as by reduction or removal of the restraint within the handle 110, allows the pull wire to move, thus freeing the proximal end constraint 122 and allowing it to travel closer to its distal end constraint 124 as self-expanding properties of the energy delivery body 108 cause expansion.

In other embodiments, the proximal end constraint 122 is affixed to the shaft 106 and the distal end constraint 124 is free to slide on the shaft 106. Further, a push rod (or tubing to achieve higher column strength) is attached to the distal end constraint 124 and extends down a lumen along the inner shaft 106 where it is operatively connected to mechanism such as a lever, slider, or plunger of the catheter's handle 110. When the push rod is pushed and subsequently restrained within the handle 110 of the catheter 102, the distal constraint 124 is moved away from the proximal end constraint 122 which causes the energy delivery body 108 to collapse. When the energy delivery body 108 is self-expanding, release of the push rod allows the energy delivery body 108 to expand. Alternatively, the push rod may be retracted, pulling the distal end constraint 124 toward the proximal end constraint 122 which causes the energy delivery body 108 to expand.

In the embodiment shown in FIG. 26, the energy delivery body 108 is formed b a braided metal tube constrained at both the proximal end constraint 122 and the distal end constraint 124 and configured to form a basket. The energy delivery body 108 can be controlled (i.e., collapsed, deployed) as described above. When the energy delivery body 108 comprises a braided metal tube, each wire in the braided tube is supported by multiple wires next to it as well as by the interwoven nature of the braid itself. This support and interwoven configuration can assure minimal variation in space between wires, otherwise known as pore or opening size of the braid. In addition, this support and interwoven configuration can allow constructing the braided tube from very small wires and yet have significant radial stability of the basket. This allows the use of many wires (e.g., 12, 16, 18, 20, 22, 24, etc.) while maintaining a relatively small profile of the energy delivery body 108 in the collapsed/constrained state and optimizing the opening size of the braided tube when electrode(s) is/are deployed/expanded. In this embodiment, the space between wires is rather small, leading to a treatment that is essentially continuous over 360 degrees of the inner lumen of a lung passageway.

Figure 27:
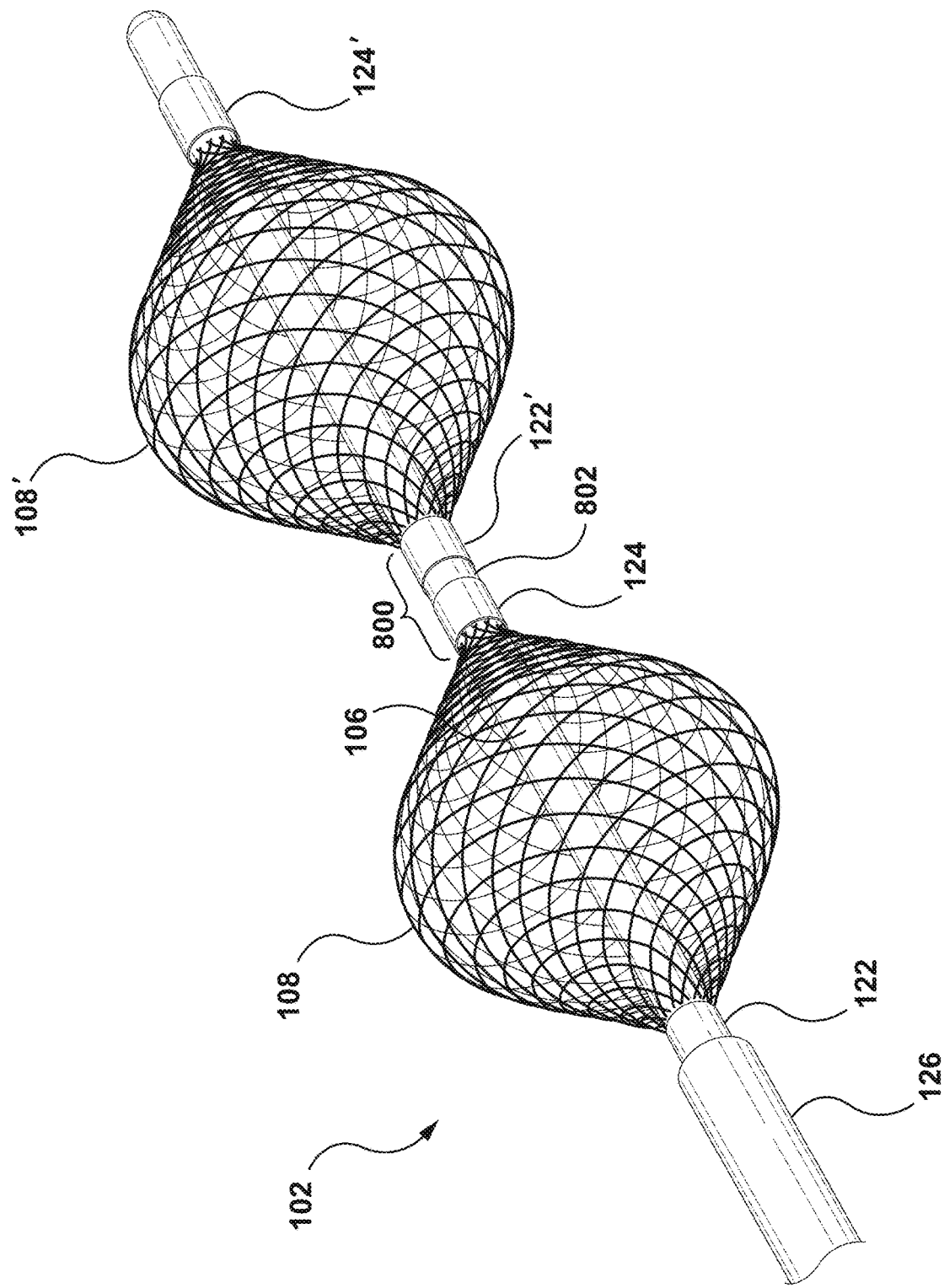
FIG. 27 illustrates an embodiment wherein both energy delivery bodies are carried on a single shaft.

FIG. 27 illustrates an embodiment wherein both energy delivery bodies 108, 108' are carried on a single shaft 106. In order for the energy delivery bodies 108, 108' to collapse, the first proximal end constraint 122 of the first energy delivery body 108 is fixedly attached to the catheter shaft 106. The other end constraints 122', 124, 124' are able to slide freely on the catheter shaft 106. The catheter is delivered with a sheath 126 constraining the energy delivery bodies 108, 108'. Upon delivery of the energy delivery bodies 108, 108' to the target area, the sheath 126 can be withdrawn by the operator via, for example, a mechanism such as a lever or slider or plunger of the catheter's handle 110. The withdrawal of the sheath 126 removes the restraint keeping energy delivery bodies 108, 108' collapsed, thus allowing their expansion leading to the surfaces of the energy delivery bodies 108, 108' contacting the bronchial wall. In addition, in some embodiments, the first distal end constraint 124 and the second proximal end constraint 122" are connected to each other via coupler 800. The coupler 800 is constructed using an electrically insulative material (e.g. polyether block amide (Pebax®) tubing, polyimide tubing, etc.) to provide an insulative gap 802 between energy delivery bodies 108, 108' to achieve electrical discontinuity between them. In some embodiments, this gap 802 is between 1 and 20 mm. This prevents arcing within the catheter shaft 106.

In some embodiments, the collapsed configuration of the energy delivery bodies 108, 108' can be achieved by restricting their expansion without the use of a sheath 126. For example, in one embodiment the distal end of a pull wire (not shown) is attached to the second distal end constraint 124' and the proximal end of the pull wire is attached to a mechanism of the handle 110 (for example plunger, slider or lever). The first proximal end constraint 122 is fixedly attached to the catheter shaft 106 and the other end constraints 124, 122', 124' slide freely over the catheter shaft 106. Such a configuration assumes that energy delivery bodies 108, 108' are in a collapsed configuration prior to initiating placement via a bronchoscope and require the operator to deploy/expand them. This deployment/expansion is achieved by the operator activating the mechanism of the handle 110 (e.g. lever, plunger or slider) which pulls the second distal end constraint 124' toward the first proximal end constraint 122, thus effectively deploying/expanding both energy delivery bodies 108, 108'. In another configuration, expansion can be achieved by employing two pull wires, one attached separately to each energy delivery body 108, 108'. In such embodiments, the operator can control the level of expansion of the energy delivery bodies 108, 108' separately.

In some embodiments, the one or more energy delivery bodies 108, 108' are not constrained at both ends, rather one end is unconstrained creating a half-basket shape. FIG. 28A illustrates an embodiment wherein one energy delivery body energy 108' is unconstrained at one end forming a half-basket shape when expanded. In this embodiment, both the energy delivery bodies 108, 108' are comprised of braided metal wires. The distal-most energy delivery body 108' is constrained at both the second proximal end constraint 122' and the second distal end constraint 124' and configured to form a closed braided basket shape. The distal-most energy delivery body 108' is expandable so that typically at least the widest expansion diameter contacts the wall W of the lung passageway. The most proximal or first energy delivery body 108 is constrained at a first proximal end constraint 122 and configured to form an approximately half-open basket or half-basket shape when expanded, as shown. The proximal energy delivery body 108 is expandable so that typically at least the widest expansion diameter contacts the wall W of the lung passageway. The shaft 106 is fixedly attached to the first and second proximal end constraints, 122, 122'. The half basket shape of the proximal energy delivery body 108 allows its widest expansion diameter to be closer to that of the distal-most energy delivery body 108' than would otherwise be the case if the proximal energy delivery body 108 were whole shaped. Decreasing this distance between the energy delivery bodies 108, 108' allows for a treatment effect between the energy delivery bodies 108, 108' in addition to at the energy bodies 108, 108'. This ultimately creates a larger surface treatment effect given the effect between the bodies 108, 108'. In addition, the half basket shape may help avoid arcing.

The configuration depicted in FIG. 28A is delivered with the use of a sheath (not shown) as described in detail above, wherein both energy delivery bodies 108, 108' are self-expandable. In another embodiment, the second energy delivery body 108' is placed in a collapsed state prior to delivery into a bronchoscope and once positioned in a desired target area, deployed/expanded via a pull wire (not shown) connected to its second distal end constraint 124') and to a mechanism in the handle 110. This combination of full-basket (energy delivery body 108') and half-basket (energy delivery body 108) can be employed for bipolar or monopolar energy delivery. When electrodes are made of a braided metal wires, each wire is supported by multiple wires next to it as well as by the interwoven nature of the braid itself. This support and interwoven configuration can assure minimal variation in space between wires otherwise known as pore or opening size of the braid. In addition, this support and interwoven configuration allow constructing the braid from very small wires and yet have significant radial stability of the basket. This allows the use of many wires (for example 12, 16, 18, 20, 22, 24, etc.) while maintaining small profile of the energy delivery bodies 108, 108' in a collapsed or constrained state while optimizing the opening size of the braid when the energy delivery bodies 108, 108' are deployed or expanded. In this embodiment, the space between wires is rather small, leading to a treatment that is 360 degrees within a lung passageway.

FIG. 28B illustrates an embodiment wherein both the energy delivery bodies 108, 108' are comprised of braided metal wires with the proximal end constraints 122, 122' affixed to the shaft 106. In this embodiment, both energy delivery bodies 108, 108' are configured to form half-baskets. This configuration is sheath (not shown) may be delivered with the use of a sheath as described above, wherein the energy delivery bodies 108, 108' are self-expandable. This configuration of half-basket energy delivery bodies 108, 108' can be employed for bipolar and/or monopolar energy delivery.

In some embodiments, the entire surface of the one or more energy delivery bodies 108 is energized by the energy signal for delivery to the target tissue. However, in other embodiments, an active surface area of the energy delivery body 108 is provided wherein the remaining portions are not active. In some embodiments, this is achieved by partially insulating one or more portions of the energy delivery body 108 leaving one or more active region(s). For example, FIG. 29 illustrates a braided wire basket energy delivery body 108 comprised of energizable wires 120 (acting as one or more electrodes) wherein some of the wires 120 are insulated with portions of the insulation removed to define an active area 820. In some embodiments, the insulation is removed from the outer (tissue contacting) surface of the wire 120. This approach can be useful, for example, if the measured impedance via the electrode wire 120 is affected by the amount of the exposed metal and if it is desirable for the measured impedance to represent the electrode-to-tissue interface. In other embodiments, the insulation can be removed on both the outer and inner surfaces of the electrode wire 120. One method for manufacturing an energy delivery body 108 with this configuration involves creating a braid using insulated wires, then using appropriate means (e.g., laser, mechanical) to remove the insulation to create one or more active areas 820. While this example depicts a single active area 820, a plurality of active areas is also envisioned in order to generate any treatment pattern. Similar techniques can also be employed for non-braided energy delivery bodies 108 described herein. In these embodiments, the insulation can be applied or removed as part of the manufacturing process to define any active area (or areas) 820 configuration desired to achieve various treatment patterns.

FIG. 30 illustrates another embodiment wherein a metal (e.g. Nitinol) tube 830 is laser cut to form a collapsed basket 832 with both ends constrained via the tube 830 itself. The basket 832 can then be expanded and shape set, such that it can self-expand during use, so as to perform as the energy delivery body 108. Alternatively, push/pull mechanisms can be employed to expand/collapse the basket 832 for delivery and treatment. In some embodiments, one end 834 of the basket 832 is removed to create free ends 836, as illustrated in FIG. 31. Insulation (e.g., polymer tubing) can then be advanced over the free ends 836 and applied to portions of the basket 832. In some embodiments, the insulation is applied to proximal and distal portions of the basket, leaving one or more conductive/active areas 820 therebetween. In other embodiments, as shown in FIG. 31, the wires 120 of the basket 832 are insulated and one or more separate additional electrodes 840 (shown as coils) are connected to the insulated basket wires to form active areas 820. This assembly can then be affixed to a catheter 102 such that the energy delivery body 108 can be activated as a monopolar electrode with multiple pre-defined active areas 832.

FIG. 32 illustrates another embodiment of an energy delivery body 108. In this embodiment, the body 108 comprises a plurality of tines 840, similar to the free ends 836 of FIG. 31. The tines 840 are able to expand outwardly so as to contact the lung passageway wall. In some embodiments, one or more of the tines 840 are insulated with insulation material 842. Electrodes 107 disposed along each tine 840, such as near the distal ends of each tine 840, can be created by removal of the insulation material 842 to expose an underlying energizable element or wire. Alternatively, a separate electrode 107 may be mounted on the insulation material 842, as depicted in FIG. 32. In some embodiments, the tines 840 are formed of polymer-covered wires, wherein the wire can act as structural support to self-expand the tines 840, can be energizable to deliver treatment energy and/or can be used to sense temperature and/or impedance. In some embodiments, the tines 840 are collapsible via a sheath 126 for delivery and allowed to expand into contact with the tissue upon retraction of the sheath 126. The electrodes can all fire simultaneously in a monopolar fashion, can fire independently in a monopolar fashion, and/or fire between one another in any pattern necessary to generate the desired treatment effect. The length of the electrodes can range from about 3 mm to about 5 cm, such as 3 mm, 5 mm, 1 cm, 2 cm, 3 cm, 4 cm or 5 cm. While depicted as all the same size in FIG. 32, the size (e.g., length, width) can vary.

Figure 33:
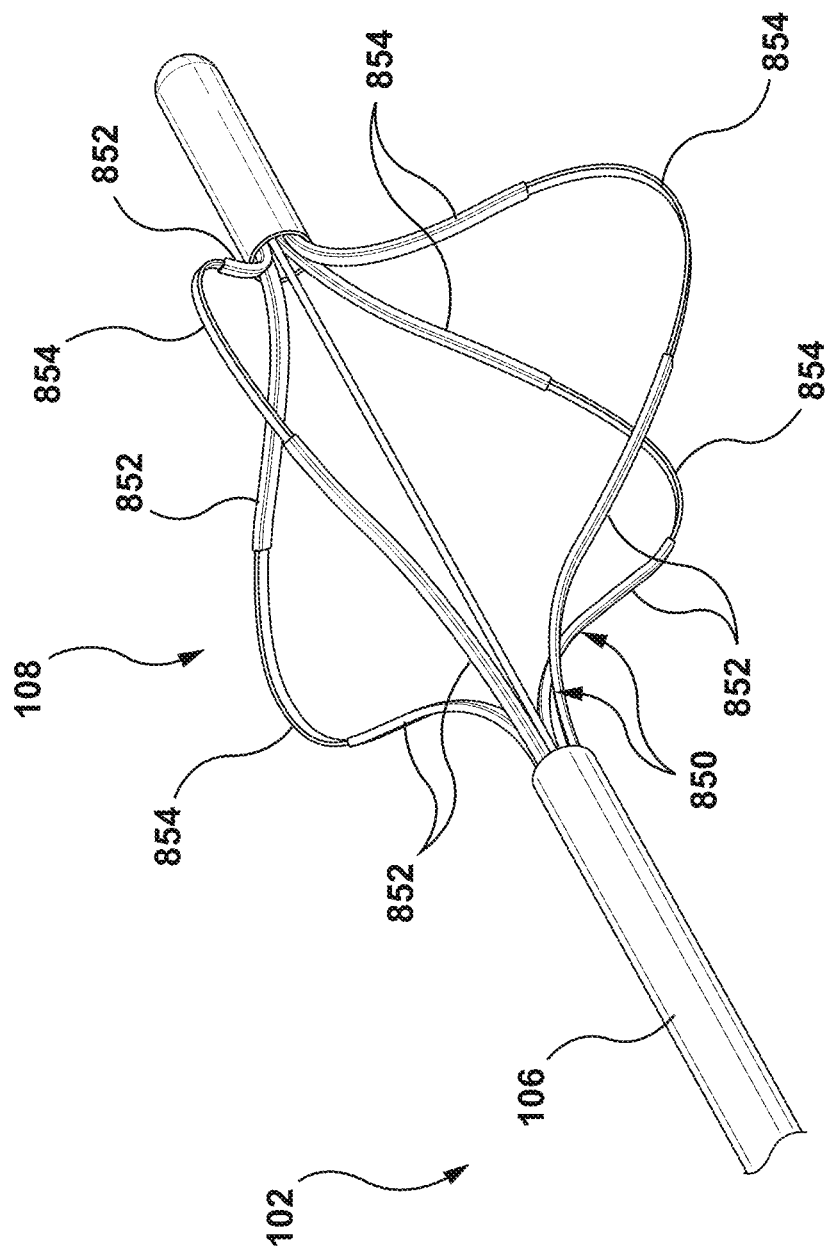
FIG. 33 illustrates an embodiment of an energy delivery body comprising one or more protrusions.

FIG. 33 illustrates another embodiment of an energy delivery body 108. In this embodiment, the energy delivery body 108 comprises one or more protrusions 850 rather than a basket weave. Each protrusion 850 is formed by a wire or ribbon 120 which acts as an electrode and bends radially outward from the longitudinal axis or shaft 106 of the catheter 102. In this embodiment, each protrusion 850 is electrically isolated from each of the other protrusions. The protrusions 850 may be comprised of a variety of suitable materials so as to act as an electrode, such as stainless steel, spring steel, or other alloys, and may be, for example, round wires or ribbon. Each protrusion 850 is insulated with a segment of insulation 852, such as a polymer (e.g., PET, polyether block amide, polyimide), over at least a portion of the proximal and distal ends of the energy delivery body 108. The exposed portion 854 of the wire or ribbon can then act as an electrode on each protrusion 850. In one embodiment, the exposed portions 854 of the protrusions 850 are completely free of insulation 852. In another embodiment, the insulation 852 is removed only from the outer surface of the protrusion 850 leaving the side of the protrusion 850 that does not come in contact with the tissue (e.g., an inner surface that faces the shaft 106 of the catheter 102) completely insulated. In one embodiment, each protrusion 850 is energized independently, with two protrusions 850 acting as neutral electrodes (return) and two protrusions 850 acting as active electrodes. Neutral and active electrodes can be positioned right next to each other. Neutral electrodes located 180 degrees from each other (opposite electrodes) can be electrically connected to each other and so can be the active electrodes. In this embodiment, only two conductive wires (power lines) are needed to connect two pairs of protrusions 850 to the generator 104. Further, pairs of protrusions 850 that are utilized in a bipolar fashion can further be multiplexed to allow for any combination or rotation of active versus neutral electrode. The generator 104 can be configured to have sufficient channels to support any of these approaches (i.e., 1 to 4 channels). This embodiment of the energy delivery body 108 can optionally be delivered in a collapsed configuration and expanded into tissue contact via a pullback wire and mechanism within the handle.

Figure 34:
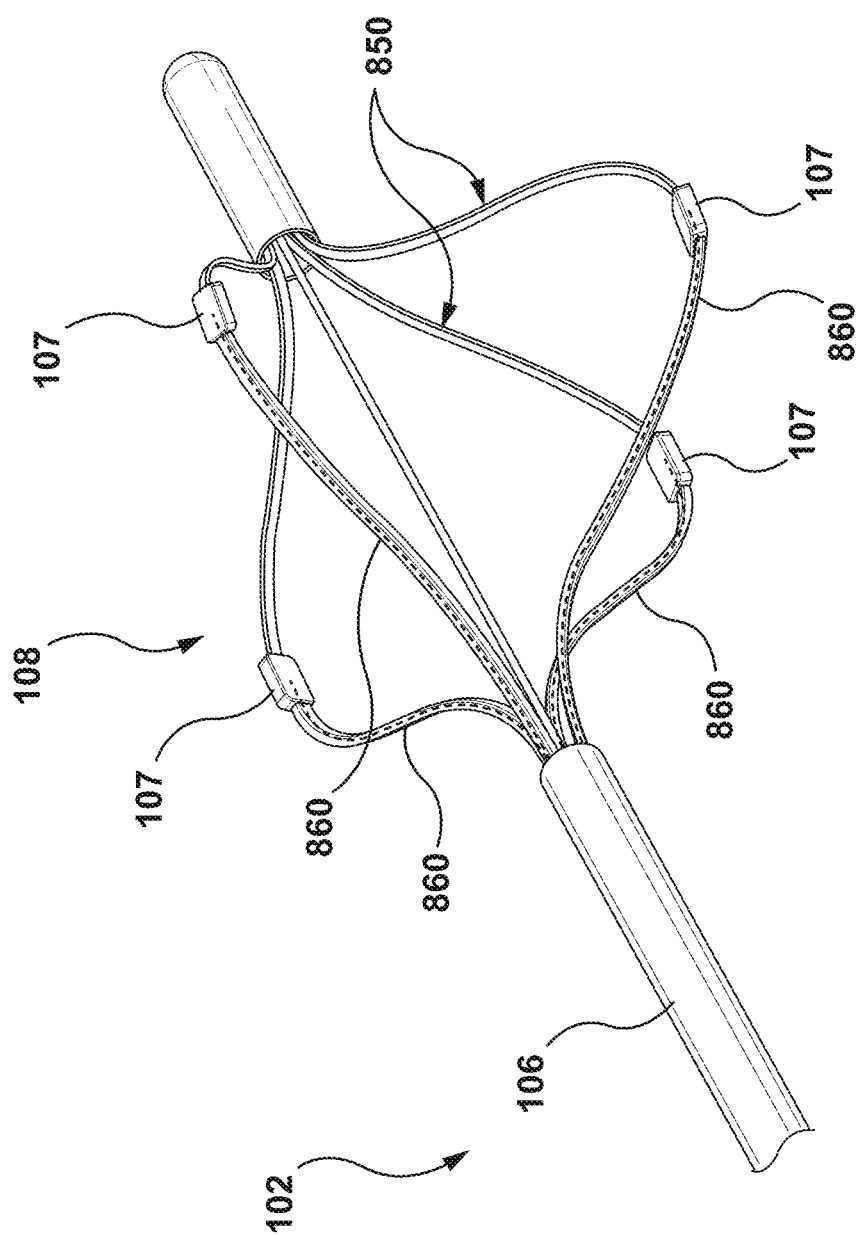
FIG. 34 illustrates an embodiment of energy delivery body comprising one or more protrusions wherein each protrusion is formed from a non-conductive material and carries, supports, and/or is otherwise coupled to a separate electrode.

FIG. 34 illustrates another embodiment of energy delivery body 108 comprising one or more protrusions 850 wherein each protrusion 850 bends radially outward from the longitudinal axis or shaft 106 of the catheter 102. However, in this embodiment, each protrusion 850 is formed from a non-conductive material and carries, supports, and/or is otherwise coupled to a separate electrode 107. Each electrode 107 has a conductive wire 860 connecting the electrode 107 to the generator 104. The protrusions 850 position said electrodes 107 against the tissue upon expansion, such as via a pull wire and mechanism within the handle. In this embodiment, each electrode 107 is placed over or adjacent each protrusion 850. If the protrusions 850 are comprised of a metal, insulation is provided to electrically isolate the electrodes 107 from the protrusions 850 themselves. If the protrusions 850 are comprised of a polymer or other non-conductive material, additional insulation would not be required. In some embodiments, the protrusions 850 are comprised of round wire or ribbon and configured to form a straight basket, as shown. In other embodiments (not shown), the protrusions 850 are configured in a spiral shape. It may be appreciated that separate electrodes 107 as depicted in FIG. 34 may likewise be applied to other embodiments, such as wherein the basket is comprised of a braided material. Similar to the embodiment of FIG. 33, each electrode 107 may be energized in a variety of combinations. Furthermore, each protrusion 850 can carry the electrodes 107 that can be electrically connected to each other or electrically insulated from each other. To increase the surface area of the electrodes 107 each can be constructed from, for example, a metallic coil or in a form of a slotted (e.g. laser cut) tube. These configurations would allow for greater spatial coverage and yet maintain the flexibility of the electrodes 107 to allow the protrusions 850 of the basket to bend and straighten freely. As in FIG. 33, the surface of the protrusions 850 can be completely exposed or insulated over areas that do not come in contact with the tissue.

FIG. 35 illustrates another embodiment of a catheter 102 having at least one energy delivery body. In this embodiment, each energy delivery body comprises an expandable coil that can either act an electrode itself or can act as a carrier for separate electrodes mounted thereon. In this embodiment, the catheter 102 comprises two energy delivery bodies, a first energy delivery body 108 which is disposed proximally to a second energy delivery body 108'. Each energy delivery body 108, 108' has the shape of an expandable coil. A distal end 870 of the second energy delivery body 108' is coupled with or formed to an inner member 872, and a proximal end 874 of the first energy delivery body 108 is coupled with an outer member 876. The outer member 876 is rotatable relative to the inner member 872 to collapse and/or expand the energy delivery bodies 108, 108'. A coupler 878 attaches the energy delivery bodies 108, 108' together and provides insulation between them, if desired. The energy delivery bodies 108, 108' can be activated in a monopolar and/or bipolar fashion. The size of the energy delivery bodies 108, 108' can be the same or different, as described herein. The length of each expanded coil can range from about 5 mm to about 20 mm.

FIG. 36 depicts an energy delivery body 108 configured for more limited application of treatment energy, such as in a narrow region along the lung passageway wall or along a partial inner circumference of the lung passageway. In this embodiment, the energy delivery body 108 comprises a coil that limits the length of the active area. Such embodiments can be employed if very focal tissue effects are desired or if tissue effects extend beyond the active area in contact with tissue. In this embodiment, the energy delivery body 108 comprises a coil 880 having a width and a length, wherein the length of the coil 880 can be pre-shaped into a semi-circular or circular pattern, as shown. The treatment length L1 is provided by the width of the coil 880 as it contacts the lung passageway wall W. This configuration can be activated in a monopolar configuration as depicted; however, it is further envisioned that two or more coils 880 can be employed to allow for bipolar and/or multiplexed energy delivery. Similarly, FIG. 37 illustrates an embodiment of an energy delivery body 108 comprising a rod 882 (such as shaft 106) having a width and a length, wherein the length of the rod 882 is pre-shaped into a semi-circular or circular pattern, as shown. The rod 882 includes one or more electrodes 107 disposed along its length. The one or more electrodes 107 may be embedded into or otherwise affixed to the rod 882. The treatment length L1 is provided by the width of the one or more electrodes 107 which contact the lung passageway wall W. This embodiment allows for monopolar activation between all electrodes and a dispersive (neutral) electrode, bipolar activation between individual electrodes, and/or multiplexed activation between any combination of electrodes. It is further envisioned that two or more of these devices can be employed to allow for energy delivery between them. When the energy delivery bodies 108 are pre-shaped into the semi-circular or circular configuration, a sheath 126 can be used to collapse and constrain the energy delivery body 108 for self-expansion and/or a pull/push wire can be used to expand the energy delivery body 108. These methods for expanding and/or collapsing an energy delivery bodies 108 are described in detail within other examples provided.

The energy delivery body 108 can be optimized for situations in which force exerted onto the bronchial wall is desired to be more highly controlled. In this embodiment, the energy delivery body 108 is delivered into the bronchial lumen via a three-step process. First, as illustrated in FIG. 38, a sheath 126 is withdrawn proximally thus exposing one or more prongs 900 which act as protrusions. This embodiment includes four prongs 900 arranged symmetrically around a central lumen 902, as illustrated in the cross-sectional illustration of FIG. 38A. It may be appreciated that any number of prongs 900 may be present including one, two, three, four, five, six or more. Each prong 900 includes at least one electrode 107. FIG. 39 illustrates an embodiment of a prong 900 having two electrodes 107 having an elongate shape (such as wire) attached to an insulating substrate 904, such as a polymer substrate (e.g. ribbon, strip), therebetween as a means to maintain distance between the electrodes 107. It may be appreciated that the electrodes 107 may have a round or square/rectangular cross-section, and are typically affixed to the insulating substrate 904 such that the electrodes 107 are substantially parallel to one another. The manufacturing method of attaching the electrodes 107 to the insulating substrate 904 can employ (but is not limited to) co-extrusion, deposition, adhesive based bonding, and thermal bonding. The width of the insulting substrate 904 can vary.

FIG. 40 illustrates an embodiment of a prong 900 having a narrower insulating substrate 904 than depicted in FIG. 39. Likewise, FIG. 41 illustrates an embodiment of a prong 900 having yet narrower insulating substrates 904 and greater than two electrodes 107. In particular, FIG. 41 illustrates five electrodes 107, however it may be appreciated that any number of electrodes 107 may be present, such as one, two, three, four, five, six, seven, eight or more. FIG. 42 illustrates a plurality of electrodes 107 mounted on a polymer substrate (e.g. ribbon, strip) wherein the electrodes 107 have an elongate shape (such as wire) and are positioned substantially in parallel to each other leaving a gap between each wire.

In some embodiments, the insulating substrate 904 with electrodes 107 is configured as a strip (FIGS. 39-42). Thus, the electrodes 107 are deployed as a linear strip positioned along a length of an airway. In other embodiments, the insulating substrate 904 with electrodes 107 is configured as a helix wherein the electrodes are deployed in a helical fashion. FIG. 43 illustrates the insulating substrate 904 with electrodes 107 as shown in FIGS. 39-40 configured as a helix. FIG. 44 illustrates the insulating substrate 904 with electrodes 107 as shown in FIG. 41 configured as a helix.

In some embodiments, a push-pull mechanism as described previously in relation to other embodiments can be employed to deploy the strip or ribbon. In case of the helix, the rotational mechanism can also be used. Electrodes 107 can be electrically connected to each other, can be insulated from each other or different patterns of electrical interconnection between electrodes depending on the energy application algorithm controlled by the generator.

Once the one or more prongs 900 are exposed, the second step of the three-step process involves introducing an expandable member 910, such as a balloon, by advancing the expandable member 910 from the lumen 902 while in an unexpanded state. The third step involves expanding the expandable member 901, such as inflating the balloon, as illustrated in FIGS. 45A-45B, until a desired interface between the prongs 900 (and therefore electrodes 107) and bronchial wall W is achieved. In another embodiment, the prongs 900 are positioned while the expandable member 910 is already disposed beneath the prongs 900 so their relative longitudinal position does not change. In this configuration, the withdrawal of the sheath 126 exposes both the expandable member 910 and the prongs 900 at the same time, thus eliminating the step of advancing the expandable member 910 out of the lumen 902. As described above, the expandable member 910 is subsequently expanded (e.g. inflated) until the desired interface between the prongs 900 and bronchial wall S is achieved. The size (e.g. length, width) of the prongs 900 can be the same or different. The number of prongs 900 can vary between 1 (monopolar configuration) and 100 (monopolar and/or bipolar) configuration. Energy application to the electrodes 107 can vary widely depending on the algorithm of the energy delivery apparatus (e.g. generator).

Figure 46:
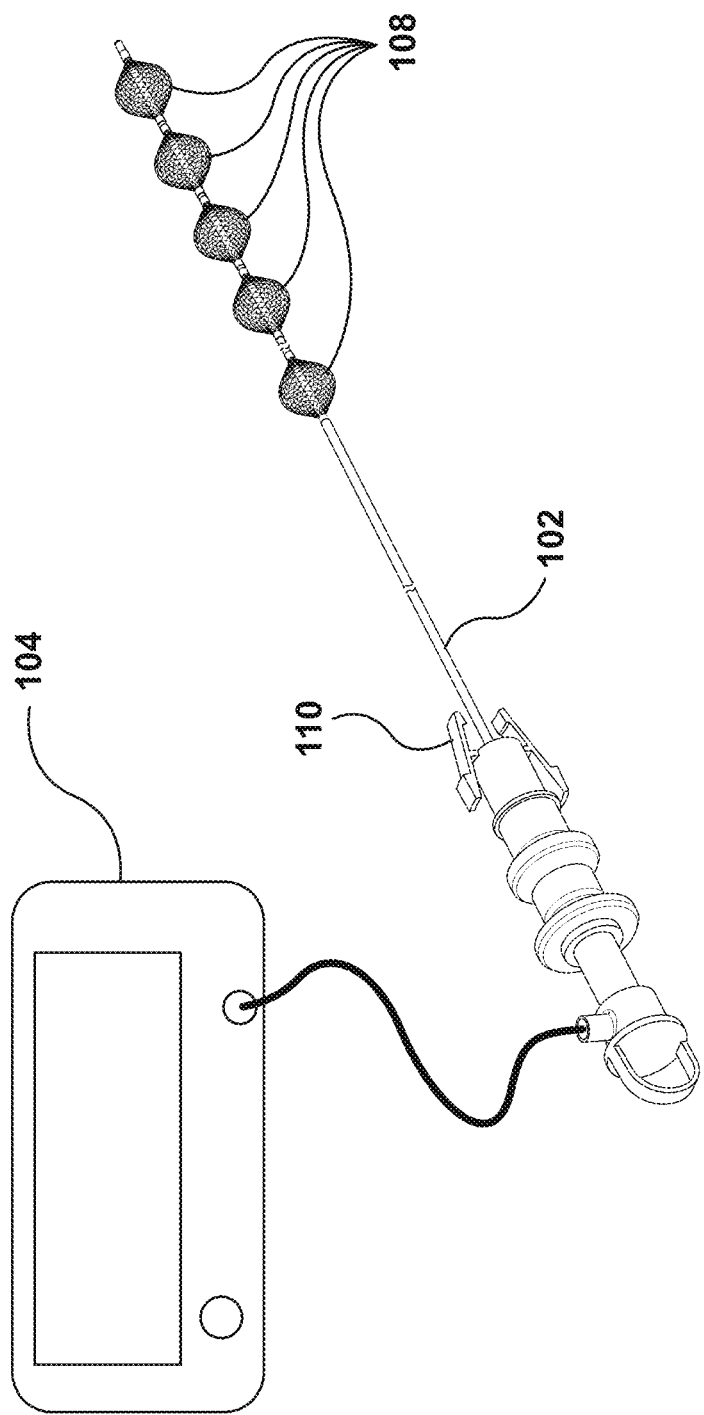
FIG. 46 illustrates an embodiment of an energy delivery catheter with four energy delivery bodies activatable in a bipolar/multiplexed fashion.

FIG. 46 illustrates an embodiment of an energy delivery catheter 102 with more than two energy delivery bodies 108 (four energy delivery bodies 108 are shown) activatable in a bipolar/multiplexed fashion. In this embodiment, the energy delivery bodies 108 are comprised of braided metal wires, wherein the wires serve as electrodes. Energy delivery bodies 108 can be activated in a bipolar fashion by cycling the power supplied by an external generator 104 between any pair of two energy delivery bodies 108, one of which is neutral. The combination between active and neutral energy delivery bodies 108 can be varied as well. For example, in one embodiment the energy can be applied to two or more energy delivery bodies 108 while one energy delivery body 108 serves as a neutral electrode. The combination of active energy delivery bodies 108 and neutral energy delivery bodies 108, the switching/cycling of the energy between active and neutral energy delivery bodies 108, the choice between activated and deactivated energy delivery bodies 108 is achieved through the energy delivery algorithm 152 of the generator 104. The algorithm 152 can apply and distribute energy between energy delivery bodies 108 based on a pre-defined approach, imaging data, and other factors determining the desired area and depth of treatment.

Figure 47:
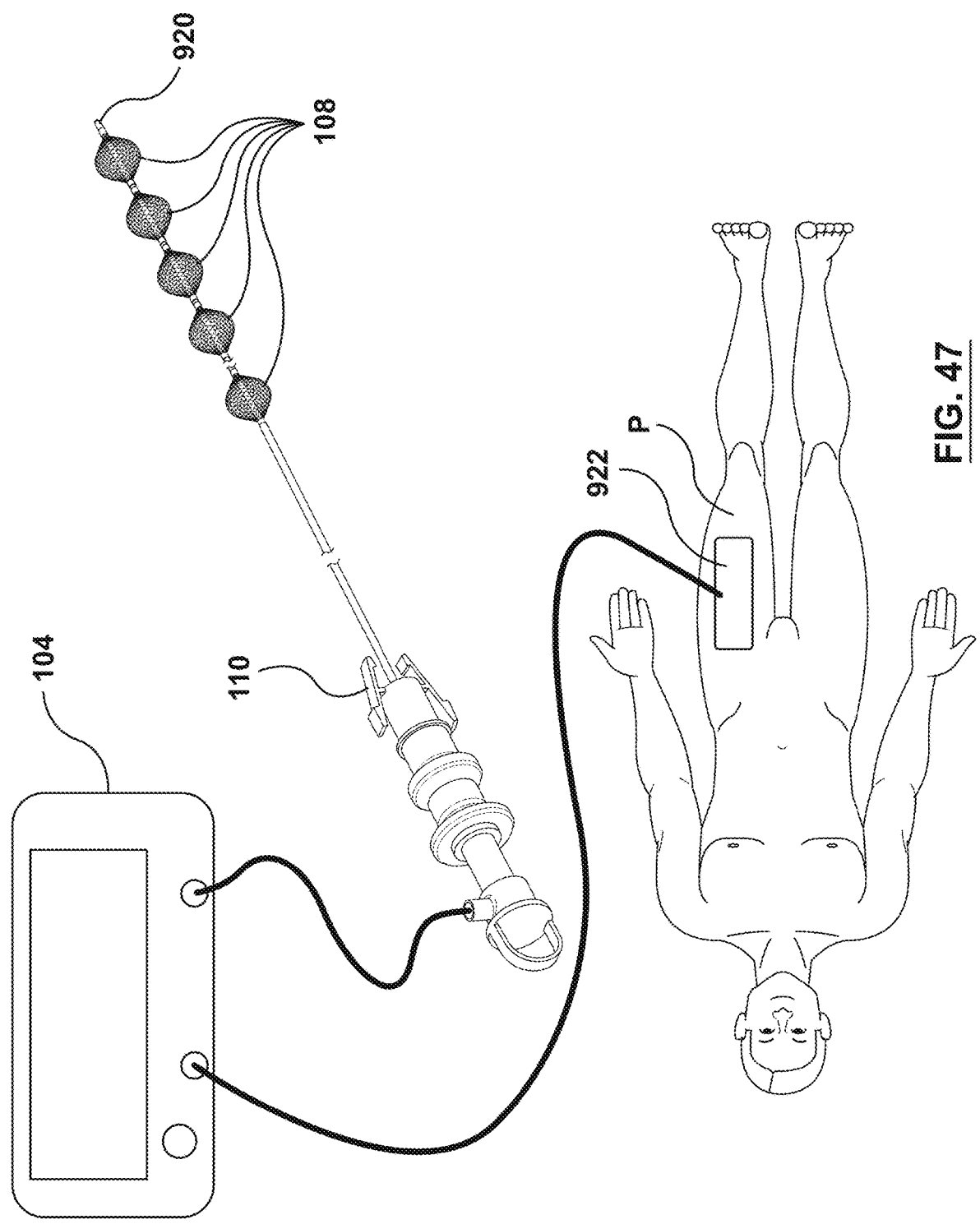
FIG. 47 illustrates monopolar energy delivery by supplying energy between the energy delivery bodies and a dispersive (return) electrode applied externally to the skin of the patient.

FIG. 47 illustrates another embodiment of an energy delivery catheter 102 having a multi-energy delivery body design. In this embodiment, the energy delivery bodies 108 are activated in a monopolar and/or bipolar multiplexed fashion. Monopolar energy delivery can be achieved by supplying energy between one or more energy delivery bodies 108 positioned near the distal end 920 of the catheter 102 and a dispersive (return) electrode 922 applied externally to the skin of the patient P. The combination of active energy delivery bodies 108, the switching/cycling of the energy between the active energy delivery bodies 108 and the dispersive electrode 922, and the choice between activated and non-activated energy delivery bodies 108 is achieved through the energy delivery algorithm 152 of the generator 102. The algorithm 152 can apply and distribute energy between energy delivery bodies 108 based on a pre-defined approach, imaging data and other factors determining the desired area and depth of treatment.

It may be appreciated that many of the figures herein depict energy delivery bodies 108 of essentially the same size (e.g., length, diameter) and shape for illustrative purposes, and should not be considered limiting. In some embodiments, the energy delivery bodies can vary in size in order to account for tapering of the airway lumen, better localize the energy field, and/or enhance treatment of the tissue. For example, if the desired catheter placement requires a distal energy delivery body to be in the lobar bronchi (about 9 mm-12 mm in diameter) and a proximal energy delivery body to be in the mainstem bronchi (about 12 mm-16 mm in diameter), the distal energy delivery body can be designed to expand to about 12 mm and the proximal energy delivery body to expand to about 16 mm. The energy delivery bodies can also be of different sizes to better localize the energy field. For example, if monopolar energy delivery is desired, it can be beneficial to have the dispersive (neutral) electrode incorporated into the catheter or another device (instead of placed on the outside of the patient, as shown in FIG. 47) in order to locate it closer to the treatment energy delivery body to better localize the energy. This can reduce the risk of causing muscle contractions or arrhythmias, as a lower voltage can be applied to generate the same electric field. The energy delivery bodies can also be of different sizes in order to enhance the ability to separate the tissue. In some embodiments, the active portion of the energy delivery body can be that area which is in contact with the airway. It is therefore possible that the area of contact for two different energy delivery bodies is nearly the same, for example, if two similarly-sized energy delivery bodies are placed into a similarly-sized airway and expanded approximately the same. However, if two similarly-sized energy delivery bodies are placed into different-sized airways and/or not expanded the same, the active portion of each energy delivery body can vary significantly. If one electrode is configured to have more contact area than the other, a non-uniform electric field can polarize the cells such that a greater force can be generated in an effort to separate the tissue. The energy delivery body can also be configured to bias the energy field normal to the epithelium or to create shear along the epithelium.

Figure 48:
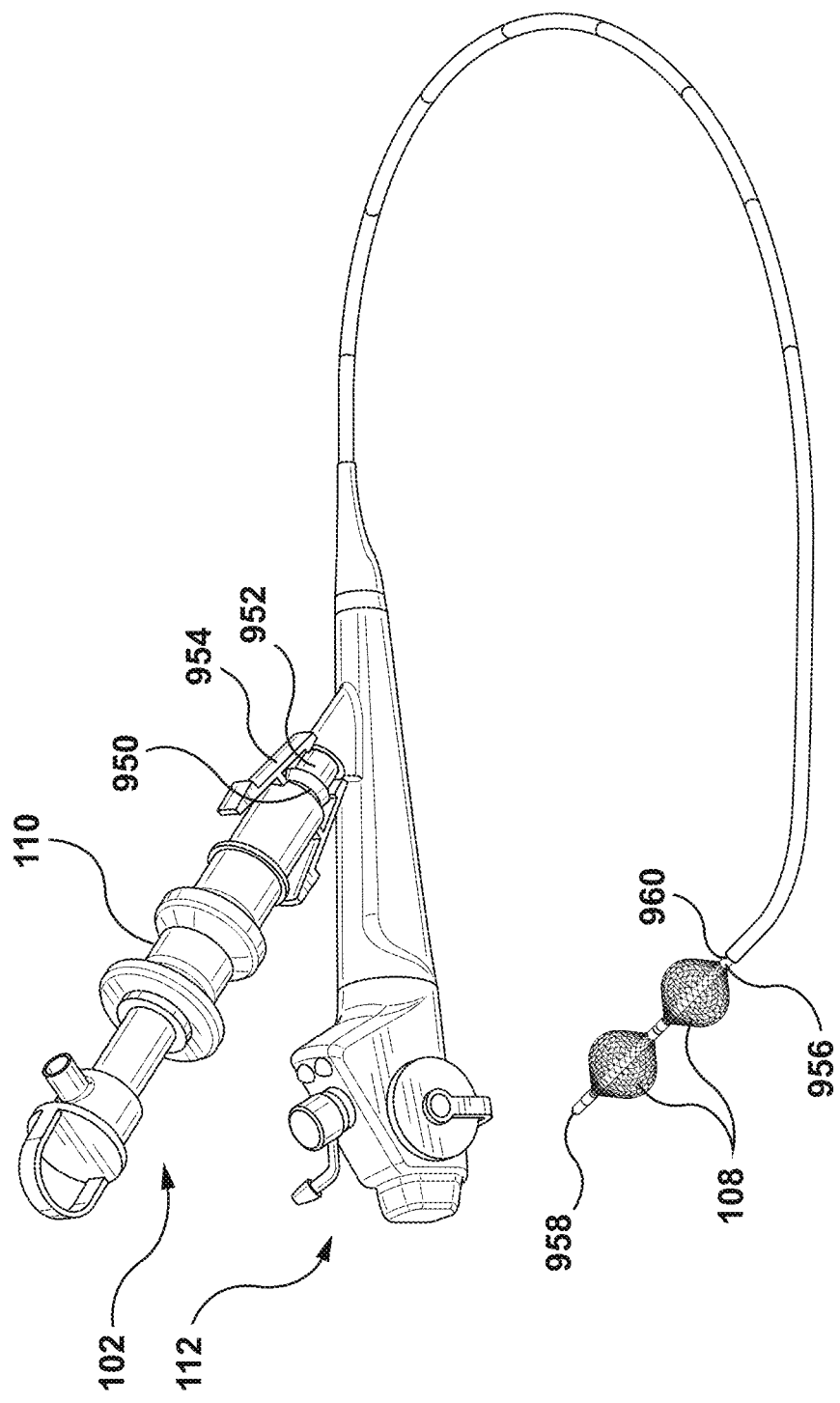
FIG. 48 illustrates an example catheter removably connected to a bronchoscope.

FIG. 48 depicts an example catheter 102 configured to removably connect to a bronchoscope 112. I this embodiment, a handle 110 of the catheter 102 includes a docking mechanism 950 that is removably connectable (e.g., snapped) to an external port 952 of a working channel of the bronchoscope 112. Such a docking mechanism 950 can make it easier for the operator to control both the bronchoscope 112 and the catheter 102 during the procedure. In another embodiment, the handle 110 is connectable to various bronchoscope attachments and/or accessories (e.g., valve, not shown) that are installable onto the external port 952 of the working channel of the bronchoscope 112. In yet another embodiment, the handle 110 does not have any mechanisms that connects to the external port or valve of the working channel of the bronchoscope 112. In such instances, the stability of the catheter 102 is achieved by means of friction between the shaft of the catheter 102 and accessories (for example valve) that are installed onto the external port 952 of the working channel of the bronchoscope 112.

In some embodiments, the length between a distal end 954 of the catheter handle 110 and the proximal end 956 of the most proximal energy delivery body 108 is tailored to be substantially equal to the length of the working channel of the bronchoscope 112, based on the distance between the proximal end of the working channel and the distal end of the working channel. When the catheter handle 110 is connected (e.g. snapped) to the external port 952 of the working channel of the bronchoscope 112, the energy delivery body or bodies 108 is/are introduced into the lung passageway. The step of positioning the one or more energy delivery bodies 108 within the target area of the lung passageway can be accomplished by moving the bronchoscope 112, and thereby moving the catheter 102 thereattached. When the one or more energy delivery bodies 108 are successfully positioned within the target area and this position is visually assessed and confirmed by the operator (e.g. using visual bronchoscopy) the one or more energy delivery bodies can be expanded, deployed or otherwise positioned into tissue contact via a mechanism in the catheter handle 110 which is operatively connected to the one or more energy delivery bodies 108 (e.g. lever, slider, plunger, button operatively connected to the one or more energy delivery bodies 108 (via a pull wire or by other mechanisms) and ready for energy delivery.

In some embodiments, the length between the distal end 954 of the catheter handle 110 and the distal most distal end 958 of the one or more energy delivery bodies 108 is tailored to be substantially equal to the length of the working channel of the bronchoscope 112, based on the distance between the proximal end of the working channel 954 and the distal end of the working channel 960. When the catheter handle 110 is connected (e.g., snapped) to the external port 952 of the bronchoscope working channel, the one or more energy delivery bodies 108 are not yet introduced (FIG. 49A) into the bronchus lumen and are situated within the working channel of the bronchoscope 112. The step of introducing the one or more energy delivery bodies 108 into the bronchus lumen (FIG. 49B) can be achieved via a primary mechanism of the handle 112 (e.g. lever, slider, plunger, button). When one or more energy delivery bodies 108 are successfully positioned within the target area and this position is visually assessed and confirmed by the operator (e.g. using visual bronchoscopy) the electrodes can be expanded, deployed or otherwise positioned into tissue contact (FIG. 49C) via a secondary mechanism of the handle 112 (e.g. lever, slider, plunger, button) and ready for energy delivery. In one configuration, a secondary handle mechanism (e.g. lever, slider, plunger, button) is operatively connected (for example bonded or welded) to the proximal end of the catheter sheath. To deploy/expand one or more energy delivery bodies 108 the operator would move a secondary mechanism proximally thus moving the catheter sheath proximally which removes the constraint of the one or more energy delivery bodies 108 and allows them to expand. In another configuration, a secondary handle mechanism (e.g. lever, slider, plunger, button) is operatively connected (for example bonded or welded) to the proximal end of the pull or push wire/tubing. To deploy or expand the one or more energy delivery bodies 108 the operator would move a secondary mechanism proximally thus pulling the pull wire or tubing or distally thus pushing the push wire/tubing. In both embodiments depending on the specific configuration of the catheter and its deployment mechanism the action performed by the operator using a secondary handle mechanism will lead to the deployment or expansion of the one or more energy delivery bodies 108. In yet another configuration, there can be more than one secondary handle mechanism connected to more than one pull or push wires or tubings. In this scenario the expansion of one or more energy delivery bodies 108 can be controlled independently by activating different secondary handle mechanisms at different times and at different levels of magnitude.

In some embodiments, the length between the distal end of the catheter handle and the proximal end of the one or more energy delivery bodies 108 is tailored to be substantially longer than the length of the working channel. When one or more energy delivery bodies 108 are introduced into the lung passageway, the handle is not in contact with the external port of the bronchoscope working channel. The step of positioning one or more energy delivery bodies 108 within the target area can be accomplished by moving the bronchoscope or alternatively moving the catheter itself. In this case, the catheter is long enough that the catheter handle can be held by the operator or set down on or near the patient to allow the operator to hold the bronchoscope. When one or more energy delivery bodies 108 are successfully positioned within the target area and this position is visually assessed and confirmed by the operator (e.g. using visual bronchoscopy) the one or more energy delivery bodies 108 can be deployed or otherwise positioned into tissue contact via a mechanism in the catheter handle which is operatively connected to the one or more energy delivery bodies 108 (e.g. lever, slider, plunger, button) and ready for energy delivery.

According to embodiments described herein, which can partially or as a whole combine with other embodiments, the handle of the catheter can include a docking mechanism that can be removably connected (e.g., snapped) onto the external port of the bronchoscope working channel. In another embodiment, the handle can be connected to the various attachments and/or accessories (e.g., valve) that are installed onto the external port of the bronchoscope working channel. In yet another embodiment, the handle may not have any mechanisms that snap onto the external port of the bronchoscope working channel and the stability of the device is achieved by means of friction between the shaft of the catheter and accessories (e.g., valve) that are installed onto the external port of the bronchoscope working channel.

VIII. TREATMENT PATTERNS

It may be appreciated that a patient P may possess a single target zone for treatment or multiple target zones. A target zone is a contiguous area of a lung passageway that is targeted for treatment. A single lung passageway may include multiple target zones. Likewise, target zones may be located along separate lung passageways. Each target zone may include one or more target segments. A target segment is a portion of the lung passageway that is treatable by a single placement of the catheter 102 (i.e. single treatment). Thus, the target segment is defined by the outer area borders along the lung airway wall W within which the wall tissue has been treated by the one or more electrodes 108 of the catheter 102. It may be appreciated that different embodiments of the catheter 102 may cover differing sized areas of a lung passageway. Thus, the size of a target segment may vary based on catheter 102/system 100 design. In addition, the catheter 102 may be sequentially moved along a lung passageway to create multiple adjacent target segments, wherein adjacent target segments cover the target zone.

Thus, methods for treating the airway of a patient can include: (a) performing a single treatment at a target segment, (b) performing two or more treatments at adjacent target segments such that the overall treatment zone is generally continuous, and/or (c) performing two or more treatments spaced apart from one another. FIG. 50 is a schematic illustration of a single target segment 1000 within a mainstem bronchi MB of a lung. In this embodiment, the target segment 1000 is treated by placement of the one or more energy delivery bodies 108 of the catheter 102 and delivery of treatment energy thereto. FIG. 51 is a schematic illustration of two target segments 1000a, 1000b positioned adjacent to each other such that the overall target or treatment zone 1002 is generally contiguous. Typically, the two target segments 1000a, 1000b are treated by first positioning the catheter 102 so as to treat the first target segment 1000a, then repositioning the catheter 102 so as to treat the second target segment 1000b. It may be appreciated that the various target segments may alternatively be treated with different catheters 102. It may also be appreciated that the target segments 1000a, 1000b may be treated in any order. Likewise, in some embodiments, target segments overlap. Thus, both FIGS. 50-52 illustrate a single target zone within a lung passageway. FIG. 52 is a schematic illustration of two target zones 1004, 1006 within a patient. In this embodiment, a first target zone 1004 is disposed within a mainstem bronchi MB and a second target zone 1006 is disposed within a lobar bronchi LB of a lung. Here, the first target zone 1004 is covered by a target segment 1008 and the second target zone 1006 is covered by a target segment 1010 wherein the target segments 1008, 1010 are space apart from one another. Again, the two target segments 1008, 1010 may be treated by first positioning the catheter 102 so as to treat the first target segment 1008, then repositioning the catheter 102 so as to treat the second target segment 1010. It may be appreciated that the various target segments may alternatively be treated with different catheters 102. It may also be appreciated that the target segments 1008, 1010 may be treated in any order. It is understood that these figures provide example treatment patterns that can be used solely or in combination with one another to yield the desired outcome.

It may also be appreciated that within a target segment, the lung passageway tissue may receive a variety of treatment patterns at any given cross-section. For example, some embodiments include treating the full circumference of the airway over a given length of the target segment and other embodiments include treating one or multiple discrete portions of the circumference of the airway over a given length of the target segment.

Figure 54:
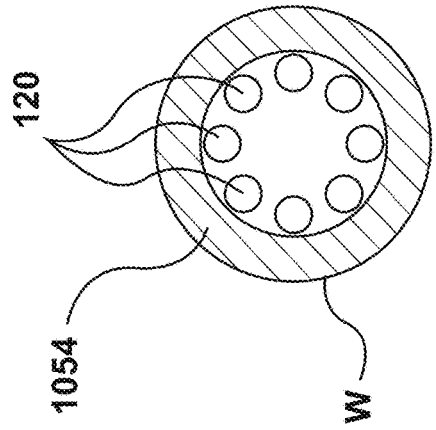
FIG. 54 is a schematic cross-sectional view of the energy delivery body of FIG. 50 positioned within a lung passageway having an airway wall.
Figure 53:
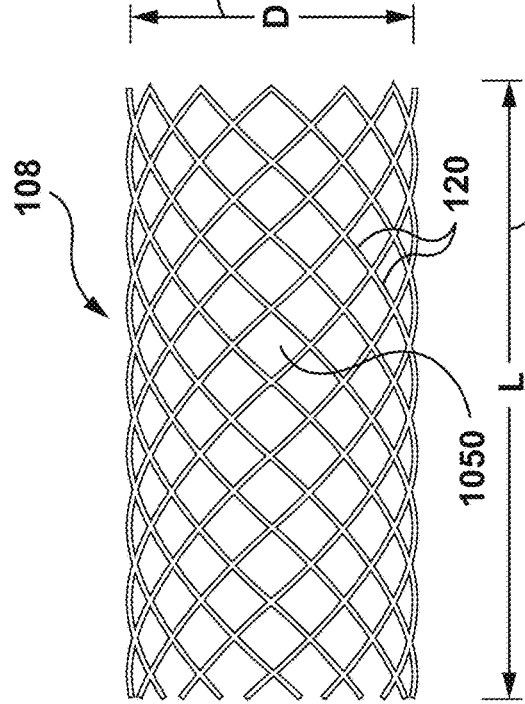
FIG. 53 is a schematic side view illustration of a portion of an energy delivery body comprised of a braided basket.
Figure 55:
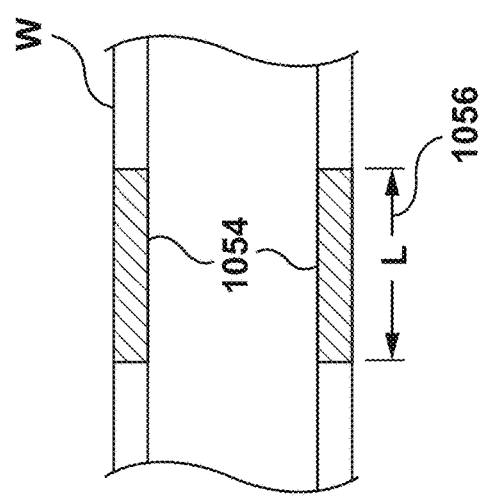
FIG. 55 is a schematic illustration of the effect of continuous full circumference treatment of an airway along a length of the energy delivery body.

FIG. 53 is a schematic side view illustration of a portion of an energy delivery body 108 comprised of a braided basket. The braid is comprised of individual wires 120 which deliver energy. Between the wires are pores 1050. Depending on the degree of expansion (indicated by diameter 1052), the pore size will vary. FIG. 54 is a schematic cross-sectional view of the energy delivery body 108 of FIG. 53 positioned within a lung passageway having an airway wall W. Thus, the energy delivery body 108 is illustrated as a plurality of cross-sections of the wires 120 disposed against the inner lumen of the lung passageway (i.e. along the inner surface of the airway wall W). In some embodiments, treatment of a continuous full circumference (shading, 1054) of the airway W is achieved. Likewise, in some embodiments, continuous full circumference treatment along a length 1056 of the energy delivery body 108 is also achieved. This effect is illustrated in FIG. 55.

Figure 56:
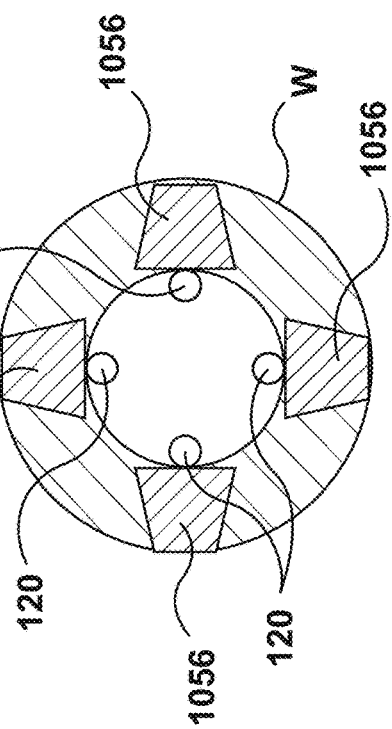
FIG. 56 is a schematic illustration of a discontinuous tissue effect in a lung passageway.

In some embodiments, in order to achieve substantially continuous, full circumference treatment over a given length, at least the applied electric field (V/cm) and the electrode design are taken into consideration. In one example, the electric field is applied in a monopolar fashion, wherein the field is applied to substantially the energy delivery body 108, and a dispersive (neutral) electrode is positioned either on the exterior of the patient or elsewhere within the body. The change and/or distribution of the magnitude of the field will depend on the applied voltage and the geometric relationship of the wires 120. In the example provided in FIGS. 53-55, the energy delivery body 108 in contact with the circumference and length of tissue to be treated is constructed from a metallic braid of wires 120. By having many wires 120 close together, the field between each wire 120 can be sufficient to cause the desired tissue effects continuously around the entire circumferential area of contact 1054. In this example, the diameter 1052 is designed to expand from approximately 2-3 mm in diameter when fully collapsed for delivery to about 10 mm, 12 mm, 15 mm, 18 mm, 20 mm, or 22 mm in diameter when fully expanded, including all values and subranges in between. Depending on the degree of expansion, the pore 1050 size will vary, but will generally be effective at generating a continuous tissue effect with pore sizes up to at least 10 mm$^2$. If the pore size becomes significantly larger, the same field applied can result in a discontinuous tissue effect (indicated by shading 1056), as depicted in FIG. 56. In this embodiment, the energy delivery body is comprised of four wires 120, wherein each wire 120 provides a tissue effect contributing to an overall discontinuous tissue effect. This can increase the speed of healing while still affecting a sufficient amount of tissue to provide a clinical benefit. A discontinuous lesion can also be achieved by reducing the applied electric field.

It may be appreciated that some embodiments have energy delivery bodies which include treating portions of the circumference ranging from about 25 to about 50%, from about 50% to about 75%, or from about 75% to about 100%, including all values and subranges in between. Some embodiments include treating lengths ranging from about 5 mm to about 20 mm, including all values and subranges in between, allowing for sufficient flexibility to treat a wide range of patient anatomies while minimizing the number of individual treatments to be performed.

IX. GENERAL EMBODIMENTS

In some embodiments described herein, which can partially or as a whole be combined with other embodiments, a pulmonary tissue modification system for performing a pulmonary procedure can include an energy producing generator, an energy delivery catheter, accessories, and one or more imaging modalities.

In some embodiments, a bipolar catheter with two energy delivery bodies mounted near the distal end is connected to an energy producing generator outside of the body. The distal end of the catheter is passed through the mouth or nose and into the bronchial tree using a bronchoscope or other direct visualization system. The energy delivery bodies are deployed, expanded and/or otherwise positioned such that they contact the airway wall. The operator can then activate the generator via any suitable interface such as, for example, a foot switch, a button on the generator, a button on the catheter, or remote control, to deliver energy to airway tissue adjacent to and/or between the electrodes. In some embodiments, the operator can move the energy delivery bodies to another section of the diseased airway to deliver another treatment, or elect to treat the entire surface of a section of the airway, or multiple sections of the airways. In some embodiments, more than one treatment can be applied to the same portion of the airway, depending on the desired depth of penetration. In some embodiments, two or more different energy delivery algorithms can be employed to affect the depth of penetration.

In some embodiments, a monopolar catheter, with a single energy delivery body mounted near the distal end, is connected to an energy producing generator outside of the body. The distal end of the catheter is passed through the mouth or nose and into the bronchial tree using a bronchoscope or other direct visualization system. The electrode is deployed, expanded and/or otherwise positioned such that it contacts the airway wall. A dispersive (neutral) or return electrode is affixed to another surface of the patient (e.g., an external location, such as the patient's skin, and is also connected to the electrical generator. The operator can then activate the generator via, for example, a foot switch, a button on the generator, a button on the catheter, or remote control to deliver energy to airway tissue via the electrode. The operator can move the energy delivery body to another section of the diseased airway to deliver a treatment, or elect to treat the entire surface of a section of the airway, or multiple sections of the airways. In some embodiments, two or more monopolar energy delivery bodies can be incorporated into one or more catheters to enable treatment of multiple locations without repositioning the catheter(s). More than one treatment can be applied to the same portion of the airway, depending on the desired depth of penetration. In some embodiments, two or more different energy delivery algorithms can be employed to affect the depth of penetration. In some embodiments, a user interface on the generator can be used to select the desired treatment algorithm, while in other embodiments, the algorithm can be automatically selected by the generator based upon information obtained by one or more sensors.

In some embodiments, a catheter with a plurality of energy delivery bodies mounted near the distal end is connected to an energy producing generator outside of the body. The distal end of the catheter is passed through the mouth or nose and into the bronchial tree using a bronchoscope or other direct visualization system. The energy delivery bodies are deployed, expanded, or otherwise positioned such that they contact the airway wall. The operator can then activate the generator via, for example, a foot switch, a button on the generator, a button on the catheter, or remote control to deliver energy to airway tissue via the energy delivery bodies. In some embodiments, the energy delivery can be multiplexed across any one or more of the energy delivery bodies in any suitable pattern to affect the desired target tissue. In some embodiments, a dispersive (neutral) electrode can be affixed to another surface of the patient, such as the patient's skin, and also connected to the electrical generator to allow for monopolar energy delivery to any of the energy delivery bodies. More than one treatment can be applied to the same portion of the airway, depending on the desired depth of penetration. In some embodiments, two or more different energy delivery algorithms can be employed to affect the depth of penetration. The user interface on the generator can be used to select the desired treatment algorithm, or the algorithm can be automatically selected by the generator based upon information In some embodiments, the targeted treatment area can be identified and used to select a treatment algorithm sufficient to affect the pathogenic cells and/or deeper tissues. The electrode system can then be deployed at the site of pathogenic cells and/or abnormal airway wall tissue and energy delivered to affect the target tissue. The imaging modality (or modalities) can be used before, during, between, and/or after treatment(s) to determine where treatment(s) have or have not been delivered and/or whether the energy adequately affected the airway wall. If it is determined that a target treatment area was missed or that a target treatment area was not adequately affected, the energy delivery can be repeated followed by imaging as described herein until adequate treatment is achieved. Further, the imaging information can be utilized to determine if specific cell types and or a desired depth of therapy was applied. This can allow for customization of the energy delivery algorithm for treating a wide variety of patient anatomies.

In some embodiments, any of the apparatuses and/or systems described herein can be used in methods for treating diseased airways, and/or other lung tissue (e.g., parenchyma), which can generally include accessing the airway, and optionally performing pre-, intra-, and/or post-procedural imaging to plan, guide and/or verify treatment. In some embodiments, the methods can further include one or more of treating a sufficient treatment zone with each energy application, treating a sufficient overall treatment area, treating to a sufficient depth, treating a pre-defined cell type or types, customizing therapy based on imaging and/or sensor information, and combinations thereof.

X. EXAMPLES

The following examples further illustrate embodiments of the systems and methods disclosed herein, and should not be construed in any way as limiting their scope.

Example 1: Circumferential Treatment and Tissue Effect with a Bipolar System A non-thermal energy delivery apparatus having bipolar expandable energy delivery bodies was developed. The apparatus included two energy delivery bodies, each comprised of nitinol, braided, expanding electrodes mounted concentrically on a catheter shaft with a mechanism to expanded and contract both energy delivery bodies (e.g., see FIG. 27). The expanded energy delivery body diameters ranged from about 5 mm to about 20 mm. The energy delivery bodies were substantially equal in length at about 3 cm each, and were spaced along the longitudinal axis of the catheter shaft about 2.5 cm apart from edge to edge. To evaluate the effect of pulsed high-voltage energy on epithelial and submucosal tissue layers within the airway, the apparatus was introduced into the left and/or right bronchi of live, anesthetized pigs and energy was delivered in the form of bipolar, square-wave pulses at a pulse frequency of about 300 kHz, pulse amplitude of about 4000V, and total energy delivery duration of about 415 microseconds (83 microseconds per packet, 5 packets).

Following the procedure, the animals were recovered, then subsequently euthanized after approximately twenty-four hours. The airways were then dissected out and fixed in formalin for about forty-eight hours. The airways were then sectioned at approximately 5 mm increments and processed for histology in typical fashion. Sections of both treated and untreated areas were processed for comparison purposes. Slides were prepared using a hematoxylin and eosin (H&E) stain.

Figure 57A:
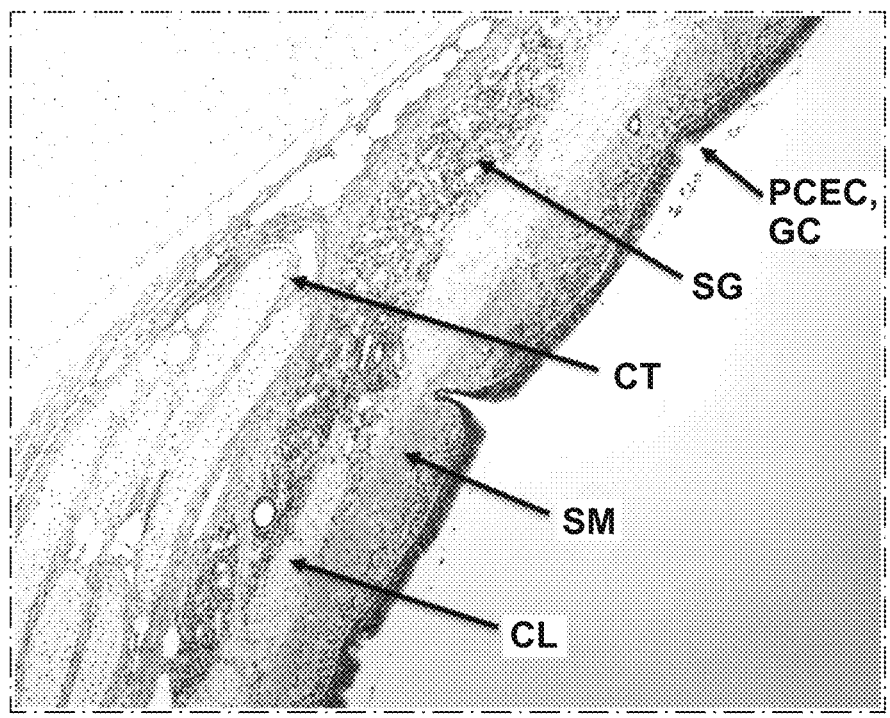
FIGS. 57A-57B illustrate histology example (Lab 6, Animal 1-10085)
Figure 57B:
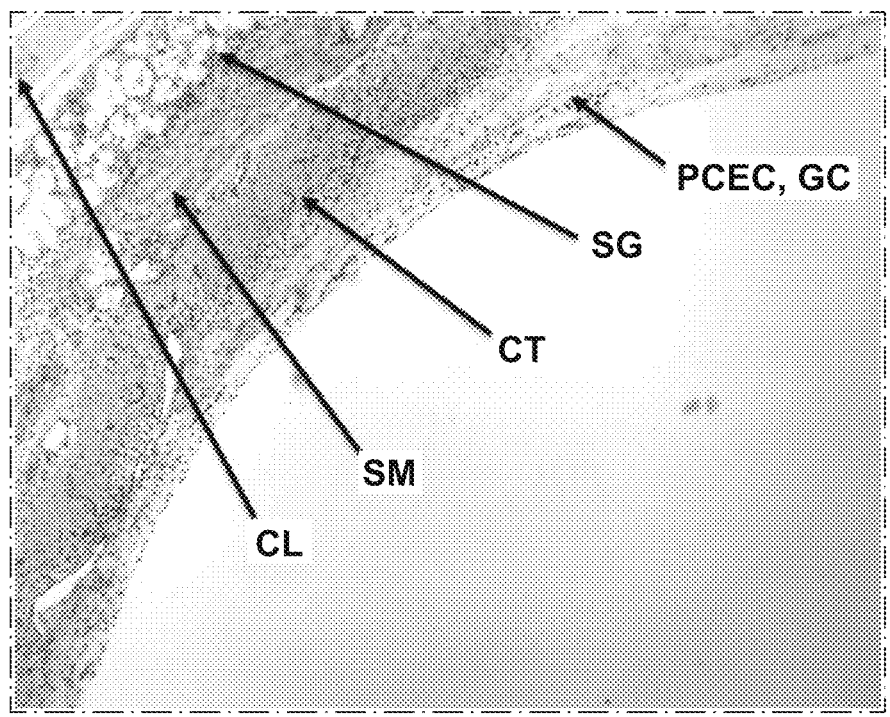

FIG. 57A shows a typical section of healthy, untreated airway, and FIG. 57B shows a typical section of treated airway, 24 hrs post energy delivery. In the untreated airway (FIG. 57A), ciliated epithelium E with pseudostratified columnar epithelial cells PCEC and goblet cells GC and intact submucosal structures, including submucosal glands SG, connective tissue CT, smooth muscle SM, and cartilage CL can be observed. In the treated airway (FIG. 57B), epithelial E with pseudostratified columnar epithelial cells PCEC and goblet cells GC have been substantially removed or destroyed, leaving only cellular remnants and the basement membrane. Further, the submucosal structures have been affected; most notably, submucosal gland cells SG are mostly absent, and extra-cellular gland structures have been disrupted. Smooth muscle SM and connective tissue layers CT also show signs of cellular damage and disruption while the cartilage CL was left unaffected.

Example 2: Circumferential Treatment and Tissue Effect with a Monopolar System A non-thermal energy delivery apparatus having a monopolar expandable energy delivery body was developed. The apparatus included a single energy delivery body comprised of nitinol, braided, expanding electrode mounted concentrically on a catheter shaft with a mechanism to expanded and contract the energy delivery body (e.g., see FIG. 26). The expanded energy delivery diameter ranged from about 5 mm to about 20 mm. To evaluate the effect of pulsed high-voltage energy on epithelial and submucosal tissue layers within the airway, the apparatus was introduced into the left and/or right bronchi of live, anesthetized pigs and energy was delivered in the form of bipolar, square-wave pulses at a pulse frequency of 300 kHz, pulse amplitude of 4000 V and total energy delivery duration of 415 microseconds (83 microseconds per packet, 5 packets).

Following the procedure, the animals were recovered, then subsequently euthanized after approximately twenty-four hours. The airways were then dissected out and fixed in formalin for about forty-eight hours. The airways were then sectioned at approximately 5 mm increments and processed for histology in typical fashion. Sections of both treated and untreated areas were processed for comparison purposes. Slides were prepared using a hematoxylin and eosin (H&E) stain.

Figure 58A:
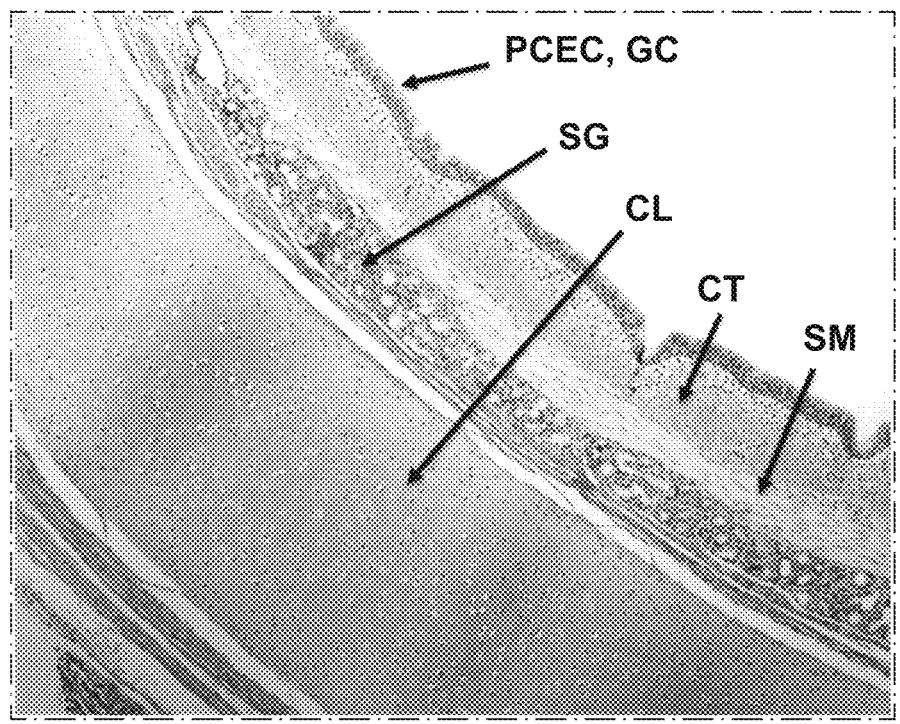
FIGS. 58A-58B illustrate another histology example (Lab 6, Animal 1-10085)
Figure 58B:
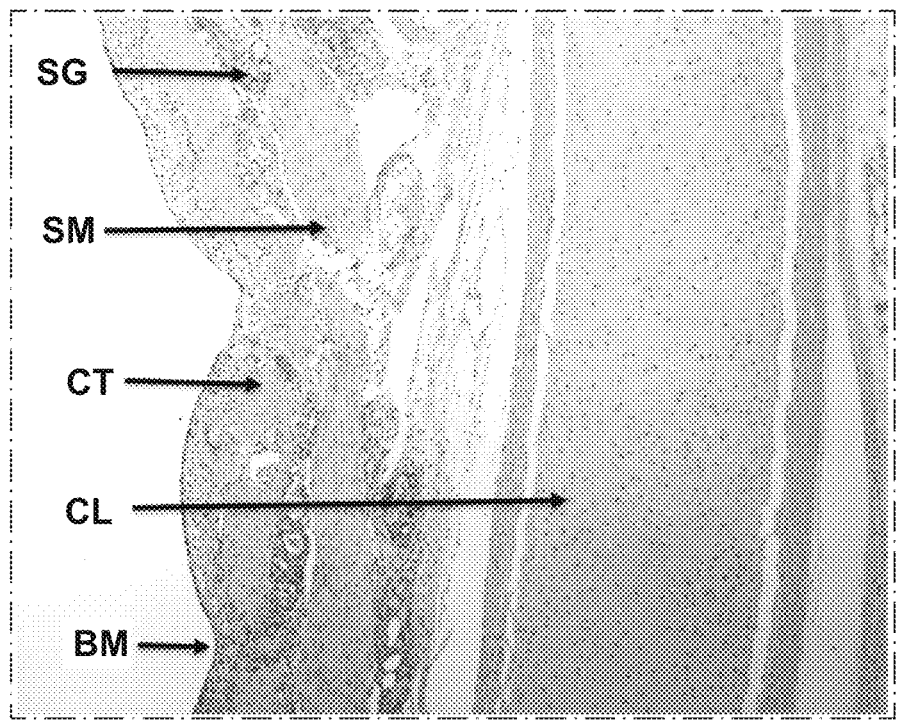

FIG. 58A shows a typical section of healthy, untreated airway and FIG. 58B shows a typical section of treated airway 24 hrs post energy delivery. In the untreated airway (FIG. 58A), ciliated epithelium E with pseudostratified columnar epithelial cells PCEC and goblet cells GC and intact submucosal structures, including submucosal glands SG, connective tissue CT, cartilage CL and smooth muscle SM can be observed. In the treated airway (FIG. 58B) epithelial E and goblet cells GC have been substantially removed or destroyed, leaving only cellular remnants and the basement membrane BM. Further, the submucosal structures have been affected; most notably, submucosal gland cells SG are absent in some locations. In this example, extra-cellular gland structures, including smooth muscle SM and connective tissue layers CT have been left largely unaffected. The cartilage CL was left unaffected. The treatment affects are similar using either the bipolar or monopolar systems, with tissue changes noted where the electrode is in contact with the airway.

As used herein, the terms "about" and/or "approximately" when used in conjunction with numerical values and/or ranges generally refer to those numerical values and/or ranges near to a recited numerical value and/or range. In some instances, the terms "about" and "approximately" can mean within ±10% of the recited value. For example, in some instances, "about 100 [units]" can mean within ±10% of 100 (e.g., from 90 to 110). The terms "about" and "approximately" can be used interchangeably.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating mucus hypersecretion by a portion of a wall of a lung passageway of a patient, the method comprising:

positioning an electrode within a lumen of the lung passageway so that the electrode is able to transmit energy to the portion of the wall of the lung passageway; and providing an electrical signal to energize the electrode so as to transmit the energy to the portion of the wall of the lung passageway for a duration of treatment to treat mucus hypersecretion by the portion of the wall of the lung passageway, wherein the electrical signal includes distinct energy packets and each energy packet comprises a series of biphasic pulses.

2. The method of claim 1, wherein the energy selectively treats particular cells associated with mucus hypersecretion of the lung passageway.

3. The method of claim 1, wherein the energy is below a threshold for thermal ablation of the wall of the lung passageway throughout the duration of treatment.

4. The method of claim 1, wherein providing the electrical signal to energize the electrode transmits the energy to a select target layer of the portion of the wall.

5. The method of claim 1, wherein each energy packet has a cycle count of up to 2,000 biphasic pulses.

6. The method of claim 5, wherein each energy packet has a cycle count of up to 60 biphasic pulses.

7. The method of claim 1, wherein the electrical signal includes five distinct energy packets and each of the five distinct energy packets has a duration of 100 microseconds.

8. The method of claim 1, wherein the electrical signal includes rest periods of 0.0014 seconds to about 10 seconds between each of the distinct energy packets.

9. The method of claim 1, wherein the treatment kills particular pathogens within the lung passageway.

10. The method of claim 1, wherein the electrode includes a plurality of wires forming a basket, and wherein positioning the electrode within the lumen of the lung passageway comprises expanding the basket within the lumen of the lung passageway.

11. The method of claim 1, further comprising:
positioning a return electrode on the patient, and
wherein the energy is transmitted in a monopolar fashion toward the return electrode.

12. A method for selectively treating particular cells associated with mucus hypersecretion of a portion of a wall of a lung passageway of a patient, the method comprising:
positioning an electrode within a lumen of the lung passageway so that the electrode is able to transmit energy to the portion of the wall of the lung passageway; and
providing an electrical signal to energize the electrode so as to transmit non-thermal energy to the portion of the wall of the lung passageway for a duration of treatment to selectively treat the particular cells associated with mucus hypersecretion of the lung passageway,
wherein the non-thermal energy is below a threshold for thermal ablation of the wall of the lung passageway throughout the duration of treatment.

13. The method of claim 12, wherein the electrical signal includes distinct energy packets and each energy packet comprises a series of biphasic pulses.

14. The method of claim 13, wherein the electrical signal includes up to 20 distinct energy packets.

15. The method of claim 14, wherein the electrical signal includes five distinct energy packets and each of the five distinct energy packets has a duration of 100 microseconds.

16. The method of claim 13, wherein the electrical signal includes rest periods of 0.0014 seconds to about 10 seconds between each of the distinct energy packets.

17. The method of claim 12, wherein selectively treats comprises selectively removes and/or kills the particular cells.

18. The method of claim 12, wherein selectively treats comprises selectively modifies the particular cells.

19. The method of claim 12, wherein the particular cells include endothelial cells.

20. The method of claim 12, wherein the particular cells include submucosal glands.

21. A method for treating a portion of a wall of a lung passageway of a patient, the method comprising:
positioning an electrode within a lumen of the lung passageway so that the electrode is able to transmit energy to the portion of the wall of the lung passageway; and
providing an electrical signal to energize the electrode so as to transmit the energy up to and at least partially including a target layer within a mucosa of the portion of the wall of the lung passageway for a duration of treatment,
wherein the energy is below a threshold for thermal ablation of the wall of the lung passageway throughout the duration of treatment.

22. The method of claim 21, wherein the target layer is a basement membrane.

23. The method of claim 21, wherein the target layer is an epithelial layer.

24. The method of claim 21, wherein the electrical signal is discontinuous and includes distinct energy packets and each energy packet includes a series of biphasic pulses.

25. The method of claim 21, further comprising:
selectively treating particular cells associated with mucus hypersecretion.

26. The method of claim 25, wherein the particular cells include epithelial cells.

27. A method of treating a portion of a wall of a lung passageway of a patient with a catheter having an electrode disposed near its distal end, the method comprising:
advancing the distal end of the catheter into a lumen of the lung passageway and positioning the electrode within the lumen so that the electrode is able to transmit energy to the portion of the wall of the lung passageway; and
providing a discontinuous electrical signal to energize the electrode so as to transmit the energy to the portion of the wall of the lung passageway for a duration of treatment, the energy transmitted to the portion of the wall of the lung passageway over the duration of treatment operable to modify cells within the portion of the wall of the lung passageway.

28. The method of claim 27, wherein the discontinuous electrical signal includes five distinct energy packets and each of the five distinct energy packets has a duration of 100 microseconds.

29. The method of claim 27, wherein the discontinuous electrical signal includes distinct energy packets and each of the distinct energy packets includes a series of biphasic pulses.

30. The method of claim 27, wherein the energy transmitted is insufficient to cause muscle contraction throughout the duration of treatment.

* * * * *